United States Patent
Shitagaki et al.

(10) Patent No.: US 10,573,829 B2
(45) Date of Patent: Feb. 25, 2020

(54) LIGHT-EMITTING ELEMENT

(71) Applicant: Semiconductor Energy Laboratory Co., Ltd., Atsugi-shi, Kanagawa-ken (JP)

(72) Inventors: Satoko Shitagaki, Isehara (JP); Satoshi Seo, Sagamihara (JP); Nobuharu Ohsawa, Zama (JP); Hideko Inoue, Atsugi (JP); Kunihiko Suzuki, Isehara (JP)

(73) Assignee: Semiconductor Energy Laboratory Co., Ltd., Atsugi-shi, Kanagawa-ken (JP)

(*) Notice: Subject to any disclaimer, the term of this patent is extended or adjusted under 35 U.S.C. 154(b) by 0 days.

(21) Appl. No.: 15/984,825

(22) Filed: May 21, 2018

(65) Prior Publication Data

US 2018/0269410 A1    Sep. 20, 2018

Related U.S. Application Data

(63) Continuation of application No. 15/454,055, filed on Mar. 9, 2017, which is a continuation of application (Continued)

(30) Foreign Application Priority Data

Feb. 16, 2011    (JP) .................................. 2011-031462

(51) Int. Cl.
*H01L 51/00* (2006.01)
*C07D 209/86* (2006.01)
(Continued)

(52) U.S. Cl.
CPC ........ *H01L 51/0085* (2013.01); *C07D 209/86* (2013.01); *C07D 239/26* (2013.01);
(Continued)

(58) Field of Classification Search
CPC ... H01L 27/30; H01L 27/3239; H01L 31/143; H01L 31/162; H01L 33/08; H01L 33/18;
(Continued)

(56) References Cited

U.S. PATENT DOCUMENTS 5,409,783 A    4/1995 Tang et al.
5,420,288 A    5/1995 Ohta et al.
(Continued)

FOREIGN PATENT DOCUMENTS

AU    2003226473    10/2003
CN    001474633 A    2/2004
(Continued)

OTHER PUBLICATIONS

Tanaka.I et al., "Energy-Transfer Processes between Phosphorescent Guest and Fluorescent Host Molecules in Phosphorescent OLEDs", Highly Efficient OLEDs with Phosphorescent Materials, 2008, pp. 283-309.
(Continued)

*Primary Examiner* — Moin M Rahman
(74) *Attorney, Agent, or Firm* — Fish & Richardson P.C.

(57) ABSTRACT

A light-emitting element having high external quantum efficiency is provided. A light-emitting element having a long lifetime is provided. A light-emitting element is provided which includes a light-emitting layer containing a phosphorescent compound, a first organic compound, and a second organic compound between a pair of electrodes, in which a combination of the first organic compound and the second organic compound forms an exciplex (excited complex). The light-emitting element transfers energy by utilizing an overlap between the emission spectrum of the exciplex and the absorption spectrum of the phosphorescent compound and thus has high energy transfer efficiency.
(Continued)

Therefore, a light-emitting element having high external quantum efficiency can be obtained.

38 Claims, 47 Drawing Sheets

Related U.S. Application Data

No. 13/370,679, filed on Feb. 10, 2012, now Pat. No. 9,604,928.

(51) Int. Cl.
| | |
|---|---|
| *C07D 239/26* | (2006.01) |
| *C07D 241/12* | (2006.01) |
| *C07D 333/76* | (2006.01) |
| *C07D 409/10* | (2006.01) |
| *C07D 471/04* | (2006.01) |
| *C07F 15/00* | (2006.01) |
| *H01L 51/50* | (2006.01) |
| *C09K 11/02* | (2006.01) |
| *C09K 11/06* | (2006.01) |

(52) U.S. Cl.
CPC ......... *C07D 241/12* (2013.01); *C07D 333/76* (2013.01); *C07D 409/10* (2013.01); *C07D 471/04* (2013.01); *C07F 15/0033* (2013.01); *C09K 11/025* (2013.01); *C09K 11/06* (2013.01); *H01L 51/006* (2013.01); *H01L 51/0059* (2013.01); *H01L 51/0061* (2013.01); *H01L 51/0072* (2013.01); *H01L 51/0074* (2013.01); *H01L 51/5016* (2013.01); *C09K 2211/1007* (2013.01); *C09K 2211/1074* (2013.01); *C09K 2211/185* (2013.01); *H01L 51/0052* (2013.01); *H01L 51/0056* (2013.01); *H01L 51/0058* (2013.01); *H01L 2251/5376* (2013.01); *H01L 2251/5384* (2013.01); *H01L 2251/552* (2013.01)

(58) Field of Classification Search
CPC ... H01L 33/24; H01L 51/5032; H01L 25/048; H01L 27/288; H01L 27/32; H01L 33/06; H01L 33/26; H01L 51/0032; H01L 51/50; H01L 2251/50; H01L 51/5068; H01L 51/5084; H01L 51/5296; H01L 2051/0032; H01L 51/0085; H01L 51/0061; H01L 51/006; H01L 51/5016; H01L 51/0074; C09K 11/025; C09K 11/06; C07F 15/0033; C07D 471/04; C07D 333/76; C07D 241/12; C07D 239/26; C07D 209/86; C07D 409/10
See application file for complete search history.

(56) References Cited

U.S. PATENT DOCUMENTS

| | | | |
|---|---|---|---|
| 5,597,890 A | 1/1997 | Jenekhe | |
| 5,597,925 A | 1/1997 | Ohta et al. | |
| 5,610,309 A | 3/1997 | Ohta et al. | |
| 5,656,401 A | 8/1997 | Ohta et al. | |
| 5,709,492 A | 1/1998 | Yasunaga et al. | |
| 5,955,836 A | 9/1999 | Boerner et al. | |
| 6,097,147 A | 8/2000 | Baldo et al. | |
| 6,720,092 B2 | 4/2004 | Hatwar | |
| 6,830,828 B2 | 12/2004 | Thompson et al. | |
| 6,863,997 B2 | 3/2005 | Thompson et al. | |
| 6,869,695 B2 | 3/2005 | Thompson et al. | |
| 6,902,830 B2 | 6/2005 | Thompson et al. | |
| 6,951,694 B2 | 10/2005 | Thompson et al. | |
| 7,001,536 B2 | 2/2006 | Thompson et al. | |
| 7,175,922 B2 | 2/2007 | Jarikov et al. | |
| 7,183,010 B2 | 2/2007 | Jarikov | |
| 7,238,806 B2 | 7/2007 | Inoue et al. | |
| 7,291,406 B2 | 11/2007 | Thompson et al. | |
| 7,291,969 B2 | 11/2007 | Tsutsui | |
| 7,332,857 B2 | 2/2008 | Seo et al. | |
| 7,537,844 B2 | 5/2009 | Thompson et al. | |
| 7,553,557 B2 | 6/2009 | Thompson et al. | |
| 7,572,522 B2 | 8/2009 | Seo et al. | |
| 7,579,090 B2 | 8/2009 | Brown et al. | |
| 7,597,967 B2 | 10/2009 | Kondakova et al. | |
| 7,659,010 B2 | 2/2010 | Burn et al. | |
| 7,696,348 B2 | 4/2010 | Egawa et al. | |
| 7,767,316 B2 | 8/2010 | Deaton et al. | |
| 7,803,468 B2 | 9/2010 | Nariyuki et al. | |
| 7,883,787 B2 | 2/2011 | Thompson et al. | |
| 7,915,409 B2 | 3/2011 | Inoue et al. | |
| 7,943,925 B2 | 5/2011 | Yamazaki | |
| 7,993,760 B2 | 8/2011 | Komori et al. | |
| 8,003,229 B2 | 8/2011 | Sisk et al. | |
| 8,008,489 B2 | 8/2011 | Egawa et al. | |
| 8,034,465 B2 | 10/2011 | Liao et al. | |
| 8,057,921 B2 | 11/2011 | Sisk et al. | |
| 8,062,770 B2 | 11/2011 | Sisk et al. | |
| 8,062,771 B2 | 11/2011 | Sisk et al. | |
| 8,062,772 B2 | 11/2011 | Sisk et al. | |
| 8,062,773 B2 | 11/2011 | Sisk et al. | |
| 8,154,193 B2 | 4/2012 | Tsutsui | |
| 8,216,699 B2 | 7/2012 | Burn et al. | |
| 8,247,086 B2 | 8/2012 | Inoue et al. | |
| 8,263,238 B2 | 9/2012 | Sisk et al. | |
| 8,274,214 B2 | 9/2012 | Ikeda et al. | |
| 8,278,444 B2 | 10/2012 | Inoue et al. | |
| 8,293,921 B2 | 10/2012 | Nomura et al. | |
| 8,304,094 B2 | 11/2012 | Ohsawa et al. | |
| 8,339,036 B2 | 12/2012 | Tsutsui | |
| 8,471,017 B2 | 6/2013 | Egawa et al. | |
| 8,557,402 B2 | 10/2013 | Thompson et al. | |
| 8,569,486 B2 | 10/2013 | Inoue et al. | |
| 8,574,726 B2 | 11/2013 | Thompson et al. | |
| 8,653,537 B2 | 2/2014 | He et al. | |
| 8,758,903 B2 | 6/2014 | Sugita et al. | |
| 8,853,680 B2 | 10/2014 | Yamazaki et al. | |
| 8,890,404 B2 | 11/2014 | Tsutsui | |
| 8,911,881 B2 | 12/2014 | Lee et al. | |
| 8,963,127 B2 | 2/2015 | Pieh et al. | |
| 8,981,355 B2 | 3/2015 | Seo | |
| 8,993,129 B2 | 3/2015 | Endo et al. | |
| 8,994,263 B2 | 3/2015 | Shitagaki et al. | |
| 9,012,036 B2 | 4/2015 | Inoue et al. | |
| 9,040,170 B2 | 5/2015 | Deaton et al. | |
| 9,054,317 B2 | 6/2015 | Monkman et al. | |
| 9,159,942 B2 | 10/2015 | Seo et al. | |
| 9,175,213 B2 | 11/2015 | Seo et al. | |
| 9,187,689 B2 | 11/2015 | Inoue et al. | |
| 9,209,419 B2 | 12/2015 | Tsutsui | |
| 9,219,236 B2 | 12/2015 | Inoue et al. | |
| 9,356,250 B2 | 5/2016 | Ohsawa et al. | |
| 9,406,895 B2 | 8/2016 | Inoue et al. | |
| 9,604,928 B2 | 3/2017 | Shitagaki et al. | |
| 2003/0124381 A1 | 7/2003 | Thompson et al. | |
| 2003/0175553 A1 | 9/2003 | Thompson et al. | |
| 2004/0027059 A1 | 2/2004 | Tsutsui | |
| 2004/0076853 A1 | 4/2004 | Jarikov | |
| 2005/0022116 A1 | 1/2005 | Bowman et al. | |
| 2005/0048310 A1 | 3/2005 | Cocchi et al. | |
| 2005/0106415 A1 | 5/2005 | Jarikov et al. | |
| 2005/0196775 A1* | 9/2005 | Swager | C08G 61/02 435/6.14 |
| 2005/0221116 A1 | 10/2005 | Cocchi et al. | |
| 2005/0221124 A1* | 10/2005 | Hwang | C07F 9/5728 428/690 |
| 2006/0024526 A1 | 2/2006 | Thompson et al. | |
| 2006/0068223 A1 | 3/2006 | Nariyuki et al. | |
| 2006/0134459 A1 | 6/2006 | Huo et al. | |
| 2006/0134464 A1 | 6/2006 | Nariyuki | |
| 2006/0194076 A1 | 8/2006 | Nariyuki | |
| 2006/0228577 A1 | 10/2006 | Nagara | |
| 2007/0048544 A1 | 3/2007 | Brown et al. | |

(56) References Cited

U.S. PATENT DOCUMENTS

| | | |
|---|---|---|
| 2007/0090756 A1 | 4/2007 | Okada et al. |
| 2007/0099026 A1 | 5/2007 | Lee et al. |
| 2007/0222374 A1 | 9/2007 | Egawa et al. |
| 2007/0244320 A1 | 10/2007 | Inoue et al. |
| 2007/0247829 A1 | 10/2007 | Fiedler et al. |
| 2008/0160345 A1 | 7/2008 | Inoue et al. |
| 2008/0217604 A1 | 9/2008 | Yokoyama et al. |
| 2008/0220287 A1 | 9/2008 | Dotz et al. |
| 2008/0286604 A1 | 11/2008 | Inoue et al. |
| 2009/0153035 A1 | 6/2009 | Shin et al. |
| 2009/0160323 A1 | 6/2009 | Nomura et al. |
| 2010/0051968 A1 | 3/2010 | Seo et al. |
| 2010/0052527 A1 | 3/2010 | Ikeda et al. |
| 2010/0145044 A1 | 6/2010 | Inoue et al. |
| 2010/0176718 A1 | 7/2010 | Jung et al. |
| 2010/0181553 A1 | 7/2010 | Miyazaki et al. |
| 2010/0184942 A1 | 7/2010 | Chen et al. |
| 2010/0276673 A1 | 11/2010 | Jung et al. |
| 2011/0001146 A1 | 1/2011 | Yamazaki et al. |
| 2011/0204353 A1 | 8/2011 | Yamazaki |
| 2011/0210316 A1 | 9/2011 | Kadoma et al. |
| 2011/0215714 A1 | 9/2011 | Seo et al. |
| 2011/0291083 A1 | 12/2011 | Kim et al. |
| 2012/0098417 A1 | 4/2012 | Inoue et al. |
| 2012/0205632 A1 | 8/2012 | Shitagaki et al. |
| 2012/0205687 A1 | 8/2012 | Yamazaki et al. |
| 2012/0206035 A1 | 8/2012 | Shitagaki et al. |
| 2012/0217486 A1 | 8/2012 | Takemura et al. |
| 2012/0217487 A1 | 8/2012 | Yamazaki et al. |
| 2012/0242219 A1 | 9/2012 | Seo et al. |
| 2012/0248421 A1 | 10/2012 | Yamazaki et al. |
| 2012/0256535 A1 | 10/2012 | Seo et al. |
| 2012/0267618 A1 | 10/2012 | Monkman et al. |
| 2013/0048964 A1 | 2/2013 | Takeda et al. |
| 2014/0008639 A1 | 1/2014 | Thompson et al. |
| 2015/0069352 A1 | 3/2015 | Kim et al. |
| 2015/0221879 A1 | 8/2015 | Inoue et al. |
| 2015/0221880 A1 | 8/2015 | Deaton et al. |
| 2016/0336521 A1 | 11/2016 | Inoue et al. |
| 2017/0179411 A1 | 6/2017 | Shitagaki et al. |

FOREIGN PATENT DOCUMENTS

| | | |
|---|---|---|
| CN | 001656853 A | 8/2005 |
| CN | 001773744 A | 5/2006 |
| CN | 101005122 A | 7/2007 |
| CN | 201084751 Y | 7/2008 |
| CN | 201114862 Y | 9/2008 |
| CN | 101442107 A | 5/2009 |
| CN | 101679467 A | 3/2010 |
| CN | 101679858 A | 3/2010 |
| CN | 102190653 A | 9/2011 |
| EP | 0669387 A | 8/1995 |
| EP | 1202608 A | 5/2002 |
| EP | 1359790 A | 11/2003 |
| EP | 1381096 A | 1/2004 |
| EP | 1388904 A | 2/2004 |
| EP | 1490914 A | 12/2004 |
| EP | 1656000 A | 5/2006 |
| EP | 1690866 A | 8/2006 |
| EP | 1729327 A | 12/2006 |
| EP | 1933395 A | 6/2008 |
| EP | 1953843 A | 8/2008 |
| EP | 2065950 A | 6/2009 |
| EP | 2270895 A | 1/2011 |
| EP | 2278637 A | 1/2011 |
| EP | 2306495 A | 4/2011 |
| EP | 2336143 A | 6/2011 |
| EP | 2363398 A | 9/2011 |
| EP | 2366753 A | 9/2011 |
| EP | 2911211 A | 8/2015 |
| EP | 3076759 A | 10/2016 |
| EP | 3321954 A | 5/2018 |
| EP | 3379591 A | 9/2018 |
| JP | 06-065569 A | 3/1994 |
| JP | 06-092947 A | 4/1994 |
| JP | 06-107648 A | 4/1994 |
| JP | 06-145658 A | 5/1994 |
| JP | 07-085972 A | 3/1995 |
| JP | 07-288184 A | 10/1995 |
| JP | 09-063770 A | 3/1997 |
| JP | 10-106748 A | 4/1998 |
| JP | 2000-133453 A | 5/2000 |
| JP | 2003-045676 A | 2/2003 |
| JP | 2003-347058 A | 12/2003 |
| JP | 2004-047469 A | 2/2004 |
| JP | 2004-095546 A | 3/2004 |
| JP | 2004-281274 A | 10/2004 |
| JP | 2005-514754 | 5/2005 |
| JP | 2005-344124 A | 12/2005 |
| JP | 2006-128636 A | 5/2006 |
| JP | 2006-203172 A | 8/2006 |
| JP | 2006-270053 A | 10/2006 |
| JP | 2007-001895 A | 1/2007 |
| JP | 2007-042875 A | 2/2007 |
| JP | 2007-073620 A | 3/2007 |
| JP | 2007-504272 | 3/2007 |
| JP | 2007-182429 A | 7/2007 |
| JP | 2008-509565 | 3/2008 |
| JP | 2008-077987 A | 4/2008 |
| JP | 2008-198801 A | 8/2008 |
| JP | 2008-244465 A | 10/2008 |
| JP | 2008-288344 A | 11/2008 |
| JP | 2009-001546 A | 1/2009 |
| JP | 2010-080435 A | 4/2010 |
| JP | 2010-135689 A | 6/2010 |
| JP | 2010-174035 A | 8/2010 |
| JP | 2011-081240 A | 4/2011 |
| JP | 2011-153269 A | 8/2011 |
| JP | 2011-201869 A | 10/2011 |
| JP | 2011-204673 A | 10/2011 |
| JP | 2011-216628 A | 10/2011 |
| JP | 2012-004526 A | 1/2012 |
| JP | 2012-186461 A | 9/2012 |
| JP | 2013-509670 | 3/2013 |
| JP | 5420692 | 2/2014 |
| KR | 2004-0014353 A | 2/2004 |
| KR | 2004-0019177 A | 3/2004 |
| KR | 2007-0042924 A | 4/2007 |
| KR | 2010-0027073 A | 3/2010 |
| KR | 2011-0099173 A | 9/2011 |
| KR | 2011-0099645 A | 9/2011 |
| KR | 10-1369603 | 3/2014 |
| TW | 200902681 | 1/2009 |
| TW | 200908412 | 2/2009 |
| TW | 201036956 | 10/2010 |
| TW | 201100523 | 1/2011 |
| TW | 201105638 | 2/2011 |
| TW | 201246649 | 11/2012 |
| TW | 201523963 | 6/2015 |
| TW | 201642504 | 12/2016 |
| TW | I573310 | 3/2017 |
| TW | 201733181 | 9/2017 |
| WO | WO-2000/016593 | 3/2000 |
| WO | WO-2000/057676 | 9/2000 |
| WO | WO-2000/070655 | 11/2000 |
| WO | WO-2001/041512 | 6/2001 |
| WO | WO-2003/007394 | 1/2003 |
| WO | WO-2003/059015 | 7/2003 |
| WO | WO-2003/083959 | 10/2003 |
| WO | WO-2004/101707 | 11/2004 |
| WO | WO-2005/022660 | 3/2005 |
| WO | WO-2006/033831 | 3/2006 |
| WO | WO-2006/033857 | 3/2006 |
| WO | WO-2007/027433 | 3/2007 |
| WO | WO-2007/052431 | 5/2007 |
| WO | WO-2007/064479 | 6/2007 |
| WO | WO-2007/066556 | 6/2007 |
| WO | WO-2007/108403 | 9/2007 |
| WO | WO-2008/105349 | 9/2008 |
| WO | WO-2008/143113 | 11/2008 |
| WO | WO-2008/156554 | 12/2008 |
| WO | WO-2010/061989 | 6/2010 |
| WO | WO-2010/085676 | 7/2010 |

(56) References Cited

FOREIGN PATENT DOCUMENTS

| WO | WO-2010/090925 | 8/2010 |
|---|---|---|
| WO | WO-2011/042443 | 4/2011 |
| WO | WO-2012/111579 | 8/2012 |

OTHER PUBLICATIONS

Seo.S et al., "Exciplex-triplet energy transfer: A new method to achieve extremely efficient organic light-emitting diode with external quantum efficiency over 30% and drive voltage below 3V", Jpn. J. Appl. Phys. (Japanese Journal of Applied Physics), Mar. 17, 2014, vol. 53, No. 4, pp. 042102-1-042102-8.

Song.W et al., "Light emission mechanism of mixed host organic light-emitting diodes", Appl. Phys. Lett. (Applied Physics Letters), Mar. 1, 2015, vol. 106, No. 12, pp. 123306-1-123306-4.

Tris[2-phenylpyridinato-C2,N]iridium(III), https://www.sigmaaldrich.com/catalog/product/aldrich/688096?lang=de&region=DE.

Organic Light-emitting Materials and Devices, 2007, pp. 330-334, Taylor & Francis Group.

Experimental data—absorption and emission spectrums of Alq3 and Ir(piq)3.

Rho.H et al., "Synthesis and Photophysical Studies of Iridium Complexes Having Different Ligands", Jpn. J. Appl. Phys. (Japanese Journal of Applied Physics), Jan. 20, 2006, vol. 45, No. 1B, pp. 568-573.

Negres.R et al., "Origin of efficient light emission from a phosphorescent polymer/organometallic guest-host system", Phys. Rev. B (Physical Review. B), Sep. 29, 2003, vol. 68, No. 11, pp. 115209-1-115209-8.

Gong.X et al., "High-Efficiency Polymer-Based Electrophosphorescent Devices", Adv. Mater. (Advanced Materials), Apr. 18, 2002, vol. 14, No. 8, pp. 581-585.

Hamed.Z et al., "Fluorescence quenching in PVK:ZnSe nanocomposite structure", Synthetic Metals, Jun. 12, 2014, vol. 195, pp. 102-109.

Notice of Opposition (Patent number. German U.S. Pat. No. 112012000828) dated Jun. 8, 2018.

Chinese Office Action (Application No. 201710762934.2) dated Jul. 30, 2018.

Suzuki.K et al., "Photophysical study of iridium complexes by absolute photoluminescence quantum yield measurements using an integrating sphere", Proceedings of SPIE, 2009, vol. 7415, pp. 741504-1-741504-8.

Itano.K et al., "Exciplex formation at the organic solid-state interface: Yellow emission in organic light-emitting diodes using green-fluorescent tris(8-quinolinolato)aluminum and hole-transporting molecular materials with low potentials", Appl. Phys. Lett. (Applied Physics Letters), Feb. 9, 1998, vol. 72, No. 6, pp. 636-638.

Baldo.M et al., "Very High-Efficiency Green Organic Light-Emitting Devices Based on Electrophosphorescence", Appl. Phys. Lett. (Applied Physics Letters), Jul. 5, 1999, vol. 75, No. 1, pp. 4-6.

Choong.V et al., "Organic Light-Emitting Diodes With a Bipolar Transport Layer", Appl. Phys. Lett. (Applied Physics Letters), Jul. 12, 1999, vol. 75, No. 2, pp. 172-174.

Kondakova.M et al., "High-efficiency, low-voltage phosphorescent organic light-emitting diode devices with mixed host", J. Appl. Phys. (Journal of Applied Physics), Nov. 4, 2008, vol. 104, pp. 094501-1-094501-17.

Seo.J et al., "Efficient blue-green organic light-emitting diodes based on heteroleptic tris-cyclometalated iridium(III) complexes", Thin Solid Films, Sep. 25, 2008, vol. 517, No. 5, pp. 1807-1810.

International Search Report (Application No. PCT/JP2012/053200) dated May 22, 2012.

Written Opinion (Application No. PCT/JP2012/053200) dated May 22, 2012.

Adachi.C et al., "Nearly 100% Internal Phosphorescence Efficiency in an Organic Light Emitting Device", J. Appl. Phys. (Journal of Applied Physics), Nov. 15, 2001, vol. 90, No. 10, pp. 5048-5051.

Markham.J et al., "High-efficiency green phosphorescence from spin-coated single-layer dendrimer light-emitting diodes", Appl. Phys. Lett. (Applied Physics Letters), Apr. 15, 2002, vol. 80, No. 15, pp. 2645-2647.

Fujita.M et al., "Reduction of operating voltage in organic light-emitting diode by corrugated photonic crystal structure", Appl. Phys. Lett. (Applied Physics Letters), Dec. 6, 2004, vol. 85, No. 23, pp. 5769-5771.

Baldo.M et al., "Prospects for Electrically Pumped Organic Lasers", Phys. Rev. B (Physical Review. B), Jul. 19, 2002, vol. 66, pp. 035321-1-035321-16.

Gu.G et al., "Transparent Organic Light Emitting Devices", Appl. Phys. Lett. (Applied Physics Letters), May 6, 1996, vol. 68, No. 19, pp. 2606-2608.

Baldo.M et al., "Highly Efficient Phosphorescent Emission From Organic Electroluminescent Devices", Nature, Sep. 10, 1998, vol. 395, pp. 151-154.

King.K et al., "Excited-state properties of a triply ortho-metalated iridium(III) complex", J. Am. Chem. Soc. (Journal of the American Chemical Society), Mar. 1, 1985, vol. 107, No. 5, pp. 1431-1432, ACS(American Chemical Society).

Hino.Y et al., "Red Phosphorescent Organic Light-Emitting Diodes Using Mixture System of Small-Molecule and Polymer Host", Jpn. J. Appl. Phys. (Japanese Journal of Applied Physics), Apr. 21, 2005, vol. 44, No. 4B, pp. 2790-2794.

Tsuboyama.A et al., "Homoleptic Cyclometalated Iridium Complexes with Highly Efficient Red Phosphorescence and Application to Organic Light-Emitting Diode", J. Am. Chem. Soc. (Journal of the American Chemical Society), 2003, vol. 125, No. 42, pp. 12971-12979.

Decision to Grant a Patent dated Oct. 29, 2013 for Japanese Patent application No. 2012-029033.

Written Amendment dated Aug. 8, 2013 for Japanese Paten application No. 2012-029033.

Chinese Office Action (Application No. 201280002425.5) dated Apr. 21, 2015.

Taiwanese Office Action (Application No. 103140461) dated Apr. 6, 2016.

Gong.X et al., "Phosphorescence from iridium complexes doped into polymer blends", J. Appl. Phys. (Journal of Applied Physics), Feb. 1, 2004, vol. 95, No. 3, pp. 948-953.

German Office Action (Application No. 112012000828.6) dated Oct. 26, 2016.

Lee.J et al., "Stabilizing the efficiency of phosphorescent organic light-emitting diodes", SPIE Newsroom, Apr. 21, 2008, pp. 1-3.

Taiwanese Office Action (Application No. 105126231) dated Nov. 30, 2016.

Chinese Office Action (Application No. 201610428799.3) dated Apr. 28, 2017.

Chinese Office Action (Application No. 201610428538.1) dated May 3, 2017.

Yersin.H et al., Highly Efficient OLEDs with Phosphorescent Materials, 2008, pp. 1-97,283-309.

Tokito.S et al., "Improvement in performance by doping", Organic EL Display, Aug. 20, 2004, pp. 67-99, Ohmsha.

Jeon.W et al., "Ideal host and guest system in phosphorescent OLED5", Organic Electronics, 2009, vol. 10, pp. 240-246, Elsevier.

Su.S et al., "RGB Phosphorescent Organic Light-Emitting Diodes by Using Host Materials with Heterocyclic Cores:Effect of Nitrogen Atom Orientations", Chem. Mater. (Chemistry of Materials), 2011, vol. 23, No. 2, pp. 274-284.

Rausch.A et al., "Matrix Effects on the Triplet State of the OLED Emitter Ir(4,6-dFppy)2(pic)(FIrpic):Investigations by High-Resolution Optical Spectroscopy", Inorg. Chem. (Inorganic Chemistry), 2009, vol. 48, No. 5, pp. 1928-1937.

Zhao.Q et al., "Synthesis and Photophysical, Electrochemical, and Electrophosphorescent Properties of a Series of Iridium(III) Complexes Based on Quinoline Derivatives and Different β-Diketonate Ligands", Organometallics, Jun. 14, 2006, vol. 25, No. 15, pp. 3631-3638.

Chen.F et al., "Triplet Exciton Confinement in Phosphorescent Polymer Light-Emitting Diodes", Appl. Phys. Lett. (Applied Physics Letters), Feb. 17, 2003, vol. 82, No. 7, pp. 1006-1008.

(56) References Cited

OTHER PUBLICATIONS

Tokito.S et al., "Confinement of Triplet Energy on Phosphorescent Molecules for Highly-Efficient Organic Blue-Light-Emitting Devices", Appl. Phys. Lett. (Applied Physics Letters), Jul. 21, 2003, vol. 83, No. 3, pp. 569-571.
Endo.A et al., "Efficient Up-Conversion of Triplet Excitons Into a Singlet State and its Application for Organic Light Emitting Diodes", Appl. Phys. Lett. (Applied Physics Letters), Feb. 24, 2011, vol. 98, No. 8, pp. 083302-1-083302-3.
Park.Y et al., "Efficient triplet harvesting by fluorescent molecules through exciplexes for high efficiency organic light-emitting diodes", Appl. Phys. Lett. (Applied Physics Letters), Apr. 18, 2013, vol. 102, No. 15, pp. 153306-1-153306-5.
Taiwanese Office Action (Application No. 106116893) dated May 15, 2018.
Ko.L et al., "Multi-layer organic light-emitting diodes processed from solution using phosphorescent dendrimers in a polymer host", Organic Electronics, Mar. 20, 2010, vol. 11, No. 6, pp. 1005-1009.
Korean Office Action (Application No. 2013-7014009) dated Jun. 15, 2018.
Korean Office Action (Application No. 2018-7000007) dated Jun. 15, 2018.
Korean Office Action (Application No. 2018-7004943) dated Jun. 15, 2018.
Seo.J et al., "Efficient blue phosphorescent organic light-emitting diodes by tuning iridium(III) phenylpyridine complexes", Journal of Nanoscience and Nanotechnology, 2009, vol. 9, No. 12, pp. 7048-7051, United States of America.
Holzer.W et al., "Absorption and emission spectroscopic characterization of Ir(ppy)3", Chemical Physics, 2005, vol. 308, No. 1-2, pp. 93-102.
Tamayo.A et al., "Synthesis and Characterization of Facial and Meridional Tris-cyclometalated Iridium (III) Complexes", J. Am. Chem. Soc. (Journal of the American Chemical Society), Jun. 18, 2003, vol. 125, No. 24, pp. 7377-7387.
Okada.S et al., "Substituent effects of iridium complexes for highly efficient red OLEDs", Dalton Transactions, May 5, 2005, No. 9, pp. 1583-1590.
Notice of Opposition (Patent number. German Patent No. 112012000831) dated Jun. 4, 2018.
Notice of Opposition (Patent number. German Patent No. 112012001364) dated Jun. 27, 2018.
Petition for Cancellation of Patent (Patent number. Korean Patent No. 10-1793880-00-00) dated May 24, 2018.
Petition for Cancellation of Patent (Patent number. Korean Patent No. 10-1812673-00-00) dated Jul. 6, 2018.
Written Opposition to the Grant of Patent (Patent number. Japanese Patent No. 5981726) dated Feb. 28, 2017.
Liu.Z et al., "Highly efficient, orange?red organic light-emitting diodes using a series of green-emission iridium complexes as hosts", Organic Electronics, Dec. 6, 2008, vol. 10, No. 2, pp. 247-255.
Lee.S et al., "Synthesis and Characterization of Red-Emitting Iridium(III) Complexes for Solution-Processable Phosphorescent Organic Light-Emitting Diodes", Adv. Funct. Mater. (Advanced Functional Materials), Jul. 1, 2009, vol. 19, No. 14, pp. 2205-2212.
Jiang.X et al., "Red-emitting electroluminescent devices based on osmium-complexes-doped blend of poly(vinylnaphthalene) and 1,3,4-oxadiazole derivative", Appl. Phys. Lett. (Applied Physics Letters), Oct. 15, 2002, vol. 81, No. 17, pp. 3125-3127.
Yang.X et al., "Highly Efficient Single-Layer Polymer Electrophosphorescent Devices", Adv. Mater. (Advanced Materials), 2004, vol. 16, No. 2, pp. 161-166.
Yang.X et al., "Polymer electrophosphorescence devices with high power conversion efficiencies", Appl. Phys. Lett. (Applied Physics Letters), Apr. 1, 2004, vol. 84, No. 14, pp. 2476-2478.
Shimizu.T et al., "Highly Efficient and Stable Phosphorescent Organic Light-Emitting Diodes Utilizing Reverse Intersystem Crossing of the Host Material", Adv. Optical Mater. (Advanced Opticeal Materials), Aug. 4, 2014, vol. 2, No. 11, pp. 1070-1075.
Cocchi.M et al., "Efficient exciplex emitting organic electroluminescent devices", Appl. Phys. Lett. (Applied Physics Letters), Mar. 26, 2002, vol. 80, No. 13, pp. 2401-2403.
Goushi.K et al., "Organic light-emitting diodes employing efficient reverse intersystem crossing for triplet-to-singlet state conversion", Nature Photonics, Mar. 11, 2012, vol. 6, pp. 253-258.
Hay.P, "Theoretical Studies of the Ground and Excited Electronic States in Cyclometalated Phenylpyridine Ir(III) Complexes Using Density Functional Theory", The Journal of Physical Chemistry A, Jan. 29, 2002, vol. 106, No. 8, pp. 1634-1641.
Tsuboi.T et al., "Optical characteristics of PtOEP and Ir(ppy)3 triplet-exciton materials for organic electroluminescence devices", Thin Solid Films, Aug. 1, 2003, vol. 438-439, pp. 301-307.
Baek.H et al., "Efficient co-host exciplex emission for white organic light-emitting diodes", J. Phys. Chem. Solids (Journal of Physics and Chemistry of Solids), Aug. 1, 2018, vol. 119, pp. 276-280.
Zhang.D et al., "Exciplex emission and Auger process assistant green organic electrophosphorescence devices with very low doped level of iridium complex", J. Phys. D: Appl. Phys. (Journal of Physics D: Applied Physics), Nov. 25, 2008, vol. 41, No. 24, pp. 245102-1-245102-4.
Sun.D et al., "Efficient triplet utilization in conventional solution-processed phosphorescent organic light emitting diodes using a thermal activated delayed fluorescence polymer as an assistant host", J. Mater. Chem. C(Journal of Materials Chemistry C), Apr. 6, 2018, vol. 6, pp. 4800-4806.
Lamansky.S et al., "Highly Phosphorescent Bis-Cyclometalated Iridium Complexes: Synthesis, Photophysical Characterization, and Use in Organic Light Emitting Diodes", J. Am. Chem. Soc. (Journal of the American Chemical Society), Apr. 13, 2001, vol. 123, No. 18, 4304-4312.
Lo.S et al., "Synthesis and Properties of Highly Efficient Electroluminescent Green Phosphorescent Iridium Cored Dendrimers", Macromolecules, 2003, vol. 36, No. 26, pp. 9721-9730, American Chemical Society.
Zhou.X et al., "Very-low-operating-voltage organic light-emitting diodes using a p-doped amorphous hole injection layer", Appl. Phys. Lett. (Applied Physics Letters), Jan. 22, 2001, vol. 78, No. 4, pp. 410-412.
Hedley.G et al., "Ultrafast luminescence in Ir(ppy)3", Chem. Phys. Lett. (Chemical Physics Letters), 2008, vol. 450, pp. 292-296.
Turnbull.G et al., "Rigidly linking cyclometallated Ir(111) and Pt(II) centres: an efficient approach to strongly absorbing and highly phosphorescent red emitters", Chemical Communications, 2017, vol. 53, pp. 2729-2732, Royal Society of Chemistry.
Tris[2-(4,6-difluorophenyl)pyridinato-C,N]iridium(III), https://www.sigmaaldrich.com/content/dam/sigma-aldrich/docs/Aldrich/Bulletin/al_uv-vis_682594.pdf#search=%27Tris%5B2%284%2C6difluorophenyl%29pyridinatoC%2CN%5Diridium%28III%29%27.
Korean Office Action (Application No. 2018-7000007) dated May 23, 2019.
Jeon.S et al., "100% internal quantum efficiency and stable efficiency roll-off in phosphorescent light-emitting diodes using a high triplet energy hole transport material", Appl. Phys. Lett. (Applied Physics Letters), Jun. 17, 2008, vol. 93, pp. 063306-1-063306-3.
Finkenzeller.W et al., "Triplet State Properties of the OLED Emitter Ir(btp)2(acac): Characterization by Site-Selective Spectroscopy and Application of High Magnetic Fields", Inorg. Chem. (Inorganic Chemistry), May 9, 2007, vol. 46, No. 12, pp. 5076-5083.
Indian Office Action (Application No. 07788/DELNP/2013) dated Jul. 5, 2019.
Wang.Q et al., "Harvesting Excitons Via Two Parallel Channels for Efficient White Organic LEDs with Nearly 100% lnternal Quantum Efficiency: Fabrication and Emission-Mechanism Analysis", Adv. Funct. Mater. (Advanced Functional Materials), 2009, vol. 19, No. 1. pp. 84-95.
Taiwanese Office Action (Application No. 108109613) dated Sep. 26, 2019.

* cited by examiner

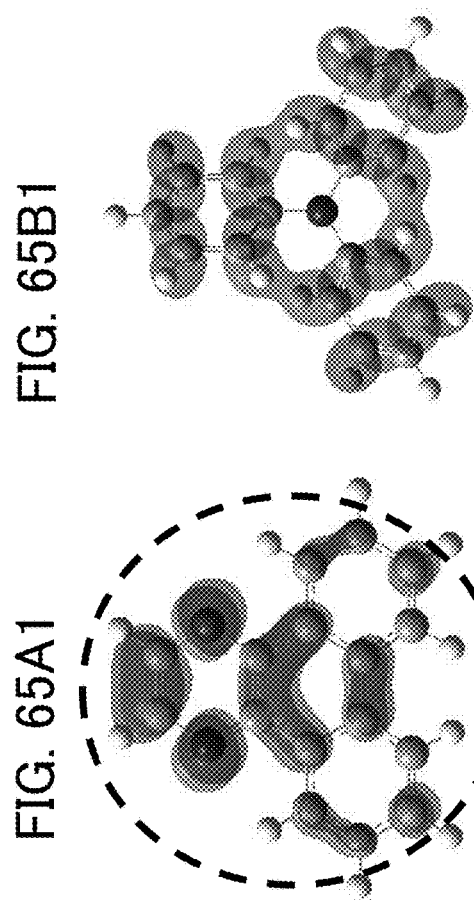
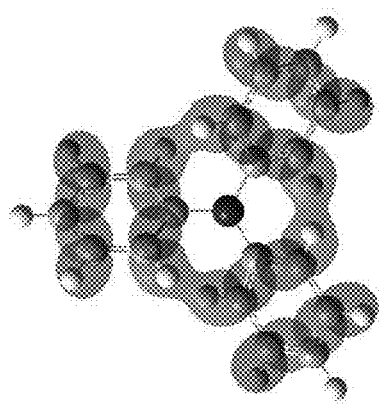
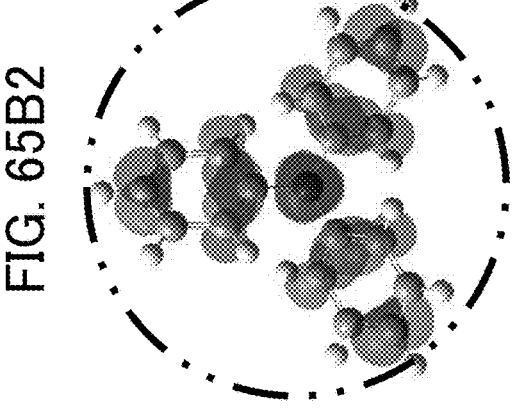
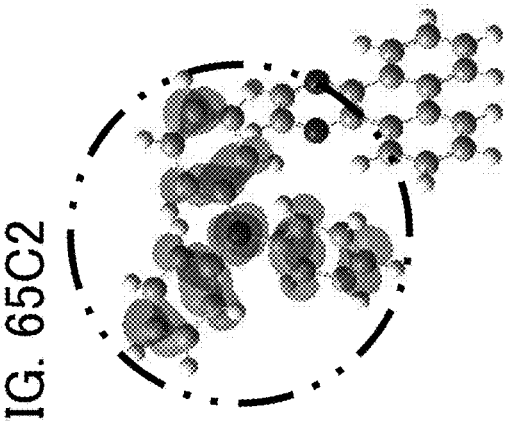
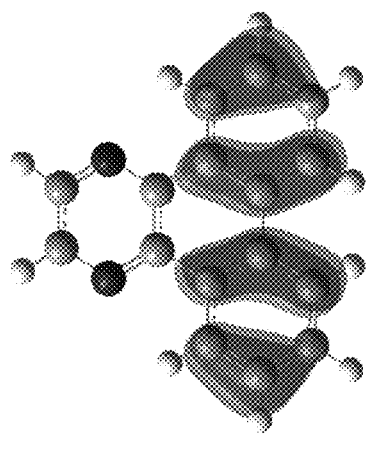
FIG. 65A1  FIG. 65B1  FIG. 65C1
FIG. 65A2  FIG. 65B2  FIG. 65C2

LIGHT-EMITTING ELEMENT

TECHNICAL FIELD

The present invention relates to light-emitting elements using an organic electroluminescence (EL) phenomenon (hereinafter such light-emitting elements are also referred to as organic EL elements).

BACKGROUND ART

An organic EL element has been actively researched and developed. In a fundamental structure of the organic EL element, a layer including a luminescent organic compound (hereinafter also referred to as light-emitting layer) is interposed between a pair of electrodes. The organic EL element has attracted attention as a next-generation flat panel display element owing to characteristics such as feasibility of being thinner and lighter, high speed response to input signals, and capability of direct current low voltage driving. In addition, a display using such a light-emitting element has a feature that it is excellent in contrast and image quality, and has a wide viewing angle. Further, being a planar light source, the organic EL element has been attempted to be applied as a light source such as a backlight of a liquid crystal display and a lighting device.

The emission mechanism of the organic EL element is of a carrier-injection type. That is, by application of voltage with a light-emitting layer interposed between electrodes, electrons and holes injected from the electrodes are recombined to make a light-emitting substance excited, and light is emitted when the excited state relaxes to the ground state. There can be two types of the excited states: a singlet excited state ($S^*$) and a triplet excited state ($T^*$). The statistical generation ratio of the excited states in a light-emitting element is considered to be $S^*:T^*=1:3$.

In general, the ground state of a light-emitting organic compound is a singlet state. Therefore, light emission from the singlet excited state ($S^*$) is referred to as fluorescence because it is caused by electron transition between the same spin multiplicities. On the other hand, light emission from the triplet excited state ($T^*$) is referred to as phosphorescence where electron transition occurs between different spin multiplicities. Here, in a compound emitting fluorescence (hereinafter referred to as fluorescent compound), in general, phosphorescence is not observed at room temperature, and only fluorescence is observed. Accordingly, the internal quantum efficiency (the ratio of generated photons to injected carriers) in a light-emitting element including a fluorescent compound is assumed to have a theoretical limit of 25% based on $S^*:T^*=1:3$.

On the other hand, when a compound emitting phosphorescence (hereinafter referred to as phosphorescent compound) is used, an internal quantum efficiency of 100% can be theoretically achieved. That is, higher emission efficiency can be obtained than using a fluorescent compound. For these reasons, a light-emitting element including a phosphorescent compound has been actively developed in recent years in order to achieve a high-efficiency light-emitting element. As the phosphorescent compound, an organometallic complex that has iridium or the like as a central metal has particularly attracted attention owing to their high phosphorescence quantum yield; for example, an organometallic complex that has iridium as a central metal is disclosed as a phosphorescent material in Patent Document 1.

When a light-emitting layer of a light-emitting element is formed using a phosphorescent compound described above, in order to suppress concentration quenching or quenching due to triplet-triplet annihilation in the phosphorescent compound, the light-emitting layer is often formed such that the phosphorescent compound is dispersed in a matrix of another compound. Here, the compound serving as the matrix is called host material, and the compound dispersed in the matrix, such as a phosphorescent compound, is called guest material.

REFERENCE

Patent Document

[Patent Document 1] PCT International Publication No. 00/70655

DISCLOSURE OF INVENTION

However, it is generally said that the light extraction efficiency of an organic EL element is approximately 20% to 30%. Accordingly, considering light absorption by a reflective electrode and a transparent electrode, the external quantum efficiency of a light-emitting element including a phosphorescent compound has a limit of approximately 25% at most.

An object of one embodiment of the present invention is to provide a light-emitting element with high external quantum efficiency. Another object of one embodiment of the present invention is to provide a light-emitting element having a long lifetime.

One embodiment of the present invention is a light-emitting element which includes a light-emitting layer containing a phosphorescent compound, a first organic compound, and a second organic compound between a pair of electrodes, in which a combination of the first organic compound and the second organic compound forms an exciplex.

Another embodiment of the present invention is a light-emitting element which includes a light-emitting layer containing a phosphorescent compound, a first organic compound, and a second organic compound between a pair of electrodes, in which a combination of the first organic compound and the second organic compound forms an exciplex, and the exciplex acts on the phosphorescent compound so that the phosphorescent compound emits phosphorescence.

Another embodiment of the present invention is a light-emitting element which includes a light-emitting layer containing a phosphorescent compound, a first organic compound, and a second organic compound between a pair of electrodes, in which an exciplex is formed from a singlet exciton of the first organic compound.

Another embodiment of the present invention is a light-emitting element which includes a light-emitting layer containing a phosphorescent compound, a first organic compound, and a second organic compound between a pair of electrodes, in which an exciplex is formed from an anion of the first organic compound and a cation of the second organic compound.

In the aforementioned light-emitting element, it is preferable that excitation energy of the exciplex be transferred to the phosphorescent compound so that the phosphorescent compound emits phosphorescence.

In the aforementioned light-emitting element, it is preferable that at least one of the first organic compound and the second organic compound be a fluorescent compound.

In the aforementioned light-emitting element, it is preferable that the phosphorescent compound be an organometallic complex.

The light-emitting element of one embodiment of the present invention can be applied to a light-emitting device, an electronic device, and a lighting device.

According to one embodiment of the present invention, a light-emitting element having high external quantum efficiency can be provided. According to another embodiment of the present invention, a light-emitting element having a long lifetime can be provided.

BRIEF DESCRIPTION OF DRAWINGS

FIGS. 65(A1), 65(A2), 65(B1), 65(B2), 65(C1), and 65(C2) show calculation results according to one embodiment of the present invention.

BEST MODE FOR CARRYING OUT THE INVENTION

Figure 1A:
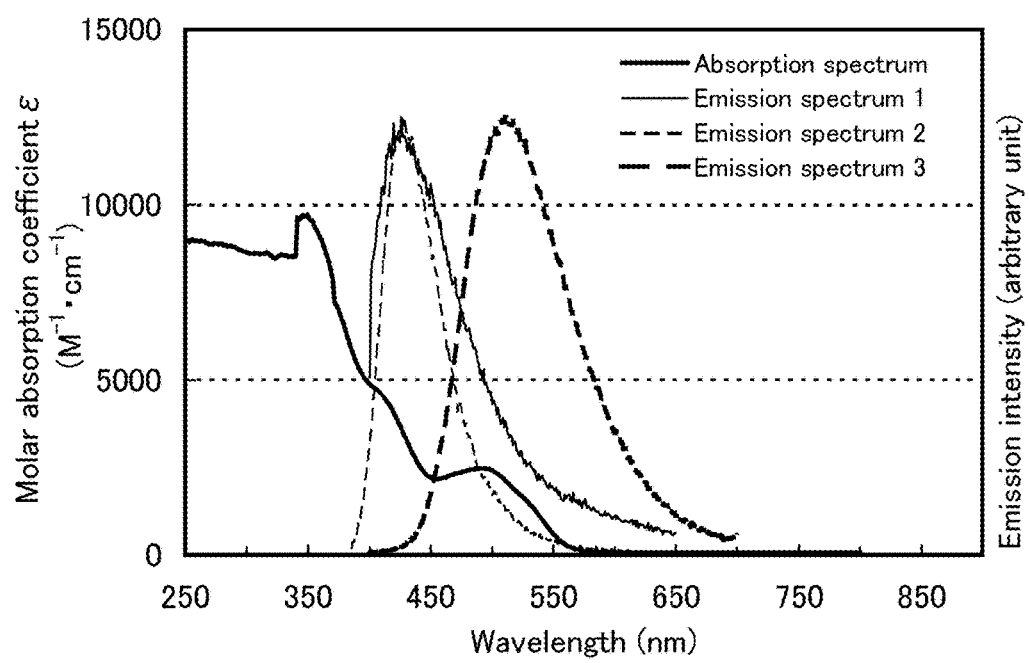
FIGS. 1A and 1B each show an absorption spectrum and emission spectra according to Example 1.

Embodiments will be described with reference to drawings. Note that the invention is not limited to the following description, and it will be easily understood by those skilled in the art that various changes and modifications can be made without departing from the spirit and scope of the invention. Therefore, the invention should not be construed as being limited to the description in the following embodiments. Note that in the structures of the invention described below, the same portions or portions having similar functions are denoted by the same reference numerals in different drawings, and description of such portions is not repeated.

(Embodiment 1)

In this embodiment, a light-emitting element of one embodiment of the present invention will be described.

The light-emitting element of this embodiment includes a light-emitting layer containing a guest material as a light-emitting substance, a first organic compound, and a second organic compound. Specifically, a phosphorescent compound is used as the guest material. Note that one of the first and second organic compounds, the content of which is higher than that of the other in the light-emitting layer, is called host material.

The structure in which the guest material is dispersed in the host material can prevent the light-emitting layer from crystallizing. Further, it is possible to suppress concentration quenching due to high concentration of the guest material, and thus the light-emitting element can have higher emission efficiency.

Note that in this embodiment, it is preferable that the level of a triplet excitation energy ($T_1$ level) of each of the first and second organic compounds be higher than that of the guest material. This is because, when the $T_1$ level of the first organic compound (or the second organic compound) is lower than that of the guest material, the triplet excitation energy of the guest material, which is to contribute to light emission, is quenched by the first organic compound (or the second organic compound) and accordingly the emission efficiency is decreased.

<Elementary Processes of Light Emission>

First, a description is given of general elementary processes of light emission in a light-emitting element using a phosphorescent compound as a guest material.

(1) The case where an electron and a hole are recombined in a guest molecule, and the guest molecule is excited (direct recombination process).

(1-1) When the excited state of the guest molecule is a triplet excited state, the guest molecule emits phosphorescence.

(1-2) When the excited state of the guest molecule is a singlet excited state, the guest molecule in the singlet excited state undergoes intersystem crossing to a triplet excited state and emits phosphorescence.

In other words, in the direct recombination process in (1), as long as the efficiency of intersystem crossing and the phosphorescence quantum yield of the guest molecule are high, high emission efficiency can be obtained. Note that as described above, the $T_1$ level of the host molecule is preferably higher than the $T_1$ level of the guest molecule.

(2) The case where an electron and a hole are recombined in a host molecule and the host molecule is put in an excited state (energy transfer process).

(2-1) When the excited state of the host molecule is a triplet excited state and the $T_1$ level of the host molecule is higher than that of the guest molecule, excitation energy is transferred from the host molecule to the guest molecule, and thus the guest molecule is put in a triplet excited state. The guest molecule in the triplet excited state emits phosphorescence. Note that energy transfer to a singlet excitation energy level ($S_1$ level) of the guest molecule can occur in theory, but is unlikely to be a main energy transfer process because, in many cases, the $S_1$ level of the guest molecule has a higher energy than the $T_1$ level of the host molecule; therefore, a description thereof is not given here.

(2-2) When the excited state of the host molecule is a singlet excited state and the $S_1$ level of the host molecule is higher than the $S_1$ level and $T_1$ level of the guest molecule, excitation energy is transferred from the host molecule to the guest molecule, and thus, the guest molecule is put in a singlet excited state or a triplet excited state. The guest molecule in the triplet excited state emits phosphorescence. In addition, the guest molecule in the singlet excited state undergoes intersystem crossing to a triplet excited state, and emits phosphorescence.

In other words, in the energy transfer process in (2), it is important how efficiently both the triplet excitation energy and the singlet excitation energy of the host molecule can transfer to the guest molecule.

In view of the above-described energy transfer processes, before the excitation energy of the host molecule is transferred to the guest molecule, when the host molecule itself is deactivated by emitting the excitation energy as light or heat, the emission efficiency is decreased. The inventors have found out that when the host molecule is in a singlet excited state (the above (2-2)), the energy is unlikely to transfer to the guest molecule, i.e., the phosphorescent compound, and the emission efficiency is likely to be decreased as compared to when the host molecule is in a triplet excited state (the above (2-1)). Thus, the inventors have focused on that fact as an object. The reason has been found as follows in consideration of a more detailed energy transfer process.

<Energy Transfer Process>

The following describes energy transfer processes between molecules in detail.

First, as a mechanism of energy transfer between molecules, the following two mechanisms are proposed. A molecule providing excitation energy is referred to as host molecule, while a molecule receiving the excitation energy is referred to as guest molecule.

«Förster Mechanism (Dipole-Dipole Interaction)»

In Förster mechanism (also referred to as Förster resonance energy transfer), direct intermolecular contact is not necessary for energy transfer. Through a resonant phenomenon of dipolar oscillation between a host molecule and a guest molecule, energy transfer occurs. By the resonant phenomenon of dipolar oscillation, the host molecule provides energy to the guest molecule, and thus, the host molecule is put in a ground state and the guest molecule is put in an excited state. The rate constant $k_{h^* \to g}$ of Förster mechanism is expressed by Formula (1).

[Formula (1)]

$$k_{h^* \to g} = \frac{9000 c^4 K^2 \phi \ln 10}{128 \pi^5 n^4 N \tau R^6} \int \frac{f'_h(v) \varepsilon_g(v)}{v^4} dv \quad (1)$$

In Formula (1), $v$ denotes a frequency, $f'_h(v)$ denotes a normalized emission spectrum of a host molecule (a fluorescent spectrum in energy transfer from a singlet excited state, and a phosphorescent spectrum in energy transfer from a triplet excited state), $\varepsilon_g(v)$ denotes a molar absorption coefficient of a guest molecule, N denotes Avogadro's number, n denotes a refractive index of a medium, R denotes an intermolecular distance between the host molecule and the guest molecule, $\tau$ denotes a measured lifetime of an excited state (fluorescence lifetime or phosphorescence lifetime), c denotes the speed of light, $\phi$ denotes a luminescence quantum yield (a fluorescence quantum yield in energy transfer from a singlet excited state, and a phosphorescence quantum yield in energy transfer from a triplet excited state), and $K^2$ denotes a coefficient (0 to 4) of orientation of a transition dipole moment between the host molecule and the guest molecule. Note that $K^2 = 2/3$ in random orientation.

«Dexter Mechanism (Electron Exchange Interaction)»

In Dexter mechanism (also referred to as Dexter electron transfer), a host molecule and a guest molecule are close to a contact effective range where their orbitals overlap, and the host molecule in an excited state and the guest molecule in a ground state exchange their electrons, which leads to energy transfer. The rate constant $k_{h^* \to g}$ of Dexter mechanism is expressed by Formula (2).

[Formula (2)]

$$k_{h^* \to g} = \left(\frac{2\pi}{h}\right) K^2 \exp\left(-\frac{2R}{L}\right) \int f'_h(v) \varepsilon'_g(v) dv \quad (2)$$

In Formula (2), h denotes a Planck constant, K denotes a constant having an energy dimension, $v$ denotes a frequency, $f'_h(v)$ denotes a normalized emission spectrum of a host molecule (a fluorescent spectrum in energy transfer from a singlet excited state, and a phosphorescent spectrum in energy transfer from a triplet excited state), $\varepsilon'_g(v)$ denotes a normalized absorption spectrum of a guest molecule, L denotes an effective molecular radius, and R denotes an intermolecular distance between the host molecule and the guest molecule.

Here, the efficiency of energy transfer from the host molecule to the guest molecule (energy transfer efficiency $\Phi_{ET}$) is thought to be expressed by Formula (3). In the formula, $k_r$ denotes a rate constant of a light-emission process (fluorescence in energy transfer from a singlet excited state, and phosphorescence in energy transfer from a triplet excited state) of a host molecule, $k_n$ denotes a rate constant of a non-light-emission process (thermal deactivation or intersystem crossing) of a host molecule, and $\tau$ denotes a measured lifetime of an excited state of a host molecule.

[Formula (3)]

$$\Phi_{ET} = \frac{k_{h^* \to g}}{k_r + k_n + k_{h^* \to g}} = \frac{k_{h^* \to g}}{\left(\frac{1}{\tau}\right) + k_{h^* \to g}} \quad (3)$$

First, according to Formula (3), it is found that the energy transfer efficiency $\Phi_{ET}$ can be increased by further increasing the rate constant $k_{h^* \to g}$ of energy transfer as compared with another competing rate constant $k_r + k_n$ ($= 1/\tau$). Then, in order to increase the rate constant $k_{h^* \to g}$ of energy transfer, based on Formulae (1) and (2), in Förster mechanism and Dexter mechanism, it is preferable that an emission spectrum of a host molecule (a fluorescent spectrum in energy transfer from a singlet excited state, and a phosphorescent spectrum in energy transfer from a triplet excited state) largely overlap with an absorption spectrum of a guest molecule.

Here, the present inventors have considered that the absorption band on the longest wavelength side (lowest energy side) in the absorption spectrum of the guest molecule is important in considering the overlap between the emission spectrum of the host molecule and the absorption spectrum of the guest molecule.

In this embodiment, a phosphorescent compound is used as the guest material. In an absorption spectrum of the phosphorescent compound, an absorption band that is considered to contribute to light emission most greatly is an absorption wavelength corresponding to direct transition from a singlet ground state to a triplet excitation state and a vicinity of the absorption wavelength, which is on the longest wavelength side. Therefore, it is considered preferable that the emission spectrum (a fluorescent spectrum and a phosphorescent spectrum) of the host material overlap with the absorption band on the longest wavelength side in the absorption spectrum of the phosphorescent compound.

For example, most organometallic complexes, especially light-emitting iridium complexes, have a broad absorption band at around 500 nm to 600 nm as the absorption band on the longest wavelength side (as a matter of fact, the broad absorption band can be on a shorter or longer wavelength side depending on emission wavelengths). This absorption band is mainly based on a triplet MLCT (metal to ligand charge transfer) transition. Note that it is considered that the absorption band also includes absorptions based on a triplet $\pi$-$\pi^*$ transition and a singlet MLCT transition, and that these absorptions overlap each another to form a broad absorption band on the longest wavelength side in the absorption spectrum. In other words, the difference between the lowest singlet excited state and the lowest triplet excited state is small, and absorptions based on these states overlap each other to form a broad absorption band on the longest wavelength side in the absorption spectrum. Therefore, as described above, it is preferable that the broad absorption band on the longest wavelength side largely overlap with the emission spectrum of the host material when an organometallic complex (especially iridium complex) is used as the guest material.

Here, first, energy transfer from a host material in a triplet excited state will be considered. From the above-described discussion, it is preferable that, in energy transfer from a triplet excited state, the phosphorescent spectrum of the host material and the absorption band on the longest wavelength side of the guest material largely overlap each other.

Note that a fluorescent compound is generally used as the host material; thus, phosphorescence lifetime ($\tau$) is a millisecond or longer which is extremely long (i.e., $k_r+k_n$ is low). This is because the transition from the triplet excited state to the ground state (singlet) is a forbidden transition. Formula (3) shows that this is favorable to energy transfer efficiency $\Phi_{ET}$. This also suggests that energy is generally likely to be transferred from the host material in the triplet excited state to the guest material in the triplet excited state.

However, a question here is energy transfer from the host material in the singlet excited state. In order to efficiently perform not only energy transfer from the triplet excited state but also energy transfer from the singlet excited state, it is clear from the above-described discussion that the host material needs to be designed so as to have not only its phosphorescent spectrum but also its fluorescent spectrum overlapping with the absorption band on the longest wavelength side of the guest material. In other words, unless the host material is designed so as to have its fluorescent spectrum in a position similar to that of its phosphorescent spectrum, it is not possible to achieve efficient energy transfer from the host material in both the singlet excited state and the triplet excited state.

However, the $S_1$ level generally differs greatly from the $T_1$ level ($S_1$ level>$T_1$ level); therefore, the fluorescence emission wavelength also differs greatly from the phosphorescence emission wavelength (fluorescence emission wavelength<phosphorescence emission wavelength). For example, 4,4'-di(N-carbazolyl)biphenyl (abbreviation: CBP), which is commonly used as a host material in a light-emitting element including a phosphorescent compound, has a phosphorescent spectrum at around 500 nm and has a fluorescent spectrum at around 400 nm, which are largely different by about 100 nm. This example also shows that it is extremely difficult to design a host material so as to have its fluorescent spectrum in a position similar to that of its phosphorescent spectrum. Therefore, the present inventors consider it a major challenge to improve efficiency in energy transfer from the host material in the singlet excited state to the guest material.

Note that fluorescence lifetime ($\tau$) of a fluorescent compound that is used as the host material is on the order of nanoseconds which is extremely short (i.e., $k_r+k_n$ is high). This is because the transition from the singlet excited state to the ground state (singlet) is an allowed transition. Formula (3) shows that this is unfavorable to energy transfer efficiency $\Phi_{ET}$. This also suggests that energy is generally unlikely to be transferred from the host material in the singlet excited state to the guest material.

One embodiment of the present invention is a useful technique which can overcome such a problem of the efficiency of the energy transfer from the host material in the singlet excited state to the guest material.

Note that it has been considered so far that a light-emitting element including a phosphorescent compound can theoretically achieve an internal quantum efficiency of 100% because intersystem crossing makes it possible to convert both the single excited state and the triplet excited state into light emission (refer to "(1) direct recombination process" described above). In addition, it has been discussed that a light-emitting element having an external quantum efficiency as high as 20% under the assumption that the light extraction efficiency is 20% achieved an internal quantum efficiency of substantially 100%. However, it is considered in fact that these conventional light-emitting elements have not achieved an internal quantum efficiency of 100% because the above-described energy transfer from the singlet excited state of the host material has been overlooked. This is based on the fact that the present inventors have achieved an external quantum efficiency of 30% by carrying out an embodiment of the present invention which is described below. In other words, an external quantum efficiency of at least 30% corresponds to an internal quantum efficiency of 100%, and one embodiment of the present invention is a useful technique for achieving it. Note that this indicates that a conventional external quantum efficiency of 20% can be estimated to correspond to an internal quantum efficiency of 70% or less.

<One Embodiment of Present Invention>

One embodiment of the present invention is a light-emitting element which includes a light-emitting layer containing a phosphorescent compound, a first organic compound, and a second organic compound between a pair of electrodes, in which a combination of the first organic compound and the second organic compound forms an exciplex.

The first organic compound and the second organic compound form an exciplex (also referred to as excited complex) through carrier recombination (or from a singlet exciton). In the case where the exciplex formed emits light, the emission wavelength thereof is located on the longer wavelength side with respect to the emission wavelength (fluorescent wavelength) of each of the first and second organic compounds. In other words, by formation of the exciplex, the fluorescent spectrum of the first organic compound and the fluorescent spectrum of the second organic compound can be converted into an emission spectrum which is located on the longer wavelength side.

Figure 25:
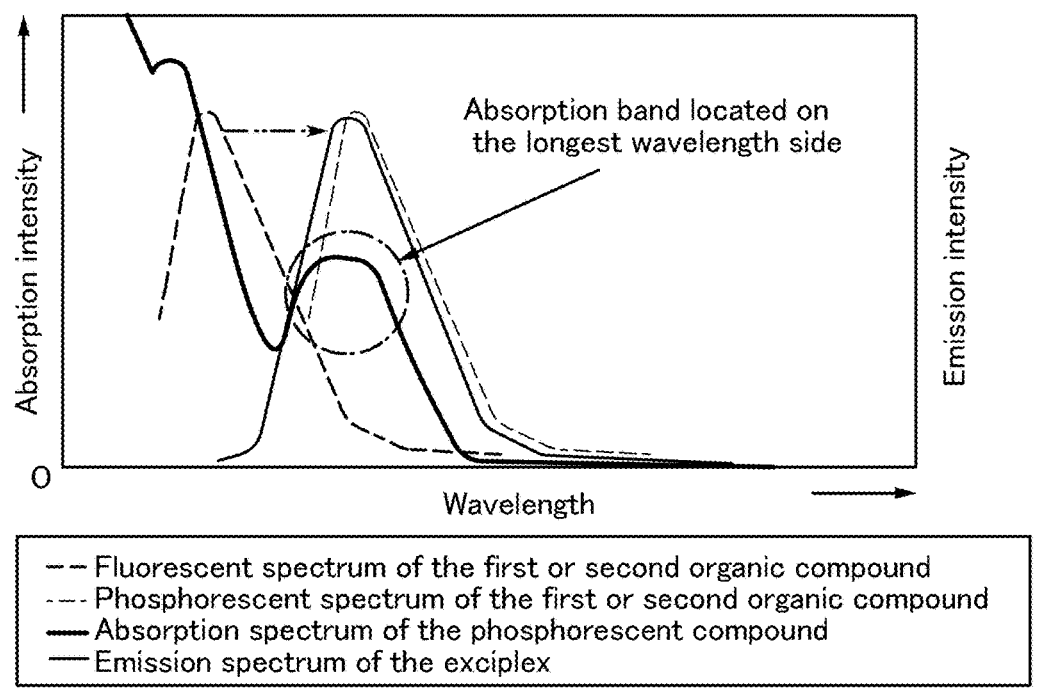
FIG. 25 illustrates a concept of one embodiment of the present invention.

Therefore, as illustrated in FIG. 25, even when the fluorescent spectrum of the first organic compound (or the second organic compound) is located on the shorter wavelength side with respect to the absorption band of the phosphorescent compound which is located on the longest wavelength side, and does not have an overlap with the absorption band, an emission spectrum with a long wavelength can be obtained by forming an exciplex so as to have a large overlap with the absorption band. The light-emitting element of one embodiment of the present invention transfers energy by utilizing the overlap between the emission spectrum of the exciplex and the absorption spectrum of the phosphorescent compound and thus has high energy transfer efficiency. Therefore, in one embodiment of the present invention, a light-emitting element having high external quantum efficiency can be obtained.

In addition, the exciplex exists only in an excited state and thus has no ground state capable of absorbing energy. Therefore, a phenomenon in which the phosphorescent compound is deactivated by reverse energy transfer of the singlet excited state and triplet excited state of the phosphorescent compound to the exciplex before light emission (i.e., emission efficiency is lowered) is not considered to occur in principle. This also contributes to improvement of external quantum efficiency.

In addition, the exciplex is considered to have an extremely small difference between singlet excited energy and triplet excited energy. In other words, the emission spectrum of the exciplex from the single state and the emission spectrum thereof from the triplet state are highly close to each other. Accordingly, in the case where a design is implemented such that the emission spectrum of the exciplex (generally the emission spectrum of the exciplex from the singlet state) overlaps with the absorption band of the phosphorescent compound on the longest wavelength side as described above, the emission spectrum of the exciplex from the triplet state (which is not observed at room temperature and not observed even at low temperature in many cases) also overlaps with the absorption band of the phosphorescent compound which is located on the longest wavelength side. More specifically, this means that energy can be efficiently transferred to the phosphorescent compound from the exciplex in both the singlet state and the triplet state.

Molecular orbital calculations were performed as described below to verify whether or not an exciplex actually has such characteristics. In general, a combination of a heteroaromatic compound and an aromatic amine often forms an exciplex under the influence of the lowest unoccupied molecular orbital (LUMO) level of the heteroaromatic compound which is deeper than the LUMO level of the aromatic amine (the property of easily accepting electrons) and the highest occupied molecular orbital (HOMO) level of the aromatic amine which is shallower than the HOMO level of the heteroaromatic compound (the property of easily accepting holes). Thus, calculations were performed using a combination of dibenzo[f,h]quinoxaline (abbreviation: DBq) which is a typical skeleton forming the LUMO of a heteroaromatic compound and triphenylamine (abbreviation: TPA) which is a typical skeleton forming the HOMO of an aromatic amine.

First, the optimal molecular structures and the excitation energies of DBq alone and TPA alone in the lowest singlet excited state ($S_1$) and the lowest triplet excited state ($T_1$) were calculated using the time-dependent density functional theory (TD-DFT). Furthermore, the excitation energy of a dimer of DBq and TPA was also calculated. In the DFT, the total energy is represented as the sum of potential energy, electrostatic energy between electrons, electronic kinetic energy, and exchange-correlation energy including all the complicated interactions between electrons. Also in the DFT, an exchange-correlation interaction is approximated by a functional (a function of another function) of one electron potential represented in terms of electron density to enable high-speed, high-accuracy calculations. Here, B3LYP which was a hybrid functional was used to specify the weight of each parameter related to exchange-correlation energy. In addition, as a basis function, 6-311 (a basis function of a triple-split valence basis set using three contraction functions for each valence orbital) was applied to all the atoms. By the above basis function, for example, 1s to 3s orbitals are considered in the case of hydrogen atoms, while 1s to 4s and 2p to 4p orbitals are considered in the case of carbon atoms. Furthermore, to improve calculation accuracy, the p function and the d function as polarization basis sets were added to hydrogen atoms and atoms other than hydrogen atoms, respectively.

Note that Gaussian 09 was used as a quantum chemistry computational program. A high performance computer (Altix 4700, manufactured by SGI Japan, Ltd.) was used for the calculations.

Figure 64:
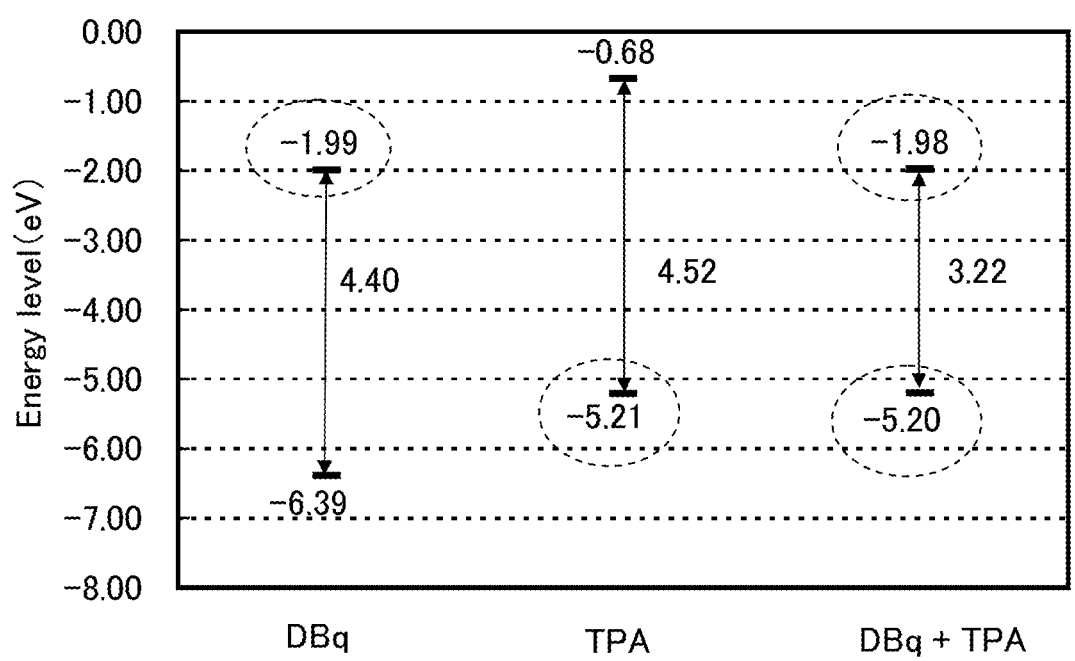
FIG. 64 shows calculation results according to one embodiment of the present invention.

First, the HOMO levels and the LUMO levels of DBq alone, TPA alone, and a dimer of DBq and TPA were calculated. FIG. 64 shows the HOMO levels and the LUMO levels, and FIGS. 65(A1), 65(A2), 65(B1), 65(B2), 65(C1), and 65(C2) show HOMO and LUMO distributions.

FIG. 65(A1) shows the LUMO distribution of DBq alone; FIG. 65(A2), the HOMO distribution of DBq alone; FIG. 65(B1), the LUMO distribution of TPA alone; FIG. 65(B2), the HOMO distribution of TPA alone; FIG. 65(C1), the LUMO distribution of the dimer of DBq and TPA; and FIG. 65(C2), the HOMO distribution of the dimer of DBq and TPA.

As shown in FIG. 64, it is suggested that the dimer of DBq and TPA forms an exciplex of DBq and TPA under the influence of the LUMO level (−1.99 eV) of DBq which is deeper (lower) than the LUMO level of TPA and the HOMO level (−5.21 eV) of TPA which is shallower (higher) than the HOMO level of DBq. In fact, as is clear from FIGS. 65(C1) and 65(C2), the LUMO of the dimer of DBq and TPA is distributed on the DBq side, and the HOMO thereof is distributed on the TPA side.

Next, excitation energies obtained from the optimal molecular structures of DBq alone in $S_1$ and $T_1$ will be shown. Here, the $S_1$ and $T_1$ excitation energies correspond to fluorescence and phosphorescence wavelengths, respectively, obtained from DBq alone. The $S_1$ excitation energy of DBq alone is 3.294 eV, and the fluorescence wavelength is 376.4 nm. The $T_1$ excitation energy of DBq alone is 2.460 eV, and the phosphorescence wavelength is 504.1 nm.

In addition, excitation energies obtained from the optimal molecular structures of TPA alone in $S_1$ and $T_1$ will be shown. Here, the $S_1$ and $T_1$ excitation energies correspond to fluorescence and phosphorescence wavelengths, respectively, obtained from TPA alone. The $S_1$ excitation energy of TPA alone is 3.508 eV, and the fluorescence wavelength is 353.4 nm. The $T_1$ excitation energy of TPA alone is 2.610 eV, and the phosphorescence wavelength is 474.7 nm.

Furthermore, excitation energies obtained from the optimal molecular structures of the dimer of DBq and TPA in $S_1$ and $T_1$ will be shown. The $S_1$ and $T_1$ excitation energies correspond to fluorescence and phosphorescence wavelengths, respectively, obtained from the dimer of DBq and TPA. The $S_1$ excitation energy of the dimer of DBq and TPA is 2.036 eV, and the fluorescence wavelength is 609.1 nm. The $T_1$ excitation energy of the dimer of DBq and TPA is 2.030 eV, and the phosphorescence wavelength is 610.0 nm.

It is found from the above that each of the phosphorescence wavelengths of DBq alone and TPA alone is shifted to the longer wavelength side by about 100 nm with respect to the fluorescence wavelength. This result shows a tendency similar to that of CBP (measured values) described above and supports the validity of the calculations.

On the other hand, it is found that the fluorescence wavelength of the dimer of DBq and TPA is located on the longer wavelength side with respect to the fluorescence wavelengths of DBq alone and TPA alone. This result shows a tendency similar to that of examples (measured values) described below and supports the validity of the calculations. It is also found that the difference between the fluorescence wavelength and the phosphorescence wavelength of the dimer of DBq and TPA is only 0.9 nm and that these wavelengths are substantially the same.

These results indicate that the exciplex can integrate the singlet excitation energy and the triplet excitation energy into substantially the same energy. Therefore, it is indicated as described above that the exciplex can efficiently transfer energy to the phosphorescent compound from both the singlet state and the triplet state thereof.

Such an effect is specific to the use of an exciplex as a medium for energy transfer. In general, energy transfer from the singlet excited state or triplet excited state of a host material to a phosphorescent compound is considered. On the other hand, one embodiment of the present invention greatly differs from a conventional technique in that an exciplex of a host material and another material (an exciplex of a first organic compound and a second organic compound) is formed first and energy transfer from the exciplex is used. In addition, this difference provides unprecedentedly high emission efficiency.

Note that in general, the use of an exciplex for a light-emitting layer of a light-emitting element has a value such as being capable of controlling the emission color, but usually causes a significant decrease in emission efficiency. Therefore, the use of an exciplex has been considered unsuitable for obtaining a highly efficient light-emitting element. However, the present inventors have found that the use of an exciplex as a medium for energy transfer to a phosphorescent compound enables, on the contrary, emission efficiency to be maximized as shown in one embodiment of the present invention. This technical idea conflicts with the conventional fixed idea.

To make the emission spectrum of the exciplex and the absorption spectrum of the guest material sufficiently overlap each other, the difference between the energy of a peak of the emission spectrum and the energy of a peak of the absorption band on the lowest energy side in the absorption spectrum is preferably 0.3 eV or less. The difference is more preferably 0.2 eV or less, even more preferably 0.1 eV or less.

In addition, in one embodiment of the present invention, an exciplex is formed from a singlet exciton of the first organic compound or the second organic compound.

In a light-emitting element of one embodiment of the present invention, a possible elementary process of formation of an exciplex is that one of the first and second organic compounds forms a singlet exciton and then interacts with the other in the ground state. As described above, the emission spectrum of the exciplex and the absorption spectrum of the phosphorescent compound can largely overlap; thus, energy transfer efficiency can be increased. Accordingly, a light-emitting element having high external quantum efficiency can be obtained.

The singlet exciton has a short excitation lifetime (small $\tau$) as described above. Thus, there is a problem in that part of excitation energy is deactivated (through light emission or thermal deactivation) before the excitation energy is transferred from the singlet exciton to a guest material ($\Phi_{ET}$ tends to be small in Formula (3)). However, in one embodiment of the present invention, such deactivation of excitation energy can be suppressed because the singlet exciton rapidly forms an exciplex. Furthermore, the exciplex has a relatively long excitation lifetime, which is considered favorable to energy transfer efficiency $\Phi_{ET}$. Accordingly, the deactivation of the singlet excitation energy of the host material that may affect not only the efficiency of an element but also the lifetime thereof can be suppressed by application of one embodiment of the present invention, so that a light-emitting element having a long lifetime can be obtained.

In one embodiment of the present invention, it is also preferable that the excitation energy of the exciplex be sufficiently transferred to the phosphorescent compound, and that light emission from the exciplex be not substantially observed. Therefore, energy is preferably transferred to the phosphorescent compound through the exciplex so that the phosphorescent compound emits phosphorescence.

According to the above-described concept of energy transfer, one embodiment of the present invention is effective in the case where at least one of the first and second organic compounds is a fluorescent compound (i.e., a compound which is likely to undergo light emission or thermal deactivation from the singlet excited state). Therefore, it is preferable that at least one of the first and second organic compounds be a fluorescent compound.

Note that in the case where a phosphorescent compound is used as an organic compound serving as a host material, the organic compound itself is likely to emit light and unlikely to allow energy to be transferred to a guest material. In this case, it is favorable if the organic compound could emit light efficiently, but it is difficult to achieve high emission efficiency because the organic compound serving as a host material causes the problem of concentration quenching. For this reason, it is preferable that the organic compound be a fluorescent compound and energy transfer be achieved with the above-described composition.

In addition, in one embodiment of the present invention, it is preferable that the phosphorescent compound be an organometallic complex.

The exciplex used in one embodiment of the present invention will be described in detail below.

<Exciplex>

The exciplex (excited complex) is formed by an interaction between dissimilar molecules in excited states. The exciplex is generally known to be easily formed between a material having a relatively deep LUMO level and a material having a relatively shallow HOMO level.

An emission wavelength depends on a difference in energy between the HOMO level and the LUMO level. When the energy difference is large, the emission wavelength is short. When the energy difference is small, the emission wavelength is long.

Here, the HOMO levels and LUMO levels of the first organic compound and the second organic compound used in one embodiment of the present invention are different from each other. Specifically, the energy levels are higher in the following order: the HOMO level of the first organic compound<the HOMO level of the second organic compound<the LUMO level of the first organic compound<the LUMO level of the second organic compound (see FIG. 17).

Figure 17:
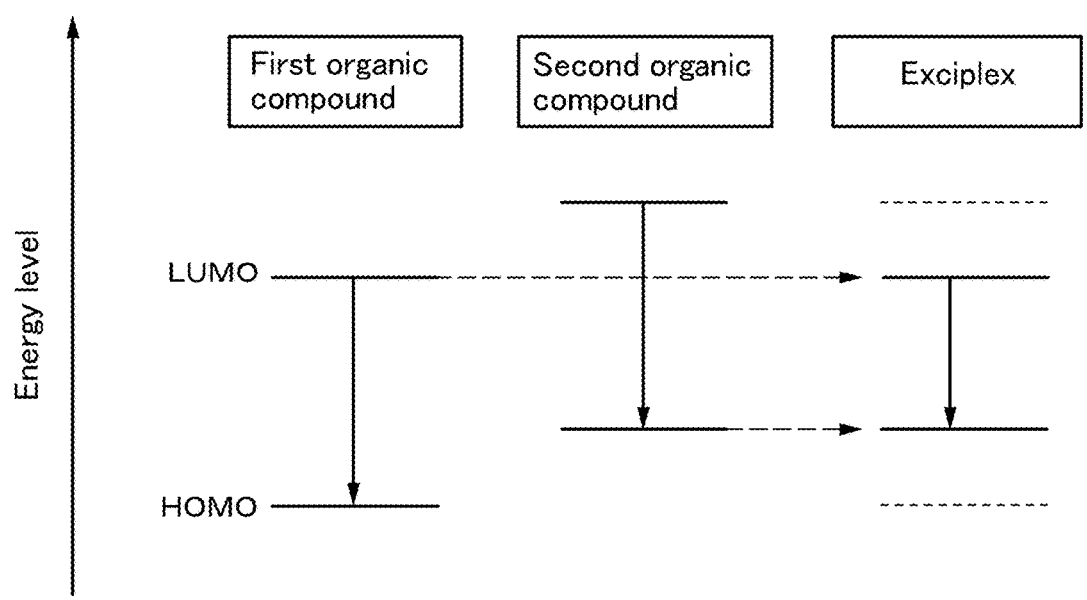
FIG. 17 illustrates energy levels of an exciplex applied to one embodiment of the present invention.

When the exciplex is formed by these two organic compounds, the LUMO level and the HOMO level of the exciplex originate from the first organic compound and the second organic compound, respectively (see FIG. 17). Therefore, the energy difference of the exciplex is smaller than the energy difference of the first organic compound and the energy difference of the second organic compound. In other words, the emission wavelength of the exciplex is longer than the emission wavelengths of the first organic compound and the second organic compound.

The formation process of the exciplex used in one embodiment of the present invention is considered to be roughly classified into two processes.

«Electroplex»

In this specification, the term "electroplex" means that the first organic compound in the ground state and the second organic compound in the ground state directly form an exciplex.

As described above, in general, when an electron and a hole are recombined in a host material, excitation energy is transferred from the host material in an excited state to a guest material, whereby the guest material is brought into an excited state to emit light.

At this time, before the excitation energy is transferred from the host material to the guest material, the host material itself emits light or the excitation energy turns into thermal energy, which leads to partial deactivation of the excitation energy. In particular, when the host material is in a singlet excited state, excitation lifetime is shorter than that when it is in a triplet excited state, which easily leads to deactivation of singlet excitation energy. The deactivation of excitation energy is one of causes for a decrease in lifetime of a light-emitting element.

However, in one embodiment of the present invention, an electroplex is formed from the first organic compound and the second organic compound having carriers (cation or anion); therefore, formation of a singlet exciton having a short excitation lifetime can be suppressed. In other words, there can be a process where an exciplex is directly formed without formation of a singlet exciton. Thus, deactivation of the singlet excitation energy can be inhibited. Accordingly, a light-emitting element having a long lifetime can be obtained.

For example, in the case where the first organic compound is a compound having an electron-trapping property and the second organic compound is a compound having a hole-trapping property, an electroplex is formed directly from an anion of the first organic compound and a cation of the second organic compound. It is a novel concept to obtain a light-emitting element having high emission efficiency by suppressing the generation of the singlet excited state of a host material and transferring energy from an electroplex to a guest material, in the above-described manner. Note that the generation of the triplet excited state of the host material is similarly suppressed and an electroplex is directly formed; therefore, energy transfer is considered to occur from the electroplex to the guest material. This mechanism is also novel.

The emission spectrum of the electroplex formed is located on the longer wavelength side with respect to the emission wavelength of each of the first and second organic compounds.

The overlap between the emission spectrum of the electroplex and the absorption spectrum of the phosphorescent compound is larger than the overlap between the emission spectrum of the first organic compound (or the second organic compound) and the absorption spectrum of the phosphorescent compound. The light-emitting element of one embodiment of the present invention transfers energy by utilizing the overlap between the emission spectrum of the electroplex and the absorption spectrum of the phosphorescent compound and thus has high energy transfer efficiency. Therefore, in one embodiment of the present invention, a light-emitting element having high external quantum efficiency can be obtained.

«Formation of Exciplex by Exciton»

As another process, there is thought to be an elementary process where one of the first and second organic compounds forms a singlet exciton and then interacts with the other in the ground state to form an exciplex. Unlike an electroplex, a singlet excited state of the first organic compound or the second organic compound is temporarily generated in this case, but this is rapidly converted into an exciplex, and thus, deactivation of single excitation energy can be inhibited. Thus, it is possible to inhibit deactivation of excitation energy of the first organic compound or the second organic compound. Accordingly, in one embodiment of the present invention, a light-emitting element having a long lifetime can be obtained. Note that it is considered that the triplet excited state of the host material is also rapidly converted into an exciplex and energy is transferred from the exciplex to the guest material.

The emission spectrum of the exciplex formed is located on the longer wavelength side with respect to the emission wavelength of each of the first and second organic compounds.

The overlap between the emission spectrum of the exciplex and the absorption spectrum of the phosphorescent compound is larger than the overlap between the emission spectrum of the first organic compound (or the second organic compound) and the absorption spectrum of the phosphorescent compound. The light-emitting element of one embodiment of the present invention transfers energy by utilizing the overlap between the emission spectrum of the exciplex and the absorption spectrum of the phosphorescent compound and thus has high energy transfer efficiency. Accordingly, in one embodiment of the present invention, a light-emitting element having high external quantum efficiency can be obtained.

For example, in the case where the first organic compound is a compound having an electron-trapping property, the second organic compound is a compound having a hole-trapping property, and the difference between the HOMO levels and the difference between the LUMO levels of these compounds are large (specifically, 0.3 eV or more), electrons are selectively injected into the first organic compound and holes are selectively injected into the second organic compound. In this case, it is thought that the process where an electroplex is formed takes precedence over the process where an exciplex is formed through a singlet exciton.

Note that this embodiment can be combined with any of the other embodiments as appropriate.

(Embodiment 2)

In this embodiment, a light-emitting element of one embodiment of the present invention will be described with reference to FIGS. 16A to 16C.

Figure 16A:
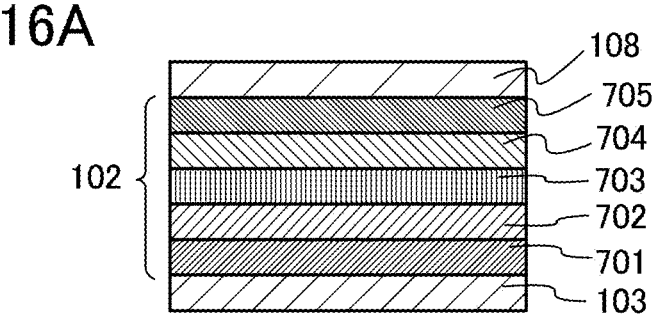
FIGS. 16A to 16C each illustrate a light-emitting element of one embodiment of the present invention.

FIG. 16A illustrates a light-emitting element including an EL layer 102 between a first electrode 103 and a second electrode 108. The light-emitting element in FIG. 16A includes a hole-injection layer 701, a hole-transport layer 702, a light-emitting layer 703, an electron-transport layer 704, and an electron-injection layer 705 which are stacked over the first electrode 103 in this order, and the second electrode 108 provided thereover.

The first electrode 103 is preferably formed using any of metals, alloys, conductive compounds, mixtures thereof, and the like which have a high work function (specifically, 4.0 eV or more). Specific examples include indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide (IWZO), and the like. Films of these conductive metal oxides are usually formed by a sputtering method, but may be formed by application of a sol-gel method or the like. For example, an indium oxide-zinc oxide film can be formed by a sputtering method using a target in which zinc oxide is added to indium oxide at 1 wt % to 20 wt %. Further, an IWZO film can be formed by a sputtering method using a target in which tungsten oxide is added to indium oxide at 0.5 wt % to 5 wt % and zinc oxide is added to indium oxide at 0.1 wt % to 1 wt %. Other examples are graphene, gold, platinum, nickel, tungsten, chromium, molybdenum, iron, cobalt, copper, palladium, nitrides of metal materials (e.g., titanium nitride), and the like.

Note that when a layer included in the EL layer 102 and formed in contact with the first electrode 103 is formed using a later-described composite material formed by combining an organic compound and an electron acceptor (an acceptor), as a substance used for the first electrode 103, any of a variety of metals, alloys, electrically conductive compounds, mixtures thereof, and the like can be used regardless of the work function; for example, aluminum, silver, an alloy containing aluminum (e.g., Al—Si), or the like can also be used.

The first electrode 103 can be formed by, for example, a sputtering method, an evaporation method (including a vacuum evaporation method), or the like.

The second electrode 108 is preferably formed using any of metals, alloys, electrically conductive compounds, mixtures thereof, and the like which have a low work function (preferably, 3.8 eV or lower). Specific examples thereof include elements that belong to Groups 1 and 2 in the periodic table, that is, alkali metals such as lithium and cesium, alkaline earth metals such as calcium and strontium, magnesium, alloys thereof (e.g., Mg—Ag and Al—Li), rare-earth metals such as europium and ytterbium, alloys thereof, aluminum, silver, and the like.

When a layer included in the EL layer 102 and formed in contact with the second electrode 108 is formed using a later-described composite material formed by combining an organic compound and an electron donor (a donor), any of a variety of conductive materials, such as Al, Ag, ITO, and indium oxide-tin oxide containing silicon or silicon oxide, can be used regardless of the work function.

Note that when the second electrode 108 is formed, a vacuum evaporation method or a sputtering method can be used. In the case of using a silver paste or the like, a coating method, an inkjet method, or the like can be used.

The EL layer 102 includes at least the light-emitting layer 703. For part of the EL layer 102, a known substance can be used, and either a low molecular compound or a high molecular compound can be used. Note that substances forming the EL layer 102 may consist of organic compounds or may include an inorganic compound as a part.

Further, as illustrated in FIG. 16A, the EL layer 102 includes not only the light-emitting layer 703 but also an appropriate combination of the following layers: the hole-injection layer 701 including a substance having a high hole-injection property, the hole-transport layer 702 including a substance having a high hole-transport property, the electron-transport layer 704 including a substance having a high electron-transport property, the electron-injection layer 705 including a substance having a high electron-injection property, and the like.

The hole-injection layer 701 is a layer that contains a substance having a high hole-injection property. As the substance having a high hole-injection property, a metal oxide such as molybdenum oxide, titanium oxide, vanadium oxide, rhenium oxide, ruthenium oxide, chromium oxide, zirconium oxide, hafnium oxide, tantalum oxide, silver oxide, tungsten oxide, or manganese oxide can be used. Alternatively, a phthalocyanine-based compound such as phthalocyanine (abbreviation: $H_2Pc$) or copper(II) phthalocyanine (abbreviation: CuPc) can be used.

Other examples of the substance which can be used are aromatic amine compounds and the like which are low molecular organic compounds, such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Still other examples of the substance which can be used are high molecular compounds (e.g., oligomers, dendrimers, and polymers), such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD), and high molecular compounds to which acid is added, such as poly(3,4-ethylenedioxythiophene)/poly(styrenesulfonic acid) (PEDOT/PSS), and polyaniline/poly(styrenesulfonic acid) (PAni/PSS).

For the hole-injection layer 701, the composite material formed by combining an organic compound and an electron acceptor (an acceptor) may be used. Such a composite material, in which holes are generated in the organic compound by the electron acceptor, has high hole-injection and hole-transport properties. In this case, the organic compound is preferably a material excellent in transporting the generated holes (a substance having a high hole-transport property).

Examples of the organic compound used for the composite material can be a variety of compounds, such as aromatic amine compounds, carbazole derivatives, aromatic hydrocarbons, and high molecular compounds (e.g., oligomers, dendrimers, and polymers). The organic compound used for the composite material is preferably an organic compound having a high hole-transport property, and is specifically preferably a substance having a hole mobility of $10^{-6}$ cm$^2$/Vs or more. Note that other than these substances, any substance that has a property of transporting more holes than electrons may be used. Organic compounds that can be used for the composite material will be specifically described below.

Examples of the organic compound that can be used for the composite material are aromatic amine compounds, such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP), and carbazole derivatives, such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)phenyl]-10-phenylanthracene (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl]-2,3,5,6-tetraphenylbenzene.

Other examples of the organic compound that can be used are aromatic hydrocarbon compounds, such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl] anthracene, and 2,3,6,7-tetramethyl-9,10-di(1-naphthyl)anthracene.

Other examples of the organic compound that can be used are aromatic hydrocarbon compounds, such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2, 2-diphenylvinyl)biphenyl (abbreviation: DPVBi), and 9,10-bis[4-(2,2-diphenylvinyl)phenyl] anthracene (abbreviation: DPVPA).

Further, examples of the electron acceptor are organic compounds, such as 7,7,8,8-tetracyano-2,3,5,6-tetrafluoro-quinodimethane (abbreviation: $F_4$-TCNQ) and chloranil, oxides of transition metals, oxides of metals that belong to Groups 4 to 8 in the periodic table, and the like. Specifically, vanadium oxide, niobium oxide, tantalum oxide, chromium oxide, molybdenum oxide, tungsten oxide, manganese oxide, and rhenium oxide are preferable because of their high electron-accepting property. Among these, molybdenum oxide is especially preferable since it is stable in the air, has a low hygroscopic property, and is easy to handle.

The composite material may be formed using the above-described electron acceptor and the above-described high molecular compound such as PVK, PVTPA, PTPDMA, or Poly-TPD, and may be used for the hole-injection layer 701.

The hole-transport layer 702 is a layer that contains a substance having a high hole-transport property. Examples of the substance having a high hole-transport property are aromatic amine compounds such as NPB, TPD, BPAFLP, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly substances that have a hole mobility of $10^{-6}$ cm$^2$/Vs or more. Note that other than these substances, any substance that has a property of transporting more holes than electrons may be used. Note that the layer containing a substance having a high hole-transport property is not limited to a single layer, and may be a stack of two or more layers containing any of the above substances.

For the hole-transport layer 702, a carbazole derivative such as CBP, CzPA, or PCzPA or an anthracene derivative such as t-BuDNA, DNA, or DPAnth may be used.

For the hole-transport layer 702, a high molecular compound such as PVK, PVTPA, PTPDMA, or Poly-TPD can also be used.

The light-emitting layer 703 is a layer that contains a light-emitting substance. The light-emitting layer 703 of this embodiment contains a phosphorescent compound, a first organic compound, and a second organic compound. The phosphorescent compound is a light-emitting substance (guest material). One of the first and second organic compounds, the content of which is higher than that of the other in the light-emitting layer 703, is a host material. Embodiment 1 can be referred to for specifics.

As the phosphorescent compound, an organometallic complex is preferable, and in particular, an iridium complex is preferable. In consideration of energy transfer due to Förster mechanism described above, the molar absorption coefficient of the absorption band of the phosphorescent compound which is located on the longest wavelength side is preferably 2000 $M^{-1}\cdot cm^{-1}$ or more, more preferably 5000 $M^{-1}\cdot cm^{-1}$ or more. Examples of the compound having such a high molar absorption coefficient are bis(3,5-dimethyl-2-phenylpyrazinato)(dipivaloylmethanato)iridium(III) (abbreviation: [Ir(mppr-Me)$_2$(dpm)]), (acetylacetonato)bis(4,6-diphenylpyrimidinato)iridium(III) (abbreviation: [Ir(dppm)$_2$(acac)]), bis(2,3,5-triphenylpyrazinato)(dipivaloylmethanato)iridium(III) (abbreviation: [Ir(tppr)$_2$(dpm)]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), and the like. In particular, when a material having a molar absorption coefficient of 5000 $M^{-1}\cdot cm^{-1}$ or more, such as [Ir(dppm)$_2$(acac)], is used, a light-emitting element that can achieve an external quantum efficiency of about 30% can be obtained.

The first organic compound and the second organic compound are preferably, for example, a combination of any one of compounds which are likely to accept electrons (typically, heteroaromatic compounds), such as 2-[3-(dibenzothiophen-4-yl)phenyl]dibenzo[f,h]quinoxaline (abbreviation: 2mDBTPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), and 2-[4-(dibenzothiophen-4-yl)phenyl]-1-phenyl-1H-benzimidazole (abbreviation: DBTBIm-II), and any one of compounds which are likely to accept holes (typically, aromatic amine compounds and carbazole compounds), such as 4,4'-bis[N-(1-naphthyl)-N-phenylamino]biphenyl (abbreviation: NPB or α-NPD), 4-phenyl-4'-(9-phenyl-9H-carbazol-3-yl)triphenylamine (abbreviation: PCBA1BP), 4,4'-di(1-naphthyl)-4''-(9-phenyl-9H-carbazol-3-yl)triphenylamine (abbreviation: PCBNBB), 4-(1-naphthyl)-4'-phenyltriphenylamine (abbreviation: αNBA1BP), 2,7-bis[N-(4-diphenylaminophenyl)-N-phenylamino]-spiro-9,9'-bifluorene (abbreviation: DPA2SF), 4,4',4''-tris[N-(1-naphthyl)-N-phenylamino]triphenylamine (abbreviation: 1'-TNATA), and 9-phenyl-9H-3-(9-phenyl-9H-carbazol-3-yl)carbazole (abbreviation: PCCP). With such a composition, it is possible to obtain the effect of improvement of emission efficiency and lifetime not only by energy transfer from an exciplex but also by adjustment of carrier balance between hole transport and electron transport in a light-emitting layer. Note that the present invention is not limited to these compounds as long as the combination can form an exciplex.

Note that the exciplex may be formed at the interface between two layers. For example, when a layer containing the second organic compound and a layer containing the first organic compound are stacked, the exciplex is formed in the vicinity of the interface thereof. These two layers may be used as the light-emitting layer in one embodiment of the present invention. In that case, the phosphorescent compound is added to the vicinity of the interface. The phosphorescent compound may be added to one of the two layers or both.

The electron-transport layer 704 is a layer that contains a substance having a high electron-transport property. Examples of the substance having a high electron-transport property are metal complexes such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, and bis[2-(2-hydroxyphenyl)benzothiazolato]zinc (abbreviation: Zn(BTZ)$_2$). Other examples thereof are heteroaromatic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), 4,4'-bis(5-methylbenzoxazol-2-yl)stilbene (abbreviation: BzOs). Still other examples are high molecular compounds such as poly(2,5-pyridine-diyl) (abbreviation: PPy), poly[(9,9-dihexylfluorene-2,7-diyl)-co-(pyridine-3,5-diyl)] (abbreviation: PF-Py), and poly[(9,9- dioctylfluorene-2,7-diyl)-co-(2,2'-bipyridine-6,6'-diyl)] (abbreviation: PF-BPy). The substances mentioned here are mainly substances having an electron mobility of $10^{-6}$ cm$^2$/Vs or more. Note that other than these substances, any substance that has a property of transporting more holes than electrons may be used for the electron-transport layer.

Further, the electron-transport layer is not limited to a single layer, and may be a stack of two or more layers containing any of the above substances.

The electron-injection layer 705 is a layer that contains a substance having a high electron-injection property. Examples of the substance that can be used for the electron-injection layer 705 are alkali metals, alkaline earth metals, and compounds thereof, such as lithium, cesium, calcium, lithium fluoride, cesium fluoride, calcium fluoride, and lithium oxide, rare earth metal compounds, such as erbium fluoride, and the above-mentioned substances used for the electron-transport layer 704.

Alternatively, a composite material formed by combining an organic compound and an electron donor (a donor) may be used for the electron-injection layer 705. Such a composite material, in which electrons are generated in the organic compound by the electron donor, has high electron-injection and electron-transport properties. The organic compound here is preferably a material excellent in transporting the generated electrons, and specifically any of the above substances (such as metal complexes and heteroaromatic compounds) for the electron-transport layer 704 can be used. As the electron donor, a substance showing an electron-donating property with respect to the organic compound may be used. Preferable specific examples of the electron donor are alkali metals, alkaline earth metals, and rare earth metals, such as lithium, cesium, magnesium, calcium, erbium, and ytterbium. Any of alkali metal oxides and alkaline earth metal oxides is preferable, examples of which are lithium oxide, calcium oxide, barium oxide, and the like, and a Lewis base such as magnesium oxide or an organic compound such as tetrathiafulvalene (abbreviation: TTF) can be used.

Note that the hole-injection layer 701, the hole-transport layer 702, the light-emitting layer 703, the electron-transport layer 704, and the electron-injection layer 705 which are mentioned above can each be formed by a method such as an evaporation method (including a vacuum evaporation method), an inkjet method, or a coating method.

Figure 16B:
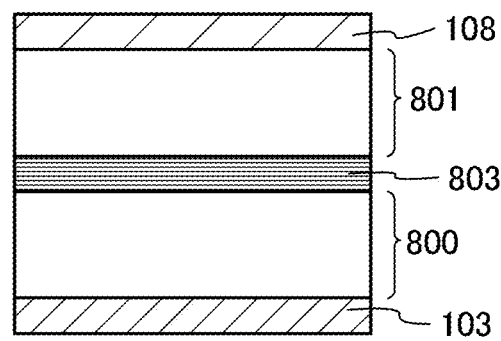

A plurality of EL layers may be stacked between the first electrode 103 and the second electrode 108 as illustrated in FIG. 16B. In that case, a charge-generation layer 803 is preferably provided between a first EL layer 800 and a second EL layer 801 which are stacked. The charge-generation layer 803 can be formed using the above-described composite material. Further, the charge-generation layer 803 may have a stacked structure including a layer containing the composite material and a layer containing another material. In that case, as the layer containing another material, a layer containing an electron-donating substance and a substance with a high electron-transport property, a layer formed of a transparent conductive film, or the like can be used. As for a light-emitting element having such a structure, problems such as energy transfer and quenching hardly occur, and a light-emitting element which has both high emission efficiency and a long lifetime can be easily obtained owing to a wider choice of materials. Moreover, a light-emitting element which provides phosphorescence from one of the EL layers and fluorescence from the other of the EL layers can be readily obtained. This structure can be combined with any of the above-described structures of the EL layer.

Furthermore, by making emission colors of EL layers different, light of a desired color can be obtained from the light-emitting element as a whole. For example, the emission colors of first and second EL layers are complementary in a light-emitting element having the two EL layers, so that the light-emitting element can be made to emit white light as a whole. Further, the same applies to a light-emitting element having three or more EL layers.

Figure 16C:
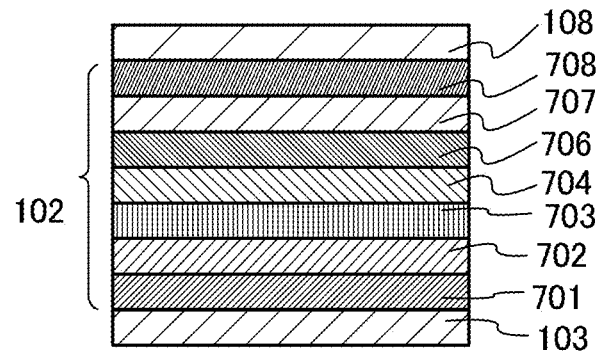

As illustrated in FIG. 16C, the EL layer 102 may include the hole-injection layer 701, the hole-transport layer 702, the light-emitting layer 703, the electron-transport layer 704, an electron-injection buffer layer 706, an electron-relay layer 707, and a composite material layer 708 which is in contact with the second electrode 108, between the first electrode 103 and the second electrode 108.

It is preferable to provide the composite material layer 708 which is in contact with the second electrode 108, in which case damage caused to the EL layer 102 particularly when the second electrode 108 is formed by a sputtering method can be reduced. The composite material layer 708 can be formed using the above-described composite material in which an organic compound having a high hole-transport property contains an acceptor substance.

Further, by providing the electron-injection buffer layer 706, an injection barrier between the composite material layer 708 and the electron-transport layer 704 can be reduced; thus, electrons generated in the composite material layer 708 can be easily injected to the electron-transport layer 704.

For the electron-injection buffer layer 706, a substance having a high electron-injection property, such as an alkali metal, an alkaline earth metal, a rare earth metal, a compound of the above metal (e.g., an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate), can be used.

Further, in the case where the electron-injection buffer layer 706 contains a substance having a high electron-transport property and a donor substance, the donor substance is preferably added so that the mass ratio of the donor substance to the substance having a high electron-transport property is in the range from 0.001:1 to 0.1:1. Note that as the donor substance, an organic compound such as tetrathianaphthacene (abbreviation: TTN), nickelocene, or decamethylnickelocene can be used as well as an alkali metal, an alkaline earth metal, a rare earth metal, a compound of the above metal (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate). Note that as the substance having a high electron-transport property, a material similar to the material for the electron-transport layer 704 described above can be used.

Furthermore, it is preferable that the electron-relay layer 707 be formed between the electron-injection buffer layer 706 and the composite material layer 708. The electron-relay layer 707 is not necessarily provided; however, by providing the electron-relay layer 707 having a high electron-transport property, electrons can be rapidly transported to the electron-injection buffer layer 706.

The structure in which the electron-relay layer 707 is sandwiched between the composite material layer 708 and the electron-injection buffer layer 706 is a structure in which the acceptor substance contained in the composite material layer 708 and the donor substance contained in the electron-injection buffer layer 706 are less likely to interact with each other, and thus their functions hardly interfere with each other. Therefore, an increase in drive voltage can be prevented.

The electron-relay layer 707 contains a substance having a high electron-transport property and is formed so that the LUMO level of the substance having a high electron-transport property is located between the LUMO level of the acceptor substance contained in the composite material layer 708 and the LUMO level of the substance having a high electron-transport property contained in the electron-transport layer 704. In the case where the electron-relay layer 707 contains a donor substance, the donor level of the donor substance is also controlled so as to be located between the LUMO level of the acceptor substance contained in the composite material layer 708 and the LUMO level of the substance having a high electron-transport property contained in the electron-transport layer 704. As a specific value of the energy level, the LUMO level of the substance having a high electron-transport property contained in the electron-relay layer 707 is preferably higher than or equal to −5.0 eV, more preferably higher than or equal to −5.0 eV and lower than or equal to −3.0 eV.

As the substance having a high electron-transport property contained in the electron-relay layer 707, a phthalocyanine-based material or a metal complex having a metal-oxygen bond and an aromatic ligand is preferably used.

As the phthalocyanine-based material contained in the electron-relay layer 707, specifically, any of CuPc, a phthalocyanine tin(II) complex (SnPc), a phthalocyanine zinc complex (ZnPc), cobalt(II) phthalocyanine, β-form (CoPc), phthalocyanine iron (FePc), and vanadyl 2,9,16,23-tetraphenoxy-29H,31H-phthalocyanine (PhO-VOPc), is preferably used.

As the metal complex having a metal-oxygen bond and an aromatic ligand, which is contained in the electron-relay layer 707, a metal complex having a metal-oxygen double bond is preferably used. The metal-oxygen double bond has an acceptor property (a property of easily accepting electrons); thus, electrons can be transferred (donated and accepted) more easily. Further, the metal complex having a metal-oxygen double bond is considered stable. Thus, the use of the metal complex having the metal-oxygen double bond enables the light-emitting element to be driven more stably at low voltage.

As the metal complex having a metal-oxygen bond and an aromatic ligand, a phthalocyanine-based material is preferable. Specifically, any of vanadyl phthalocyanine (VOPc), a phthalocyanine tin(IV) oxide complex (SnOPc), and a phthalocyanine titanium oxide complex (TiOPc) is preferable because a metal-oxygen double bond is likely to act on another molecule in terms of a molecular structure and an acceptor property is high.

Note that as the phthalocyanine-based materials mentioned above, a phthalocyanine-based material having a phenoxy group is preferable. Specifically, a phthalocyanine derivative having a phenoxy group, such as PhO-VOPc, is preferable. The phthalocyanine derivative having a phenoxy group is soluble in a solvent and therefore has the advantage of being easy to handle during formation of a light-emitting element and the advantage of facilitating maintenance of an apparatus used for film formation.

The electron-relay layer 707 may further contain a donor substance. As the donor substance, an organic compound such as tetrathianaphthacene (abbreviation: TTN), nickelocene, or decamethylnickelocene can be used as well as an alkali metal, an alkaline earth metal, a rare earth metal, and a compound of the above metal (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)). When such a donor substance is contained in the electron-relay layer 707, electrons can be transferred easily and the light-emitting element can be driven at lower voltage.

In the case where a donor substance is contained in the electron-relay layer 707, other than the materials given above as the substance having a high electron-transport property, a substance having a LUMO level higher than the acceptor level of the acceptor substance contained in the composite material layer 708 can be used. Specifically, it is preferable to use a substance having a LUMO level higher than or equal to −5.0 eV, preferably higher than or equal to −5.0 eV and lower than or equal to −3.0 eV. As examples of such a substance, a perylene derivative, a nitrogen-containing condensed aromatic compound, and the like are given. Note that a nitrogen-containing condensed aromatic compound is preferably used for the electron-relay layer 707 because of its high stability.

Specific examples of the perylene derivative are 3,4,9,10-perylenetetracarboxylic dianhydride (abbreviation: PTCDA), 3,4,9,10-perylenetetracarboxylic-bis-benzimidazole (abbreviation: PTCBI), N,N'-dioctyl-3,4,9,10-perylenetetracarboxylic diimide (abbreviation: PTCDI-C8H), N,N'-dihexyl-3,4,9,10-perylenetetracarboxylic diimide (abbreviation: Hex PTC), and the like.

Specific examples of the nitrogen-containing condensed aromatic compound are pirazino[2,3-f][1,10]phenanthroline-2,3-dicarbonitrile (abbreviation: PPDN), 2,3,6,7,10,11-hexacyano-1,4,5,8,9,12-hexaazatriphenylene (abbreviation: $HAT(CN)_6$), 2,3-diphenylpyrido[2,3-b]pyrazine (abbreviation: 2PYPR), 2,3-bis(4-fluorophenyl)pyrido[2,3-b]pyrazine (abbreviation: F2PYPR), and the like.

Besides, 7,7,8,8-tetracyanoquinodimethane (abbreviation: TCNQ), 1,4,5,8-naphthalenetetracarboxylic dianhydride (abbreviation: NTCDA), perfluoropentacene, copper hexadecafluorophthalocyanine (abbreviation: $F_{16}CuPc$), N,N'-bis(2,2,3,3,4,4,5,5,6,6,7,7,8,8-pentadecafluorooctyl)-1,4,5,8-naphthalenetetracar boxylic diimide (abbreviation: NTCDI-C8F), 3',4'-dibutyl-5,5''-bis(dicyanomethylene)-5,5''-dihydro-2,2':5',2''-terthiophene (abbreviation: DCMT), methanofullerenes (e.g., [6,6]-phenyl $C_{61}$ butyric acid methyl ester), or the like can be used.

Note that in the case where a donor substance is contained in the electron-relay layer 707, the electron-relay layer 707 may be formed by a method such as co-evaporation of the substance having a high electron-transport property and the donor substance.

The hole-injection layer 701, the hole-transport layer 702, the light-emitting layer 703, and the electron-transport layer 704 may each be formed using the above-described materials.

As described above, the EL layer 102 of this embodiment can be formed.

In the above-described light-emitting element, a current flows due to a potential difference generated between the first electrode 103 and the second electrode 108 and holes and electrons recombine in the EL layer 102, so that light is emitted. Then, this light emission is extracted to the outside through either the first electrode 103 or the second electrode 108 or both. Therefore, either the first electrode 103 or the second electrode 108, or both, is an electrode having a property of transmitting visible light.

Note that the structure of layers provided between the first electrode 103 and the second electrode 108 is not limited to the above-described structure. A structure other than the above may alternatively be employed as long as a light-emitting region in which holes and electrons recombine is provided in a portion away from the first electrode 103 and the second electrode 108 so as to prevent quenching due to proximity of the light-emitting region to metal.

In other words, there is no particular limitation on a stack structure of the layers. A layer including a substance having a high electron-transport property, a substance having a high hole-transport property, a substance having a high electron-injection property, a substance having a high hole-injection property, a bipolar substance (a substance having a high electron-transport property and a high hole-transport property), a hole-blocking material, or the like may freely be combined with a light-emitting layer.

By use of the light-emitting element described in this embodiment, a passive matrix light-emitting device or an active matrix light-emitting device in which driving of the light-emitting element is controlled by a transistor can be manufactured. Furthermore, the light-emitting device can be applied to an electronic device, a lighting device, or the like.

In the above-described manner, the light-emitting element of one embodiment of the present invention can be manufactured.

Note that this embodiment can be combined with any of other embodiments as appropriate.

EXAMPLE 1

In this example, an example of a combination of a first organic compound, a second organic compound, and a phosphorescent compound which can be used for a light-emitting element of one embodiment of the present invention will be described with reference to FIGS. 1A and 1B.

The phosphorescent compound used in this example is bis(3,5-dimethyl-2-phenylpyrazinato)(dipivaloylmethanato)iridium(III) (abbreviation: [Ir(mppr-Me)$_2$(dpm)]). The first organic compound used in this example is 2-[3-(dibenzothiophen-4-yl)phenyl]dibenzo[f,h]quinoxaline (abbreviation: 2mDBTPDBq-II). The second organic compound used in this example is 4,4'-di(1-naphthyl)-4''-(9-phenyl-9H-carbazol-3-yl)triphenylamine (abbreviation: PCBNBB). Chemical formulae of the materials used in this example are shown below.

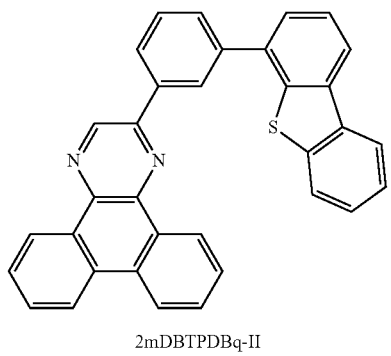

2mDBTPDBq-II

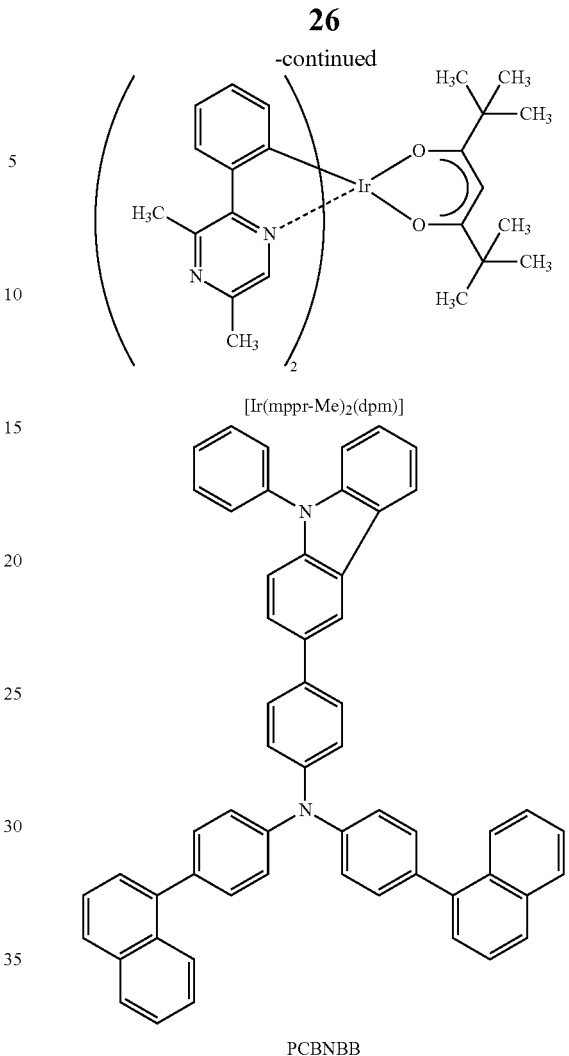

[Ir(mppr-Me)$_2$(dpm)]

PCBNBB

<Absorption Spectrum>

Figure 1B:
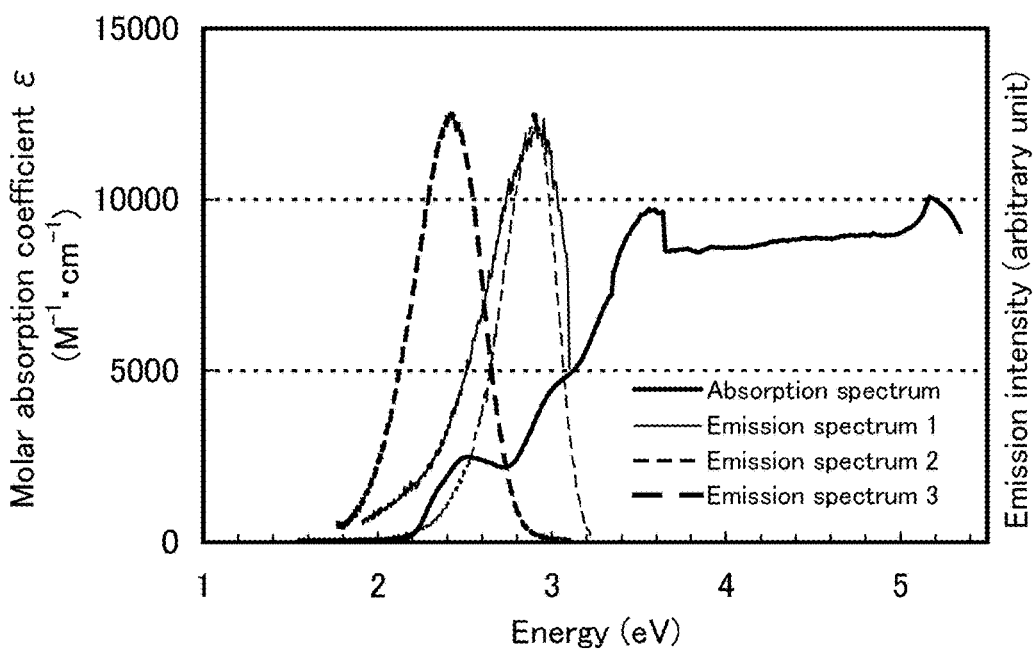

FIGS. 1A and 1B each show an ultraviolet-visible absorption spectrum (hereinafter, simply referred to as absorption spectrum) of [Ir(mppr-Me)$_2$(dpm)] that is the phosphorescent compound in a dichloromethane solution of [Ir(mppr-Me)$_2$(dpm)]. The absorption spectrum was measured with the use of an ultraviolet-visible light spectrophotometer (V-550, manufactured by JASCO Corporation) in the state where the dichloromethane solution (0.093 mmol/L) was put in a quartz cell at room temperature.

<Emission Spectrum>

FIGS. 1A and 1B each also show an emission spectrum of a thin film of 2mDBTPDBq-II that is the first organic compound (an emission spectrum 1), an emission spectrum of a thin film of PCBNBB that is the second organic compound (an emission spectrum 2), and an emission spectrum of a thin film of a mixed material of 2mDBTPDBq-II and PCBNBB (an emission spectrum 3). In FIG. 1A, the horizontal axis represents wavelength (nm), and the vertical axes represent molar absorption coefficient ε (M$^{-1}$·cm$^{-1}$) and emission intensity (arbitrary unit). In FIG. 1B, the horizontal axis represents energy (eV), and the vertical axes represent molar absorption coefficient ε (M$^{-1}$·cm$^{-1}$) and emission intensity (arbitrary unit).

As can be seen from the absorption spectrum in FIG. 1A, [Ir(mppr-Me)$_2$(dpm)] has a broad absorption band at around 520 nm. This absorption band is considered to greatly contribute to light emission.

The emission spectrum 3 peaks at a longer wavelength (lower energy) than the emission spectra 1 and 2. In addition, the peak of the emission spectrum 3 is closer to the absorption band than the peaks of the emission spectra 1 and 2. FIGS. 1A and 1B show that the emission spectrum 3 has the largest overlap with the absorption band in the absorption spectrum which greatly contributes to light emission. Specifically, the difference between the peak of the absorption band in the absorption spectrum (a shoulder peak at around 520 nm) and the peak of the emission spectrum 3 is 0.04 eV.

It is found that the emission spectrum of the mixed material of 2mDBTPDBq-II and PCBNBB peaks at a longer wavelength (lower energy) than the emission spectrum of either organic compound alone. This indicates that an exciplex is formed by mixing 2mDBTPDBq-II with PCBNBB.

It is found that the emission spectrum of the mixed material has a large overlap with the absorption band in the absorption spectrum of [Ir(mppr-Me)$_2$(dpm)] which is considered to greatly contribute to light emission. Thus, it is indicated that the light-emitting element including [Ir(mppr-Me)$_2$(dpm)] and the mixed material of 2mDBTPDBq-II and PCBNBB has high energy transfer efficiency because it transfers energy by utilizing the overlap between the emission spectrum of the mixed material and the absorption spectrum of the phosphorescent compound. Accordingly, it is indicated that a light-emitting element having high external quantum efficiency can be obtained.

EXAMPLE 2

In this example, an example of a combination of a first organic compound, a second organic compound, and a phosphorescent compound which can be used for a light-emitting element of one embodiment of the present invention will be described with reference to FIGS. 2A and 2B.

The phosphorescent compound used in this example is (acetylacetonato)bis(4,6-diphenylpyrimidinato)iridium(III) (abbreviation: [Ir(dppm)$_2$(acac)]). The first organic compound used in this example is 2mDBTPDBq-II. The second organic compound used in this example is PCBNBB. A chemical formula of the material used in this example is shown below. Note that the chemical formulae of the materials used in Example 1 are omitted here.

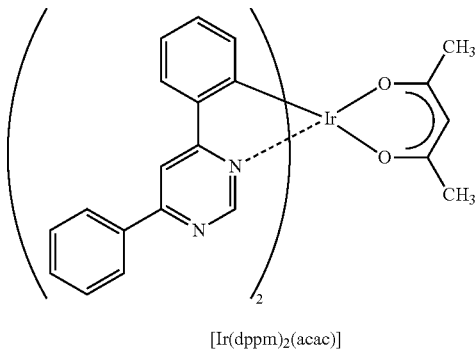

[Ir(dppm)$_2$(acac)]

<Absorption Spectrum>

Figure 2A:
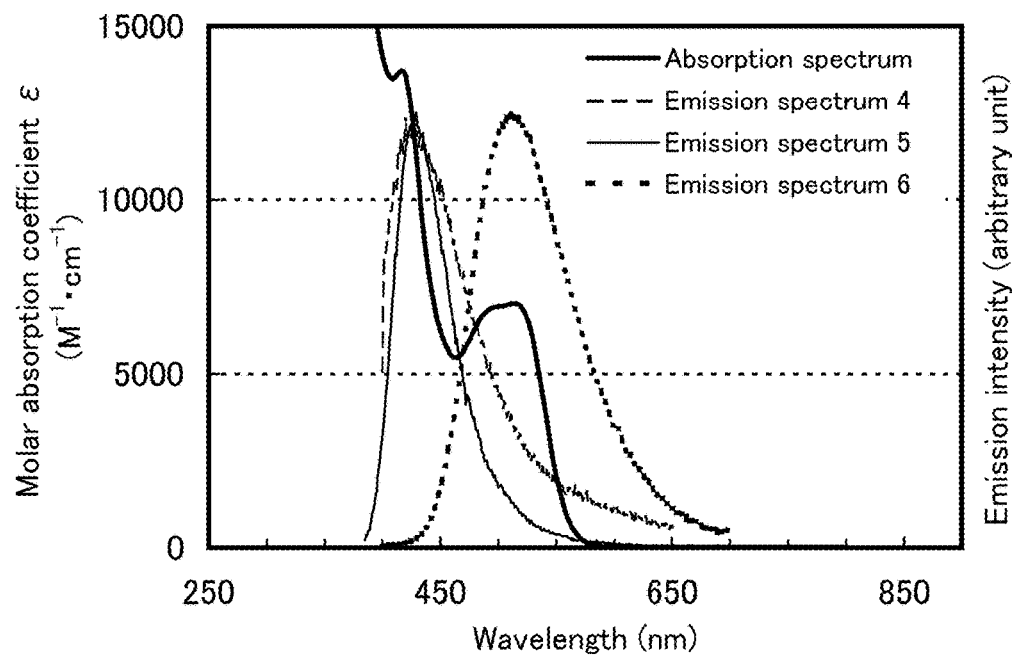
FIGS. 2A and 2B each show an absorption spectrum and emission spectrum according to Example 2.
Figure 2B:
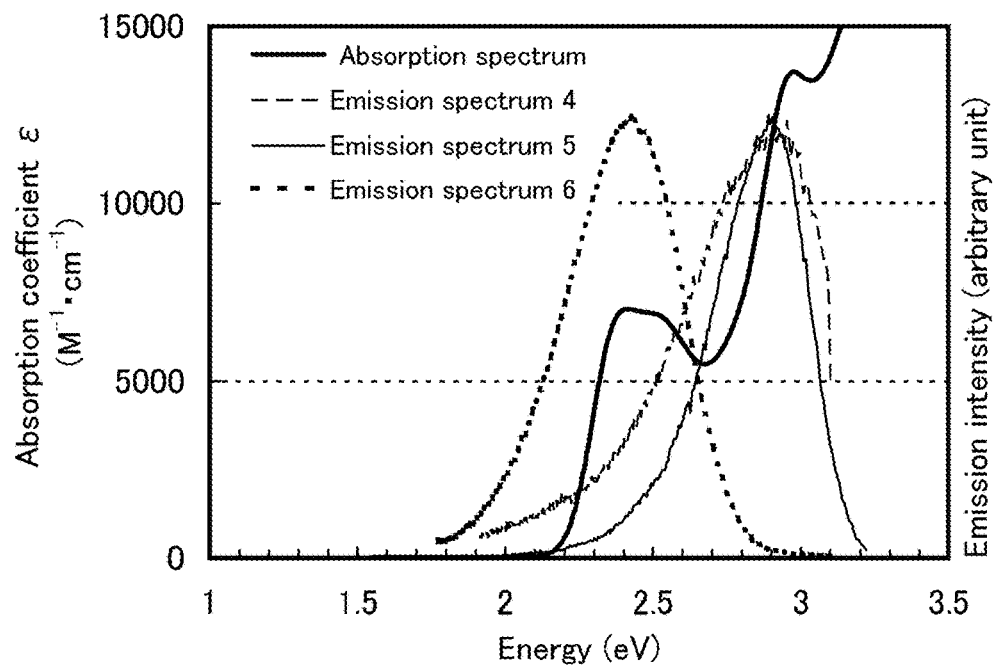

FIGS. 2A and 2B each show an ultraviolet-visible absorption spectrum (hereinafter, simply referred to as absorption spectrum) of [Ir(dppm)$_2$(acac)] that is the phosphorescent compound in a dichloromethane solution of [Ir(dppm)$_2$(acac)]. The absorption spectrum was measured with the use of an ultraviolet-visible light spectrophotometer (V-550, manufactured by JASCO Corporation) in the state where the dichloromethane solution (0.093 mmol/L) was put in a quartz cell at room temperature.

<Emission Spectrum>

FIGS. 2A and 2B each also show an emission spectrum of a thin film of 2mDBTPDBq-II that is the first organic compound (an emission spectrum 4), an emission spectrum of a thin film of PCNBB that is the second organic compound (an emission spectrum 5), and an emission spectrum of a thin film of a mixed material of 2mDBTPDBq-II and PCBNBB (an emission spectrum 6). In FIG. 2A, the horizontal axis represents wavelength (nm), and the vertical axes represent molar absorption coefficient ε (M$^{-1}$·cm$^{-1}$) and emission intensity (arbitrary unit). In FIG. 2B, the horizontal axis represents energy (eV), and the vertical axes represent molar absorption coefficient ε (M$^{-1}$·cm$^{-1}$) and emission intensity (arbitrary unit).

As can be seen from the absorption spectrum in FIG. 2A, [Ir(dppm)$_2$(acac)] has a broad absorption band at around 520 nm. This absorption band is considered to greatly contribute to light emission.

The emission spectrum 6 peaks at a longer wavelength (lower energy) than the emission spectra 4 and 5. In addition, the peak of the emission spectrum 6 is closer to the absorption band than the peaks of the emission spectra 4 and 5. FIGS. 2A and 2B show that the emission spectrum 6 has the largest overlap with the absorption band in the absorption spectrum which greatly contributes to light emission. Specifically, the difference between the peak (515 nm) of the absorption band in the absorption spectrum and the peak of the emission spectrum 6 is 0.02 eV.

It is found that the emission spectrum of the mixed material of 2mDBTPDBq-II and PCBNBB peaks at a longer wavelength (lower energy) than the emission spectrum of either organic compound alone. This indicates that an exciplex is formed by mixing 2mDBTPDBq-II with PCBNBB.

It is found that the peak of the emission spectrum of the mixed material has a large overlap with the absorption band in the absorption spectrum of [Ir(dppm)$_2$(acac)] which is considered to greatly contribute to light emission. Thus, it is indicated that the light-emitting element including [Ir(dppm)$_2$(acac)] and the mixed material of 2mDBTPDBq-II and PCBNBB has high energy transfer efficiency because it transfers energy by utilizing the overlap between the emission spectrum of the mixed material and the absorption spectrum of the phosphorescent compound. Accordingly, it is indicated that a light-emitting element having high external quantum efficiency can be obtained.

EXAMPLE 3

Figure 15:
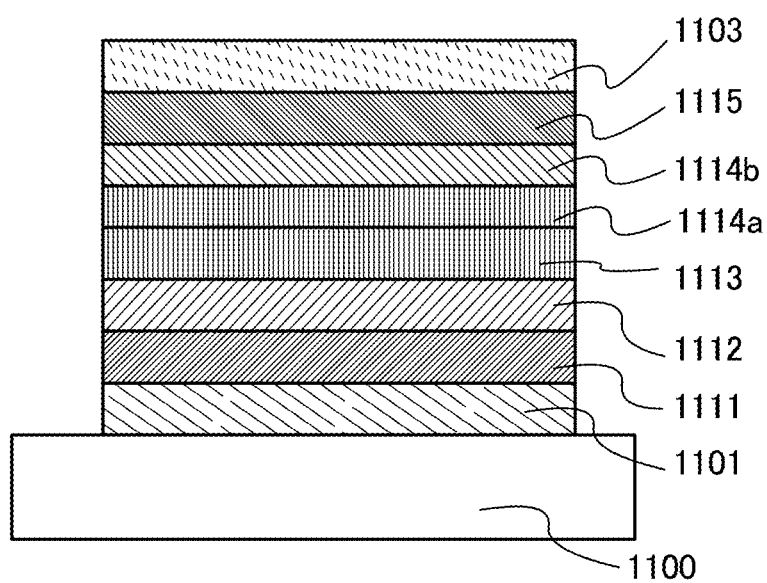
FIG. 15 shows the structure of light-emitting elements of examples.

In this example, a light-emitting element of one embodiment of the present invention will be described with reference to FIG. 15. Chemical formulae of materials used in this example are shown below. Note that the chemical formulae of the materials used in the above examples are omitted here.

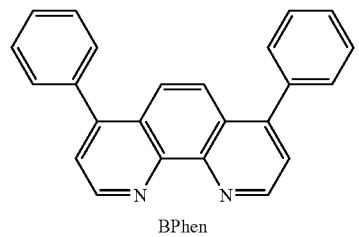

BPhen

-continued

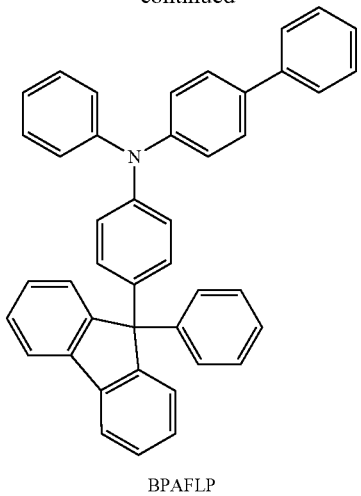

BPAFLP

Methods for manufacturing a light-emitting element 1 of this example and a comparative light-emitting element 2 will be described below.

(Light-emitting Element 1)

First, a film of indium tin oxide containing silicon oxide (ITSO) was formed over a glass substrate 1100 by a sputtering method, so that a first electrode 1101 functioning as an anode was formed. Note that the thickness was set to 110 nm and the electrode area was set to 2 mm×2 mm.

Next, as pretreatment for forming the light-emitting element over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, 4-phenyl-4'-(9-phenylfluoren-9-yl)triphenylamine (abbreviation: BPAFLP) and molybdenum(VI) oxide were co-evaporated to form a hole-injection layer 1111 over the first electrode 1101. The thickness of the hole-injection layer

1111 was set to 40 nm, and the weight ratio of BPAFLP to molybdenum oxide was adjusted to 4:2 (=BPAFLP:molybdenum oxide).

Next, over the hole-injection layer 1111, a film of BPAFLP was formed to a thickness of 20 nm to form a hole-transport layer 1112.

Furthermore, 2mDBTPDBq-II, PCBNBB, and [Ir(mppr-Me)$_2$(dpm)] were co-evaporated to form a light-emitting layer 1113 over the hole-transport layer 1112. Here, the weight ratio of 2mDBTPDBq-II to PCBNBB and [Ir(mppr-Me)$_2$(dpm)] was adjusted to 0.8:0.2:0.05 (=2mDBTPDBq-II:PCBNBB:[Ir(mppr-Me)$_2$(dpm)]). The thickness of the light-emitting layer 1113 was set to 40 nm.

Further, over the light-emitting layer 1113, a film of 2mDBTPDBq-II was formed to a thickness of 10 nm to form a first electron-transport layer 1114a.

Next, over the first electron-transport layer 1114a, a film of bathophenanthroline (abbreviation: BPhen) was formed to a thickness of 20 nm to form a second electron-transport layer 1114b.

Further, over the second electron-transport layer 1114b, a film of lithium fluoride (LiF) was formed by evaporation to a thickness of 1 nm to form an electron-injection layer 1115.

Lastly, an aluminum film was formed by evaporation to a thickness of 200 nm as a second electrode 1103 functioning as a cathode. Thus, the light-emitting element 1 of this example was fabricated.

(Comparative Light-emitting Element 2)

A light-emitting layer 1113 of the comparative light-emitting element 2 was formed by co-evaporating 2mDBTPDBq-II and [Ir(mppr-Me)$_2$(dpm)]. Here, the weight ratio of 2mDBTPDBq-II to [Ir(mppr-Me)$_2$(dpm)] was adjusted to 1:0.05 (=2mDBTPDBq-II:[Ir(mppr-Me)$_2$(dpm)]). The thickness of the light-emitting layer 1113 was set to 40 nm. Components other than the light-emitting layer 1113 were manufactured in a manner similar to that of the light-emitting element 1.

Note that, in all the above evaporation steps, evaporation was performed by a resistance-heating method.

Table 1 shows element structures of the light-emitting element 1 and the comparative light-emitting element 2 obtained as described above.

TABLE 1

| | first elecrtrode | hole-injection layer | hole-transport layer | light-emitting layer | first electron-transport layer | second electron-transport layer | electron-injection layer | second electrode |
|---|---|---|---|---|---|---|---|---|
| light-emitting element 1 | ITSO 110 nm | BPAFLP:MoOx (=4:2) 40 nm | BPAFLP 20 nm | 2mDBTPDBq-II:PCBNBB:[Ir(mppr-Me)$_2$(dpm)] (=0.8:0.2:0.05) 40 nm | 2mDBTPDBq-II 10 nm | BPhen 20 nm | LiF 1 nm | Al 200 nm |
| comparative light-emitting element 2 | ITSO 110 nm | BPAFLP:MoOx (=4:2) 40 nm | BPAFLP 20 nm | 2mDBTPDBq-II:[Ir(mppr-Me)$_2$(dpm)] (=1:0.05) 40 nm | 2mDBTPDBq-II 10 nm | BPhen 20 nm | LiF 1 nm | Al 200 nm |

In a glove box containing a nitrogen atmosphere, these light-emitting elements were sealed so as not to be exposed to air. Then, operation characteristics of these light-emitting elements were measured. Note that the measurements were carried out at room temperature (in the atmosphere kept at 25° C.).

Figure 3:
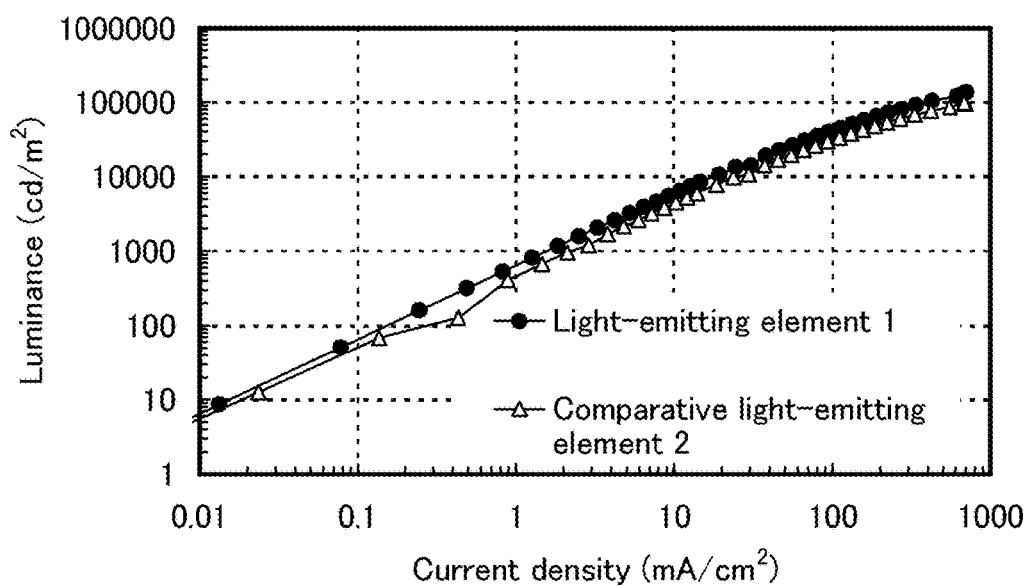
FIG. 3 shows current density-luminance characteristics of a light-emitting element of Example 3.
Figure 4:
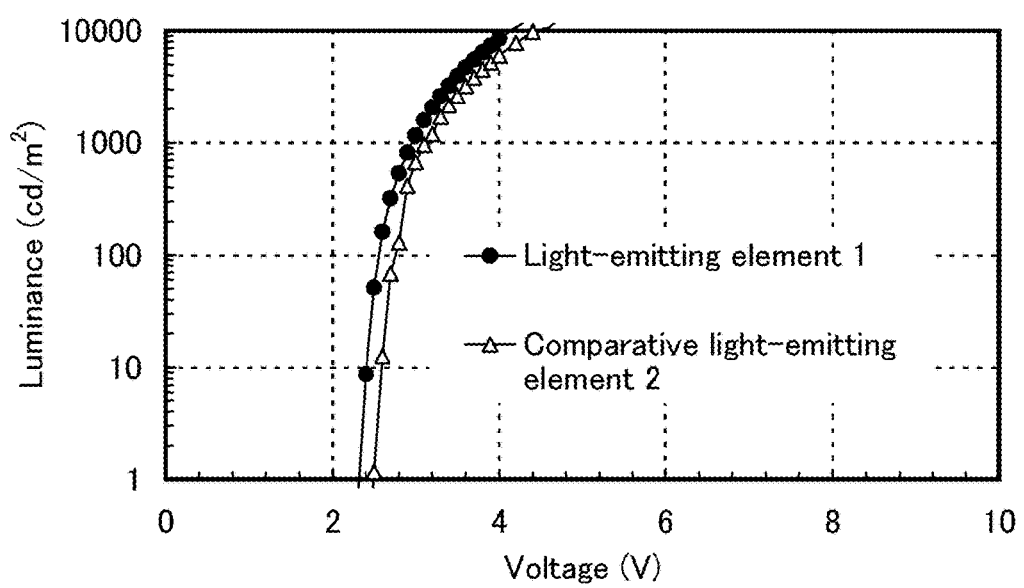
FIG. 4 shows voltage-luminance characteristics of the light-emitting element of Example 3.
Figure 5:
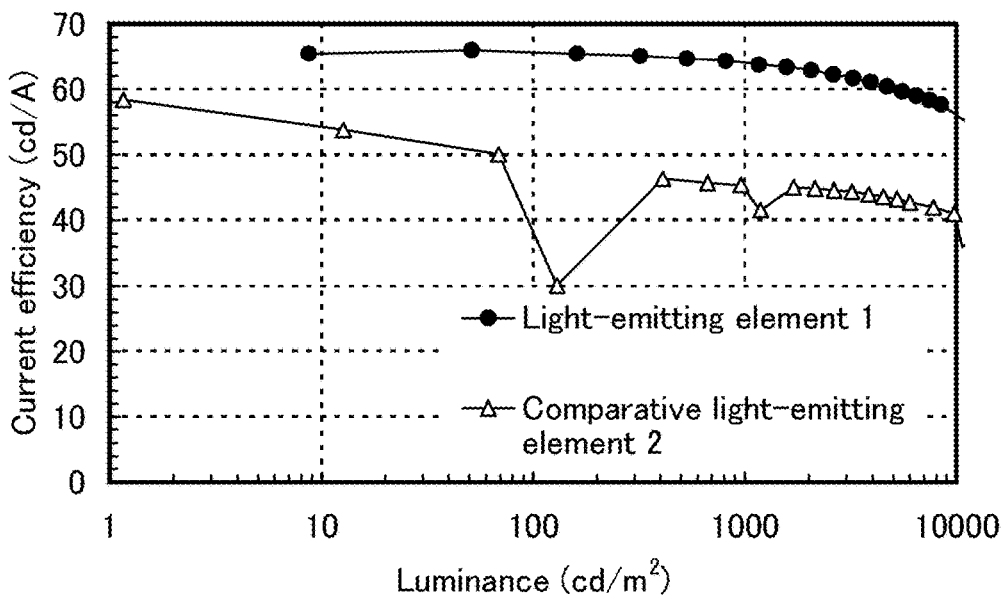
FIG. 5 shows luminance-current efficiency characteristics of the light-emitting element of Example 3.
Figure 6:
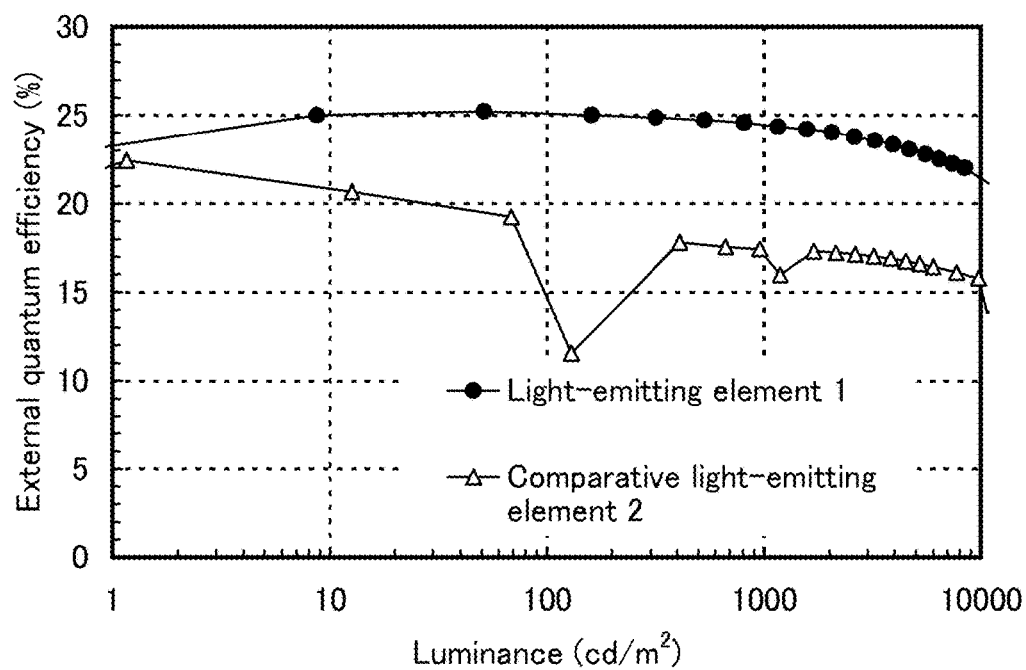
FIG. 6 shows luminance-external quantum efficiency characteristics of the light-emitting element of Example 3.

FIG. 3 shows current density-luminance characteristics of the light-emitting element 1 and the comparative light-emitting element 2. In FIG. 3, the horizontal axis represents current density (mA/cm$^2$), and the vertical axis represents luminance (cd/m$^2$). FIG. 4 shows voltage-luminance characteristics thereof. In FIG. 4, the horizontal axis represents voltage (V), and the vertical axis represents luminance (cd/m$^2$). FIG. 5 shows luminance-current efficiency characteristics thereof. In FIG. 5, the horizontal axis represents luminance (cd/m$^2$), and the vertical axis represents current efficiency (cd/A). FIG. 6 shows luminance-external quantum efficiency characteristics thereof. In FIG. 6, the horizontal axis represents luminance (cd/m$^2$), and the vertical axis represents external quantum efficiency (%).

Further, Table 2 shows the voltage (V), current density (mA/cm$^2$), CIE chromaticity coordinates (x, y), current efficiency (cd/A), power efficiency (lm/W), and external quantum efficiency (%) of each of the light-emitting element 1 and the comparative light-emitting element 2 at a luminance of around 1000 cd/m$^2$.

TABLE 2

| | voltage (V) | current density (mA/cm$^2$) | chromaticity coordinates (x, y) | luminance (cd/m$^2$) | current efficiency (cd/A) | power efficiency (lm/W) | external quantum efficiency (%) |
|---|---|---|---|---|---|---|---|
| light-emitting element 1 | 3.0 | 1.8 | (0.56, 0.44) | 1200 | 64 | 67 | 24 |
| comparative light-emitting element 2 | 3.1 | 2.1 | (0.55, 0.44) | 960 | 45 | 46 | 17 |

Figure 7:
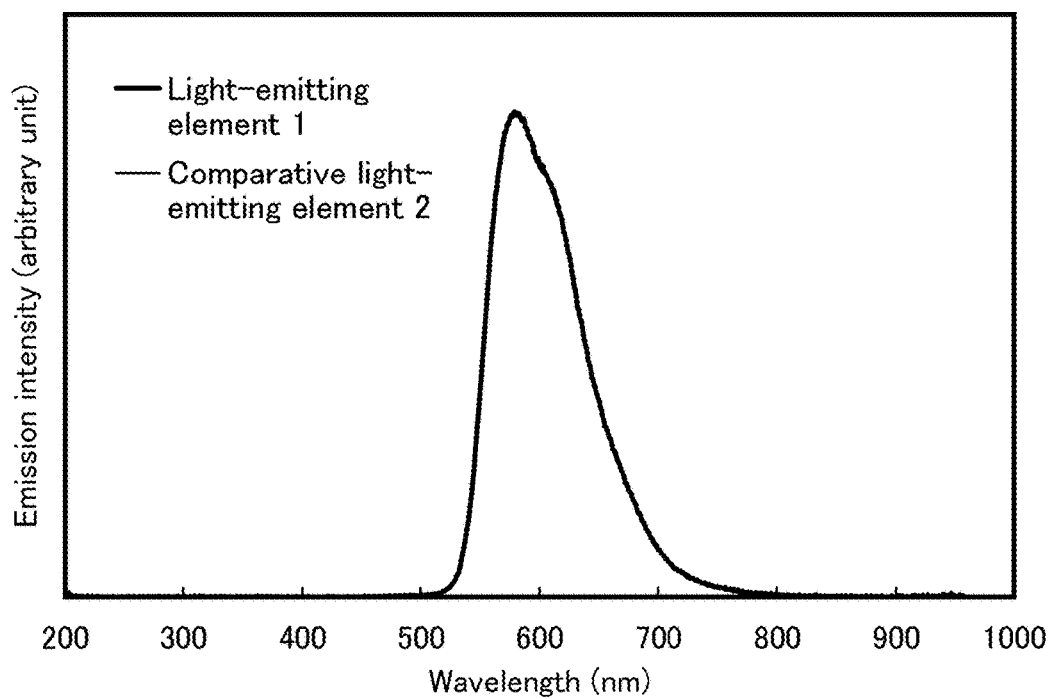
FIG. 7 shows an emission spectrum of the light-emitting element of Example 3.

FIG. 7 shows emission spectra of the light-emitting element 1 and the comparative light-emitting element 2 which were obtained by applying a current of 0.1 mA. In FIG. 7, the horizontal axis represents wavelength (nm), and the vertical axis represents emission intensity (arbitrary unit). As shown in Table 2, the CIE chromaticity coordinates of the light-emitting element 1 at a luminance of 1200 cd/m$^2$ were (x, y)=(0.56, 0.44), and the CIE chromaticity coordinates of the comparative light-emitting element 2 at a luminance of 960 cd/m$^2$ were (x, y)=(0.55, 0.44). These results show that orange light emission originating from [Ir(mppr-Me)$_2$(dpm)] was obtained from the light-emitting element 1 and the comparative light-emitting element 2.

As can be seen from Table 2 and FIGS. 3 to 6, the light-emitting element 1 has higher current efficiency, higher power efficiency, and higher external quantum efficiency than the comparative light-emitting element 2.

In the light-emitting element 1 of this example, 2mDBTPDBq-II, PCBNBB, and [Ir(mppr-Me)$_2$(dpm)] described in Example 1 are used for the light-emitting layer. As described in Example 1, the emission spectrum of the mixed material of 2mDBTPDBq-II and PCBNBB (the emission spectrum of an exciplex) has a larger overlap with the absorption spectrum of [Ir(mppr-Me)$_2$(dpm)] as compared with the emission spectrum of 2mDBTPDBq-II or PCBNBB alone. The light-emitting element 1 of this example is considered to have high energy transfer efficiency because it transfers energy by utilizing the overlap, and therefore have higher external quantum efficiency than the comparative light-emitting element 2.

The above results show that an element having high external quantum efficiency can be obtained by application of one embodiment of the present invention.

Figure 8:
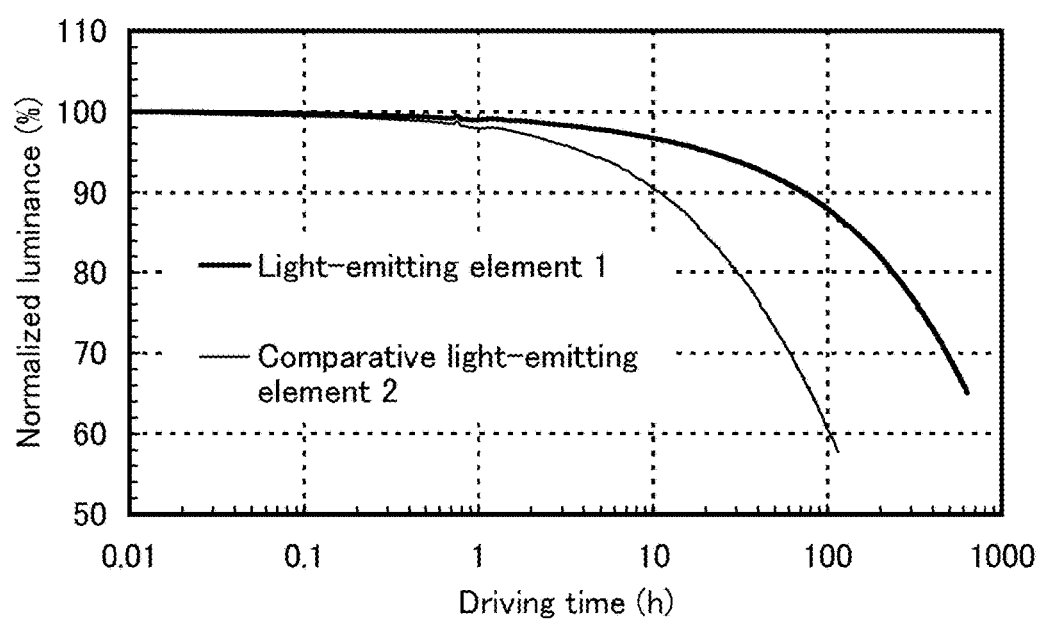
FIG. 8 shows results of reliability tests of the light-emitting element of Example 3.

Next, the light-emitting element 1 and the comparative light-emitting element 2 were subjected to reliability tests. Results of the reliability tests are shown in FIG. 8. In FIG. 8, the vertical axis represents normalized luminance (%) with an initial luminance of 100%, and the horizontal axis represents driving time (h) of the elements.

In the reliability tests, the light-emitting element 1 and the comparative light-emitting element 2 were driven under the conditions where the initial luminance was set to 5000 cd/m$^2$ and the current density was constant.

The luminance of the comparative light-emitting element 2 after 120 hours was 58% of the initial luminance. The luminance of the light-emitting element 1 after 630 hours was 65% of the initial luminance. From the results, the light-emitting element 1 is found to have a longer lifetime than the comparative light-emitting element 2.

The above results show that an element having high reliability can be obtained by application of one of the present invention.

EXAMPLE 4

In this example, a light-emitting element of one embodiment of the present invention will be described with reference to FIG. 15. The materials used in this example are used in the above examples, and therefore the chemical formulae thereof are omitted here.

A method for manufacturing a light-emitting element 3 of this example will be described below.

(Light-emitting Element 3)

First, a film of ITSO was formed over a glass substrate 1100 by a sputtering method, so that a first electrode 1101 functioning as an anode was formed. Note that the thickness was set to 110 nm and the electrode area was set to 2 mm×2 mm.

Next, as pretreatment for forming the light-emitting element over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately 10$^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about 10$^{-4}$ Pa. Then, BPAFLP and molybdenum(VI) oxide were co-evaporated to form a hole-injection layer 1111 over the first electrode 1101. The thickness of the hole-injection layer 1111 was set to 40 nm, and the weight ratio of BPAFLP to molybdenum oxide was adjusted to 4:2 (=BPAFLP:molybdenum oxide).

Next, over the hole-injection layer 1111, a film of BPAFLP was formed to a thickness of 20 nm to form a hole-transport layer 1112.

Furthermore, 2mDBTPDBq-II, PCBNBB, and [Ir(dppm)$_2$(acac)] were co-evaporated to form a light-emitting layer 1113 over the hole-transport layer 1112. Here, the weight ratio of 2mDBTPDBq-II to PCBNBB and [Ir(dppm)$_2$(acac)] was adjusted to 0.8:0.2:0.05 (=2mDBTPDBq-II:PCBNBB:[Ir(dppm)$_2$(acac)]). The thickness of the light-emitting layer 1113 was set to 40 nm.

Further, over the light-emitting layer 1113, a film of 2mDBTPDBq-II was formed to a thickness of 10 nm to form a first electron-transport layer 1114a.

Next, over the first electron-transport layer 1114a, a film of BPhen was formed to a thickness of 20 nm to form a second electron-transport layer 1114b.

Further, over the second electron-transport layer 1114b, a film of LiF was formed by evaporation to a thickness of 1 nm to form an electron-injection layer 1115.

Lastly, an aluminum film was formed by evaporation to a thickness of 200 nm as a second electrode 1103 functioning as a cathode. Thus, the light-emitting element 3 of this example was fabricated.

Note that, in all the above evaporation steps, evaporation was performed by a resistance-heating method.

Table 3 shows an element structure of the light-emitting element 3 obtained as described above.

Figure 13:
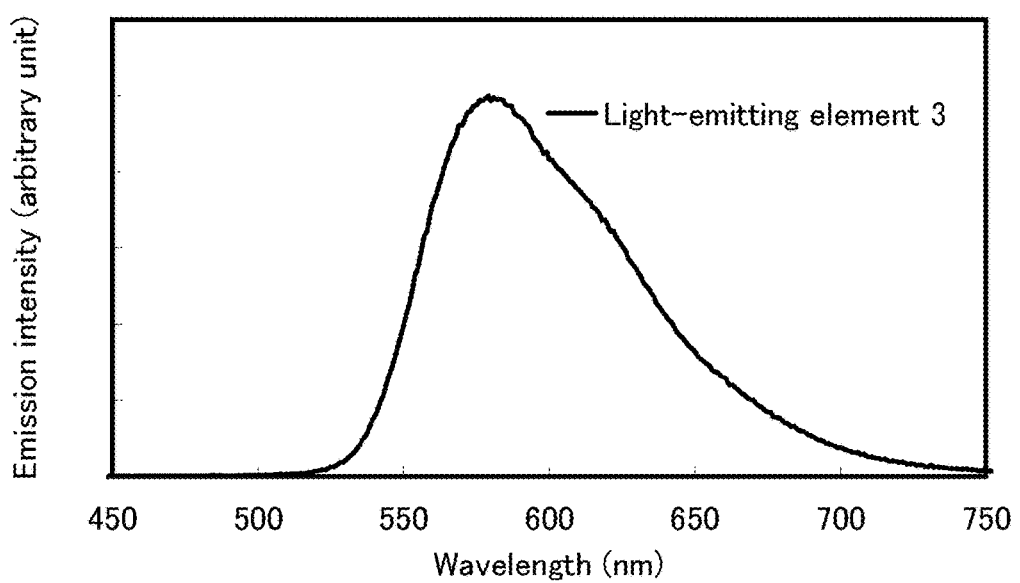
FIG. 13 shows an emission spectrum of the light-emitting element of Example 4.

FIG. 13 shows an emission spectrum of the light-emitting element 3 which was obtained by applying a current of 0.1 mA. In FIG. 13, the horizontal axis represents wavelength (nm), and the vertical axis represents emission intensity (arbitrary unit). As shown in Table 4, the CIE chromaticity coordinates of the light-emitting element 3 at a luminance of 1100 cd/m$^2$ were (x, y)=(0.54, 0.46). These results show that orange light emission originating from [Ir(dppm)$_2$(acac)] was obtained from the light-emitting element 3.

As can be seen from Table 4 and FIGS. 9 to 12, the light-emitting element 3 has high current efficiency, high power efficiency, and high external quantum efficiency. In particular, the light-emitting element 3 has an extremely high external quantum efficiency of 28% at a luminance of 1100 cd/m$^2$. As described above, the upper limit of external quantum efficiency is said to be around 25%. However, the result of the external quantum efficiency this time is above the limit.

In the light-emitting element of this example, 2mDBTPDBq-II, PCBNBB, and [Ir(dppm)$_2$(acac)] described in Example 2 are used for the light-emitting layer. As described

TABLE 3

| | first elecrtrode | hole-injection layer | hole-transport layer | light-emitting layer | first electron-transport layer | second electron-transport layer | electron-injection layer | second electrode |
|---|---|---|---|---|---|---|---|---|
| light-emitting element 3 | ITSO 110 nm | BPAFLP:MoOx (=4:2) 40 nm | BPAFLP 20 nm | 2mDBTPDBq-II:PCBNBB:[Ir(dppm)$_2$(acac)] (=0.8:0.2:0.05) 40 nm | 2mDBTPDBq-II 10 nm | BPhen 20 nm | LiF 1 nm | Al 200 nm |

In a glove box containing a nitrogen atmosphere, the light-emitting element 3 was sealed so as not to be exposed to air. Then, operation characteristics of the light-emitting element were measured. Note that the measurements were carried out at room temperature (in the atmosphere kept at 25° C.).

Figure 9:
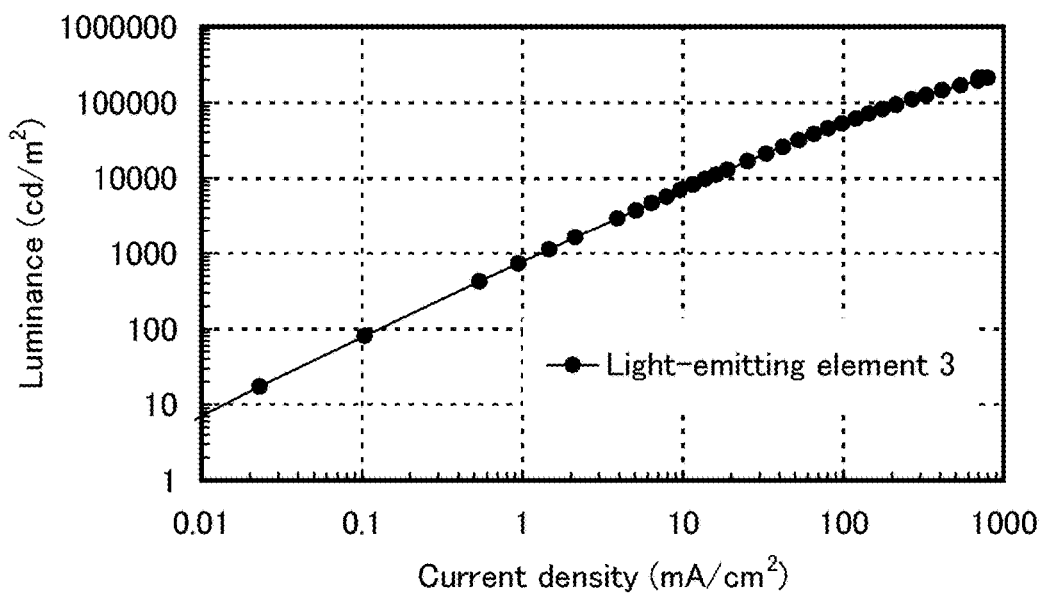
FIG. 9 shows current density-luminance characteristics of a light-emitting element of Example 4.
Figure 10:
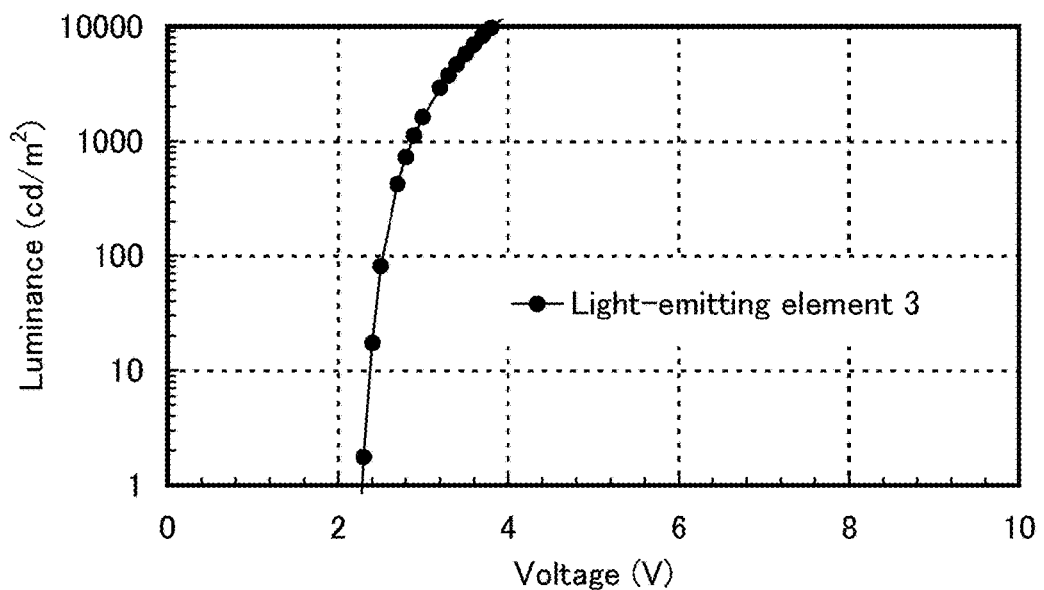
FIG. 10 shows voltage-luminance characteristics of the light-emitting element of Example 4.
Figure 11:
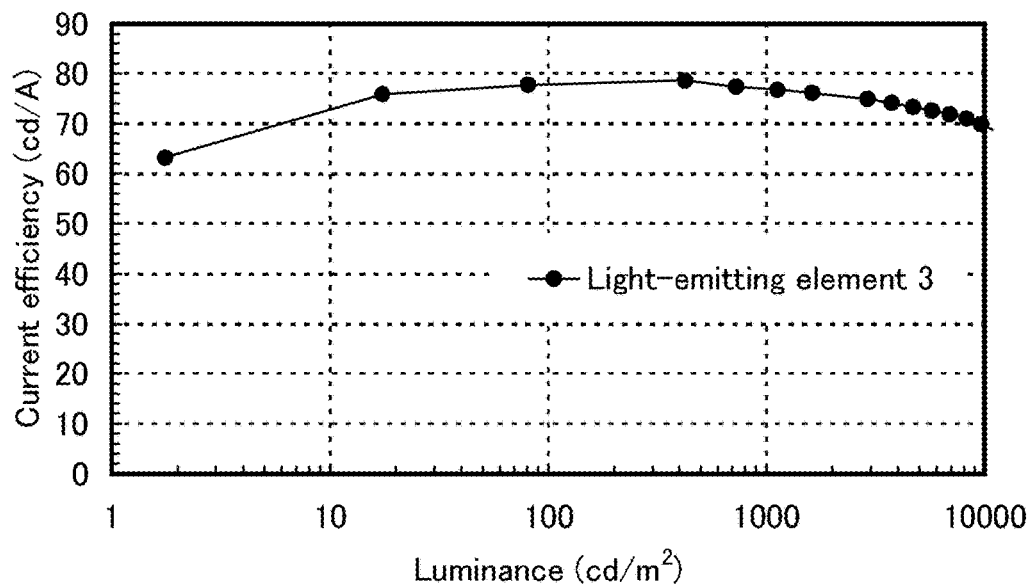
FIG. 11 shows luminance-current efficiency characteristics of the light-emitting element of Example 4.
Figure 12:
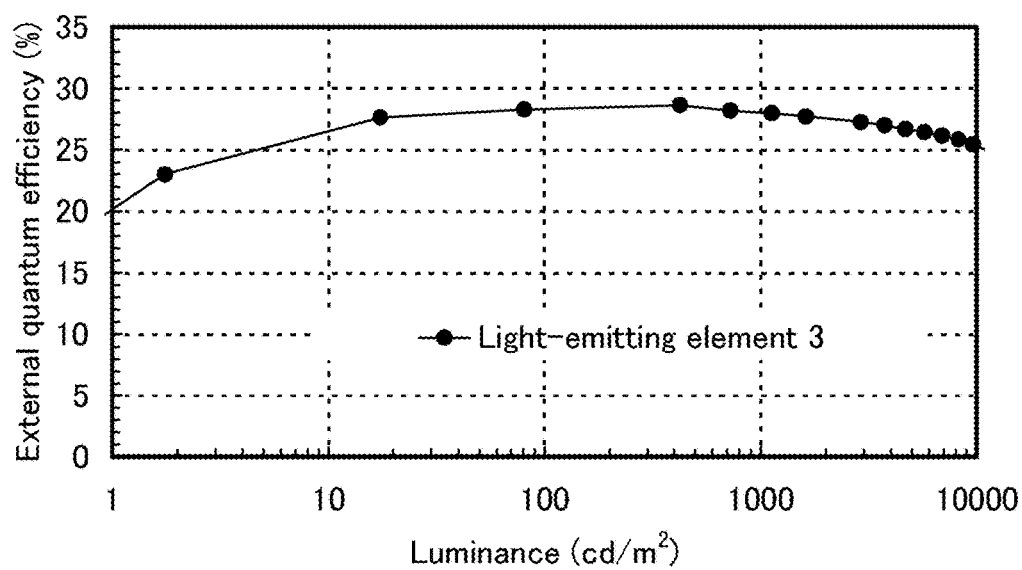
FIG. 12 shows luminance-external quantum efficiency characteristics of the light-emitting element of Example 4.

FIG. 9 shows current density-luminance characteristics of the light-emitting element 3. In FIG. 9, the horizontal axis represents current density (mA/cm$^2$), and the vertical axis represents luminance (cd/m$^2$). FIG. 10 shows voltage-luminance characteristics thereof. In FIG. 10, the horizontal axis represents voltage (V), and the vertical axis represents luminance (cd/m$^2$). FIG. 11 shows luminance-current efficiency characteristics thereof. In FIG. 11, the horizontal axis represents luminance (cd/m$^2$), and the vertical axis represents current efficiency (cd/A). FIG. 12 shows luminance-external quantum efficiency characteristics thereof. In FIG. 12, the horizontal axis represents luminance (cd/m$^2$), and the vertical axis represents external quantum efficiency (%).

Further, Table 4 shows the voltage (V), current density (mA/cm$^2$), CIE chromaticity coordinates (x, y), current efficiency (cd/A), power efficiency (lm/W), and external quantum efficiency (%) of the light-emitting element 3 at a luminance of 1100 cd/m$^2$.

in Example 2, the emission spectrum of the mixed material of 2mDBTPDBq-II and PCBNBB (the emission spectrum of an exciplex) has a larger overlap with the absorption spectrum of [Ir(dppm)$_2$(acac)] as compared with the emission spectrum of 2mDBTPDBq-II or PCBNBB alone. The light-emitting element of this example is considered to have high energy transfer efficiency because it transfers energy by utilizing the overlap, and therefore have unprecedentedly high external quantum efficiency.

The results of Example 2 show that a peak of the absorption band on the longest wavelength side in the absorption spectrum of the guest material used in the light-emitting element 3 is close to a peak of the emission spectrum, and that the molar absorption coefficient at the peak is high (>5000 M$^{-1}$·cm$^{-1}$). From these results, the light-emitting element 3 is considered to have particularly high energy transfer efficiency and therefore have unprecedentedly high external quantum efficiency.

The above results show that an element having high external quantum efficiency can be obtained by application of one embodiment of the present invention.

Next, the light-emitting element 3 was subjected to reliability tests. Results of the reliability tests are shown in FIG.

TABLE 4

| | voltage (V) | current density (mA/cm$^2$) | chromaticity coordinates (x, y) | current efficiency (cd/A) | power efficiency (lm/W) | external quantum efficiency (%) |
|---|---|---|---|---|---|---|
| light-emitting element 3 | 2.9 | 1.5 | (0.54, 0.46) | 77 | 83 | 28 |

Figure 14:
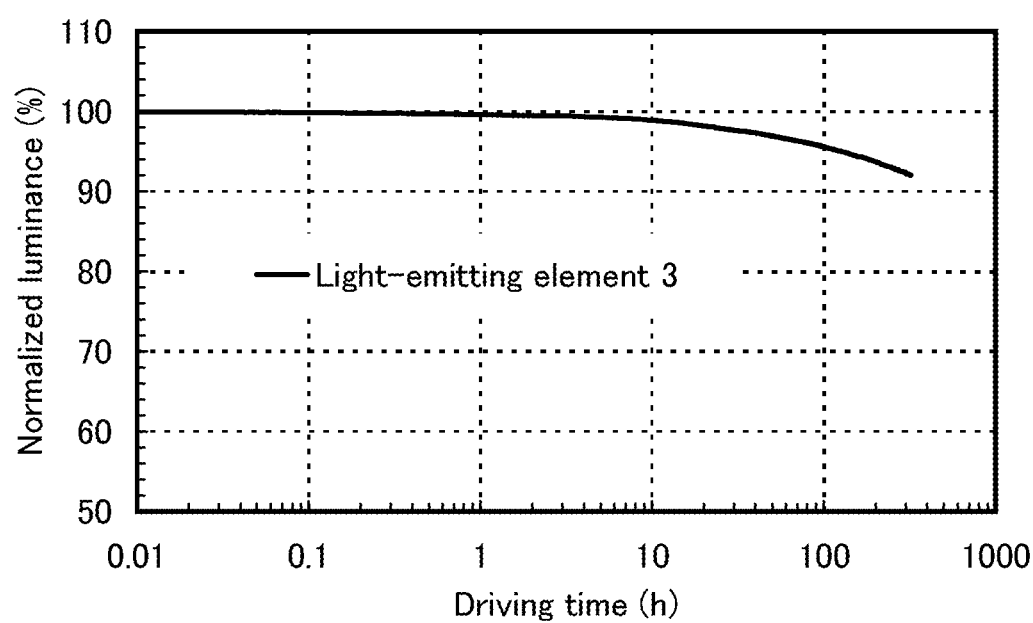
FIG. 14 shows results of reliability tests of the light-emitting element of Example 4.

14. In FIG. 14, the vertical axis represents normalized luminance (%) with an initial luminance of 100%, and the horizontal axis represents driving time (h) of the elements.

In the reliability tests, the light-emitting element 3 was driven under the conditions where the initial luminance was set to 5000 cd/m² and the current density was constant.

The light-emitting element 3 kept 92% of the initial luminance after the driving for 320 hours.

The above results show that an element having high reliability can be obtained by application of one embodiment of the present invention.

EXAMPLE 5

In this example, an example of a combination of a first organic compound, a second organic compound, and a phosphorescent compound which can be used for a light-emitting element of one embodiment of the present invention will be described with reference to FIGS. 18A and 18B.

The phosphorescent compound used in this example is [Ir(dppm)$_2$(acac)]. The first organic compound used in this example is 2mDBTPDBq-II. The second organic compound used in this example is 4-phenyl-4'-(9-phenyl-9H-carbazol-3-yl)triphenylamine (abbreviation: PCBA1BP). A chemical formula of the material used in this example is shown below. Note that the chemical formulae of the materials used in the above examples are omitted here.

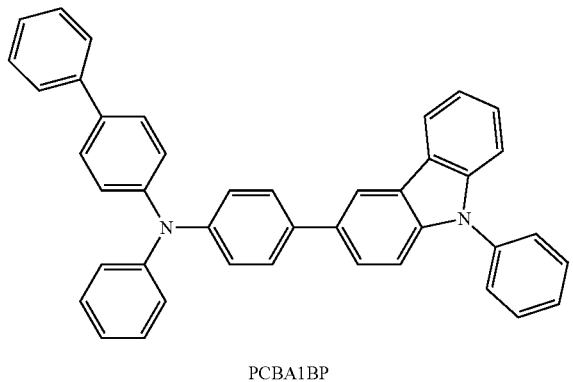 [SMILES: c1ccc(-c2ccc(N(c3ccccc3)c3ccc(-c4ccc5c(c4)c4ccccc4n5-c4ccccc4)cc3)cc2)cc1]

PCBA1BP

<Absorption Spectrum>

Figure 18A:
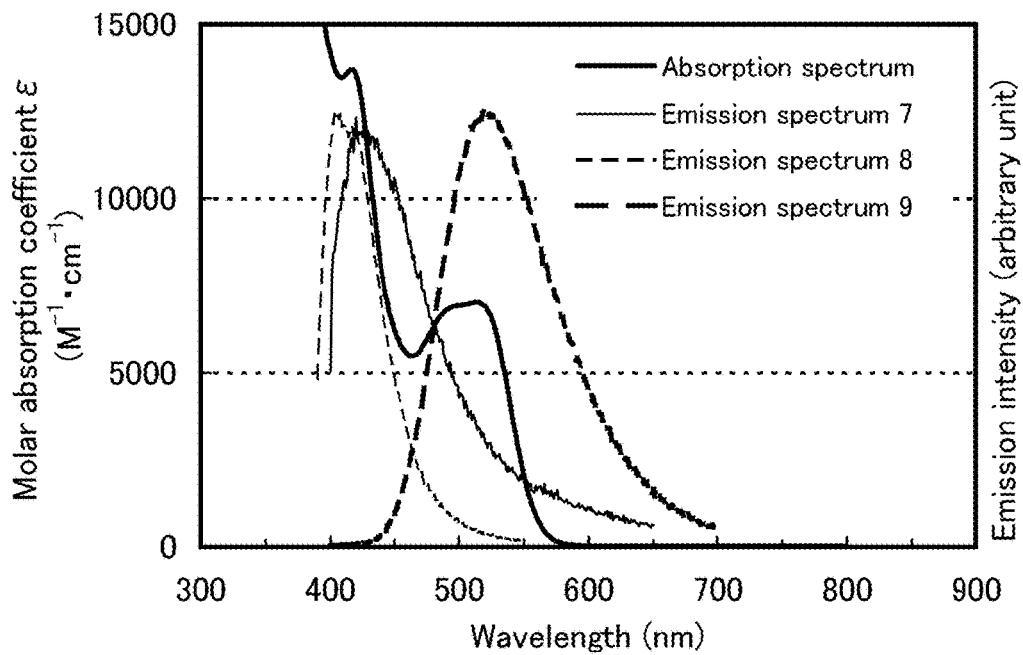
FIGS. 18A and 18B each show an absorption spectrum and emission spectra according to Example 5.
Figure 18B:
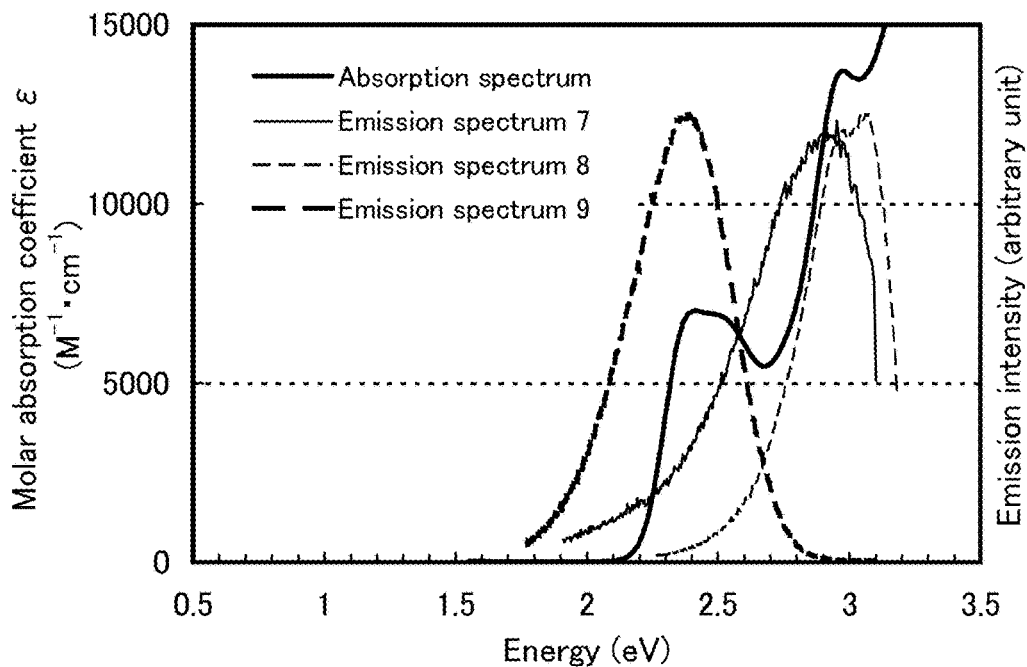

FIGS. 18A and 18B each show an ultraviolet-visible absorption spectrum (hereinafter, simply referred to as absorption spectrum) of [Ir(dppm)$_2$(acac)] that is the phosphorescent compound in a dichloromethane solution of [Ir(dppm)$_2$(acac)]. The absorption spectrum was measured with the use of an ultraviolet-visible light spectrophotometer (V-550, manufactured by JASCO Corporation) in the state where the dichloromethane solution (0.093 mmol/L) was put in a quartz cell at room temperature.

<Emission Spectrum>

FIGS. 18A and 18B each also show an emission spectrum of a thin film of 2mDBTPDBq-II that is the first organic compound (an emission spectrum 7), an emission spectrum of a thin film of PCBA1BP that is the second organic compound (an emission spectrum 8), and an emission spectrum of a thin film of a mixed material of 2mDBTPDBq-II and PCBA1BP (an emission spectrum 9). In FIG. 18A, the horizontal axis represents wavelength (nm), and the vertical axes represent molar absorption coefficient ε (M$^{-1}$·cm$^{-1}$) and emission intensity (arbitrary unit). In FIG. 18B, the horizontal axis represents energy (eV), and the vertical axes represent molar absorption coefficient ε (M$^{-1}$·cm$^{-1}$) and emission intensity (arbitrary unit).

As can be seen from the absorption spectrum in FIG. 18A, [Ir(dppm)$_2$(acac)] has a broad absorption band at around 520 nm. This absorption band is considered to greatly contribute to light emission.

The emission spectrum 9 peaks at a longer wavelength (lower energy) than the emission spectra 7 and 8. In addition, the peak of the emission spectrum 9 is closer to the absorption band than the peaks of the emission spectra 7 and 8. FIGS. 18A and 18B show that the emission spectrum 9 has the largest overlap with the absorption band in the absorption spectrum which greatly contributes to light emission. Specifically, the difference between the peak (515 nm) of the absorption band in the absorption spectrum and the peak of the emission spectrum 9 is 0.02 eV.

It is found that the emission spectrum of the mixed material of 2mDBTPDBq-II and PCBA1BP peaks at a longer wavelength (lower energy) than the emission spectrum of either organic compound alone. This indicates that an exciplex is formed by mixing 2mDBTPDBq-II with PCBA1BP.

It is found that the peak of the emission spectrum of the mixed material has a large overlap with the absorption band in the absorption spectrum of [Ir(dppm)$_2$(acac)] which is considered to greatly contribute to light emission. Thus, it is indicated that the light-emitting element including [Ir(dppm)$_2$(acac)] and the mixed material of 2mDBTPDBq-II and PCBA1BP has high energy transfer efficiency because it transfers energy by utilizing the overlap between the emission spectrum of the mixed material and the absorption spectrum of the phosphorescent compound. Accordingly, it is indicated that a light-emitting element having high external quantum efficiency can be obtained.

EXAMPLE 6

In this example, a light-emitting element of one embodiment of the present invention will be described with reference to FIG. 15. The materials used in this example are used in the above examples, and therefore the chemical formulae thereof are omitted here.

A method for manufacturing a light-emitting element 4 of this example will be described below.

(Light-emitting Element 4)

First, a film of ITSO was formed over a glass substrate 1100 by a sputtering method, so that a first electrode 1101 functioning as an anode was formed. Note that the thickness was set to 110 nm and the electrode area was set to 2 mm×2 mm.

Next, as pretreatment for forming the light-emitting element over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately 10$^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about 10$^{-4}$ Pa. Then, BPAFLP and molybdenum(VI) oxide were co-evaporated to form a hole-injection layer 1111 over the first electrode 1101. The thickness of the hole-injection layer 1111 was set to 40 nm, and the weight ratio of BPAFLP to molybdenum oxide was adjusted to 4:2 (=BPAFLP:molybdenum oxide).

Next, over the hole-injection layer 1111, a film of BPAFLP was formed to a thickness of 20 nm to form a hole-transport layer 1112.

Furthermore, 2mDBTPDBq-II, PCBA1BP, and [Ir(dppm)$_2$(acac)] were co-evaporated to form a light-emitting layer 1113 over the hole-transport layer 1112. Here, the weight ratio of 2mDBTPDBq-II to PCBA1BP and [Ir(dppm)$_2$(acac)] was adjusted to 0.8:0.2:0.1 (=2mDBTPDBq-II: PCBA1BP:[Ir(dppm)$_2$(acac)]). The thickness of the light-emitting layer 1113 was set to 40 nm.

Further, over the light-emitting layer 1113, a film of 2mDBTPDBq-II was formed to a thickness of 15 nm to form a first electron-transport layer 1114a.

Next, over the first electron-transport layer 1114a, a film of BPhen was formed to a thickness of 15 nm to form a second electron-transport layer 1114b.

Further, over the second electron-transport layer 1114b, a film of LiF was formed by evaporation to a thickness of 1 nm to form an electron-injection layer 1115.

Lastly, an aluminum film was formed by evaporation to a thickness of 200 nm as a second electrode 1103 functioning as a cathode. Thus, the light-emitting element 4 of this example was fabricated.

Note that, in all the above evaporation steps, evaporation was performed by a resistance-heating method.

Table 5 shows an element structure of the light-emitting element 4 obtained as described above.

In a glove box containing a nitrogen atmosphere, the light-emitting element 4 was sealed so as not to be exposed to air. Then, operation characteristics of the light-emitting element were measured. Note that the measurements were carried out at room temperature (in the atmosphere kept at 25° C.).

Figure 19:
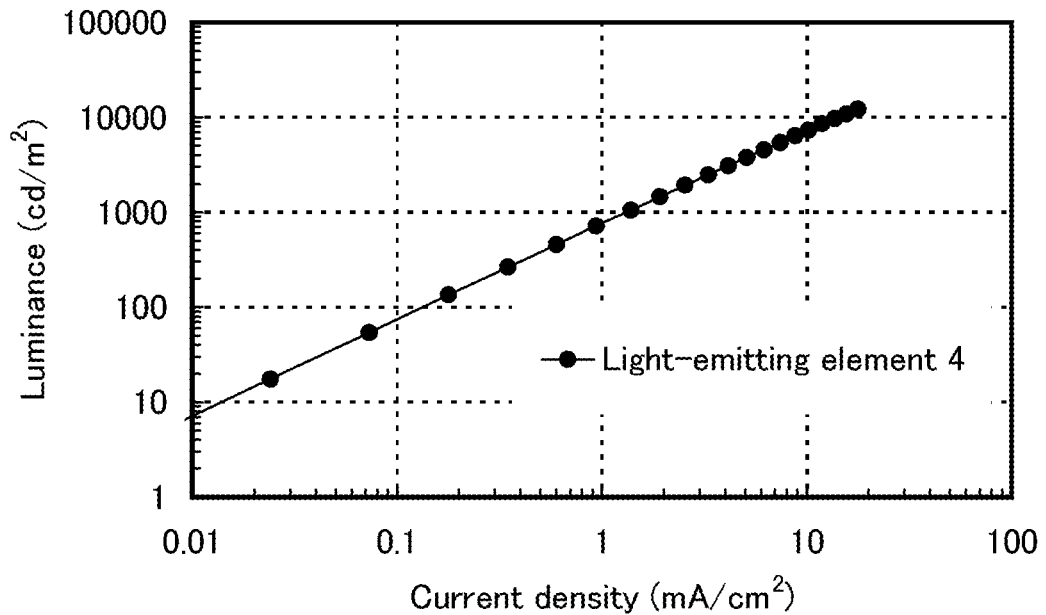
FIG. 19 shows current density-luminance characteristics of a light-emitting element of Example 6.
Figure 20:
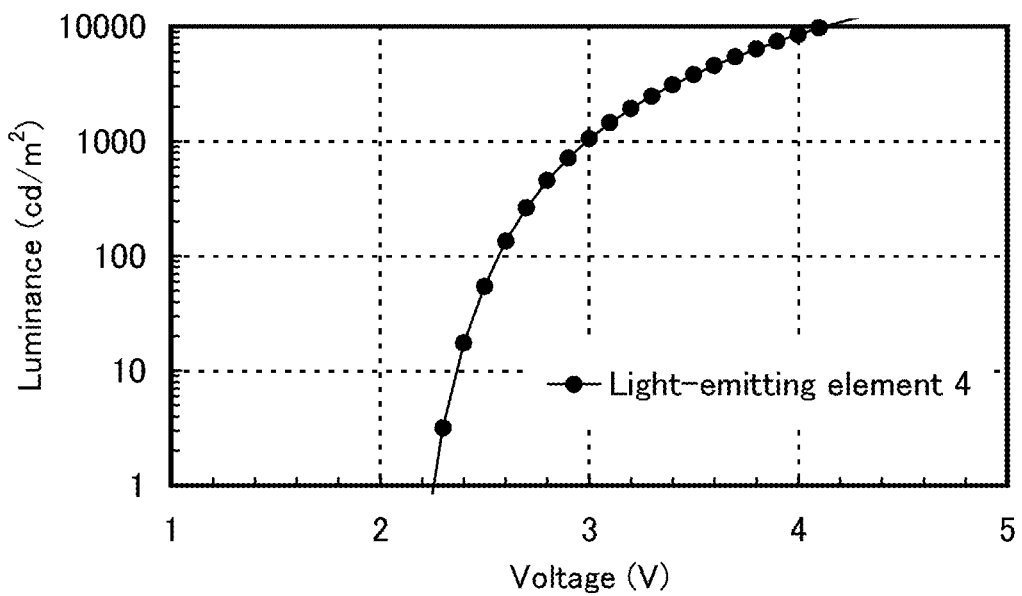
FIG. 20 shows voltage-luminance characteristics of the light-emitting element of Example 6.
Figure 21:
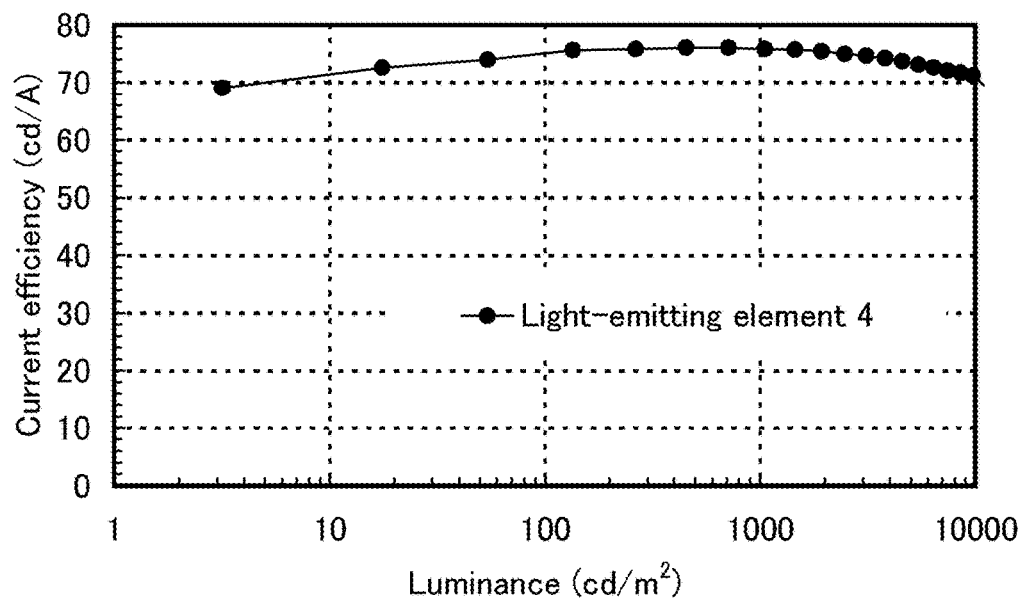
FIG. 21 shows luminance-current efficiency characteristics of the light-emitting element of Example 6.
Figure 22:
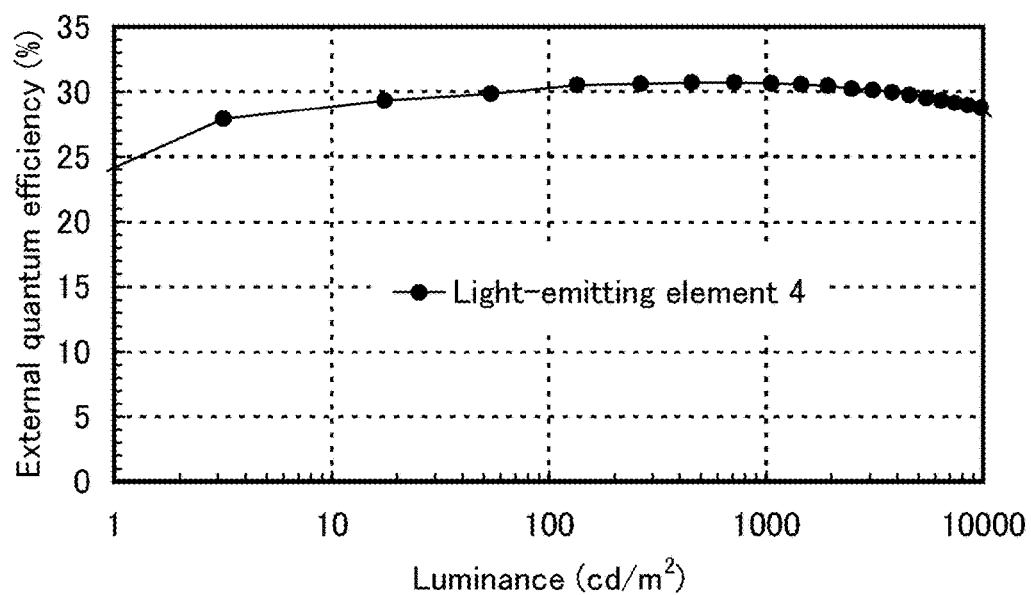
FIG. 22 shows luminance-external quantum efficiency characteristics of the light-emitting element of Example 6.

FIG. 19 shows current density-luminance characteristics of the light-emitting element 4. In FIG. 19, the horizontal axis represents current density (mA/cm$^2$), and the vertical axis represents luminance (cd/m$^2$). FIG. 20 shows voltage-luminance characteristics thereof. In FIG. 20, the horizontal axis represents voltage (V), and the vertical axis represents luminance (cd/m$^2$). FIG. 21 shows luminance-current efficiency characteristics thereof. In FIG. 21, the horizontal axis represents luminance (cd/m$^2$), and the vertical axis represents current efficiency (cd/A). FIG. 22 shows luminance-external quantum efficiency characteristics thereof. In FIG. 22, the horizontal axis represents luminance (cd/m$^2$), and the vertical axis represents external quantum efficiency (%).

Further, Table 6 shows the voltage (V), current density (mA/cm$^2$), CIE chromaticity coordinates (x, y), current efficiency (cd/A), power efficiency (lm/W), and external quantum efficiency (%) of the light-emitting element 4 at a luminance of 1100 cd/m$^2$.

TABLE 6

|   | voltage (V) | current density (mA/cm$^2$) | chromaticity coordinates (x, y) | current efficiency (cd/A) | power efficiency (lm/W) | external quantum efficiency (%) |
|---|---|---|---|---|---|---|
| light-emitting element 4 | 3.0 | 1.4 | (0.57, 0.43) | 76 | 70 | 31 |

Figure 23:
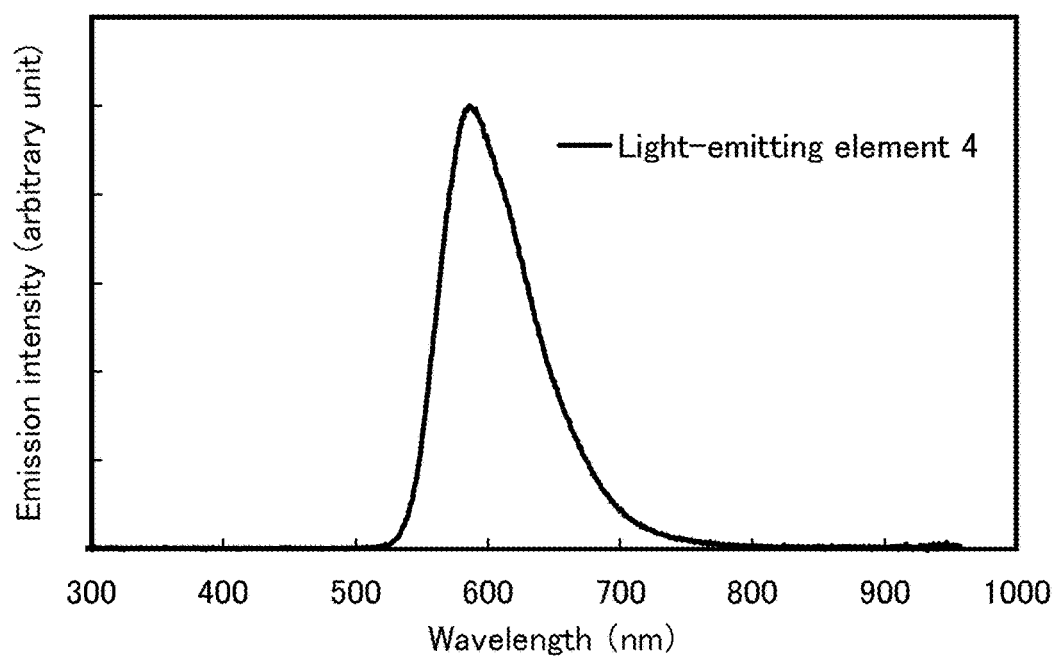
FIG. 23 shows an emission spectrum of the light-emitting element of Example 6.

FIG. 23 shows an emission spectrum of the light-emitting element 4 which was obtained by applying a current of 0.1 mA. In FIG. 23, the horizontal axis represents wavelength (nm), and the vertical axis represents emission intensity (arbitrary unit). As shown in Table 6, the CIE chromaticity coordinates of the light-emitting element 4 at a luminance of 1100 cd/m$^2$ were (x, y)=(0.57, 0.43). These results show that orange light emission originating from [Ir(dppm)$_2$(acac)] was obtained from the light-emitting element 4.

As can be seen from Table 6 and FIGS. 19 to 22, the light-emitting element 4 has high current efficiency, high power efficiency, and high external quantum efficiency. In particular, the light-emitting element 4 has an extremely high external quantum efficiency of 31% at a luminance of 1100 cd/m$^2$. As described above, the upper limit of external quantum efficiency is said to be around 25%. However, the result of the external quantum efficiency this time is above the limit.

In the light-emitting element of this example, 2mDBTPDBq-II, PCBA1BP, and [Ir(dppm)$_2$(acac)] described in

TABLE 5

|   | first elecrtrode | hole-injection layer | hole-transport layer | light-emitting layer | first electron-transport layer | second electron-transport layer | electron-injection layer | second electrode |
|---|---|---|---|---|---|---|---|---|
| light-emitting element 4 | ITSO 110 nm | BPAFLP:MoOx (=4:2) 40 nm | BPAFLP 20 nm | 2mDBTPDBq-II:PCBA1BP:[Ir(dppm)$_2$(acac)] (=0.8:0.2:0.1) 40 nm | 2mDBTPDBq-II 15 nm | BPhen 15 nm | LiF 1 nm | Al 200 nm |

Example 5 are used for the light-emitting layer. As described in Example 5, the emission spectrum of the mixed material of 2mDBTPDBq-II and PCBA1BP (the emission spectrum of an exciplex) has a larger overlap with the absorption spectrum of [Ir(dppm)$_2$(acac)] as compared with the emission spectrum of 2mDBTPDBq-II or PCBA1BP alone. The light-emitting element of this example is considered to have high energy transfer efficiency because it transfers energy by utilizing the overlap, and therefore have unprecedentedly high external quantum efficiency.

The results of Example 5 show that a peak of the absorption band on the longest wavelength side in the absorption spectrum of the guest material used in the light-emitting element 4 is close to a peak of the emission spectrum, and that the molar absorption coefficient at the peak is high (>5000 $M^{-1} \cdot cm^{-1}$). From these results, the light-emitting element 4 is considered to have particularly high energy transfer efficiency and therefore have unprecedentedly high external quantum efficiency.

The above results show that an element having high external quantum efficiency can be obtained by application of one embodiment of the present invention.

Figure 24:
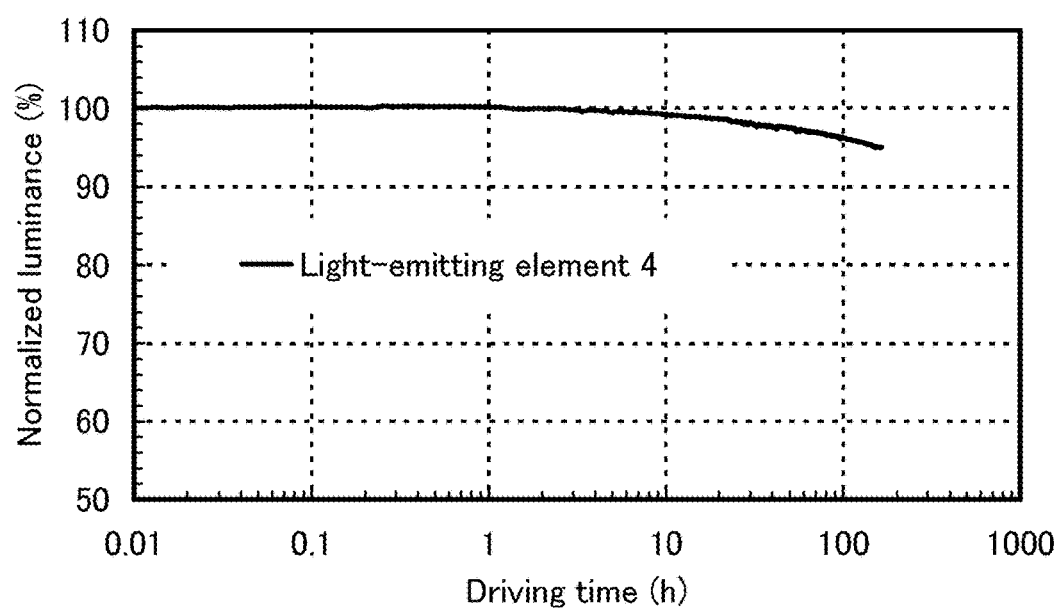
FIG. 24 shows results of reliability tests of the light-emitting element of Example 6.

Next, the light-emitting element 4 was subjected to reliability tests. Results of the reliability tests are shown in FIG. 24. In FIG. 24, the vertical axis represents normalized luminance (%) with an initial luminance of 100%, and the horizontal axis represents driving time (h) of the elements.

In the reliability tests, the light-emitting element 4 was driven under the conditions where the initial luminance was set to 5000 $cd/m^2$ and the current density was constant.

The light-emitting element 4 kept 95% of the initial luminance after the driving for 170 hours.

The above results show that an element having high reliability can be obtained by application of one embodiment of the present invention.

EXAMPLE 7

In this example, an example of a combination of a first organic compound, a second organic compound, and a phosphorescent compound which can be used for a light-emitting element of one embodiment of the present invention will be described with reference to FIGS. 26A and 26B.

The phosphorescent compound used in this example is [Ir(dppm)$_2$(acac)]. The first organic compound used in this example is 2mDBTPDBq-II. The second organic compound used in this example is 4,4'-bis[N-(1-naphthyl)-N-phenylamino]biphenyl (abbreviation: NPB). A chemical formula of the material used in this example is shown below. Note that the chemical formulae of the materials used in the above examples are omitted here.

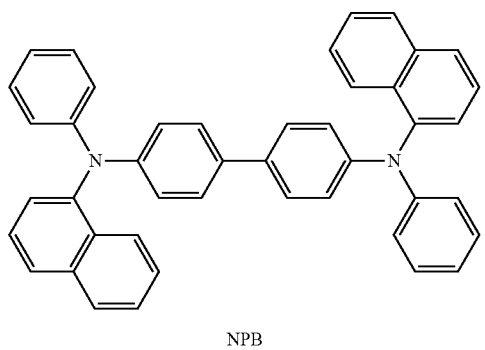 [SMILES: c1ccc(N(c2ccc(-c3ccc(N(c4ccccc4)c4cccc5ccccc45)cc3)cc2)c2cccc3ccccc23)cc1 ; "NPB"]

NPB

<Absorption Spectrum>

Figure 26A:
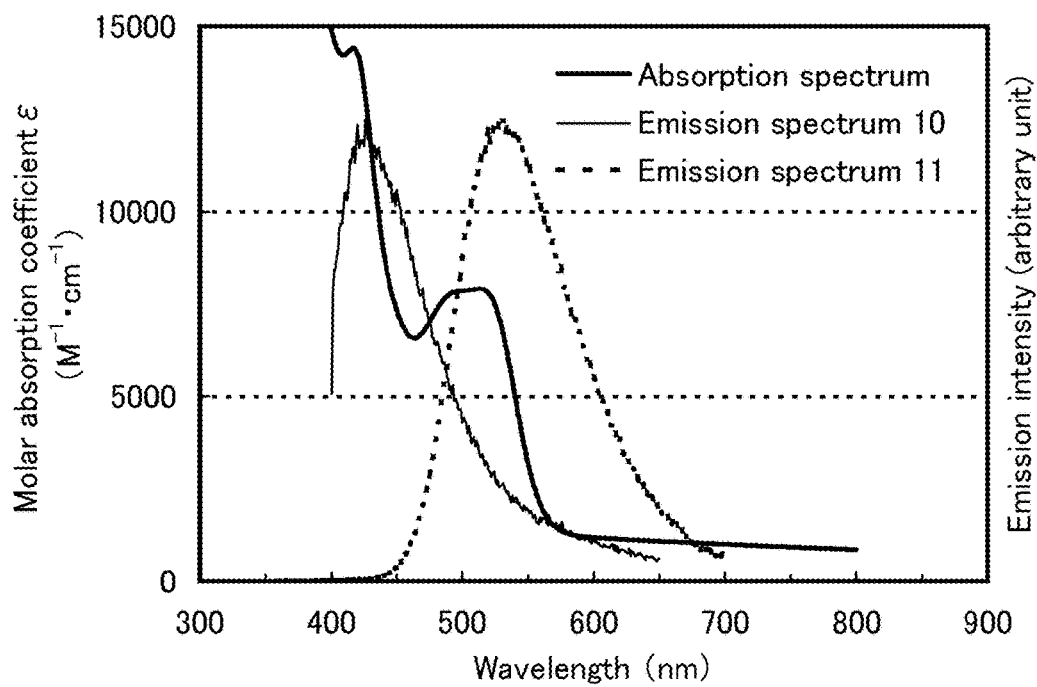
FIGS. 26A and 26B each show an absorption spectrum and emission spectra according to Example 7.
Figure 26B:
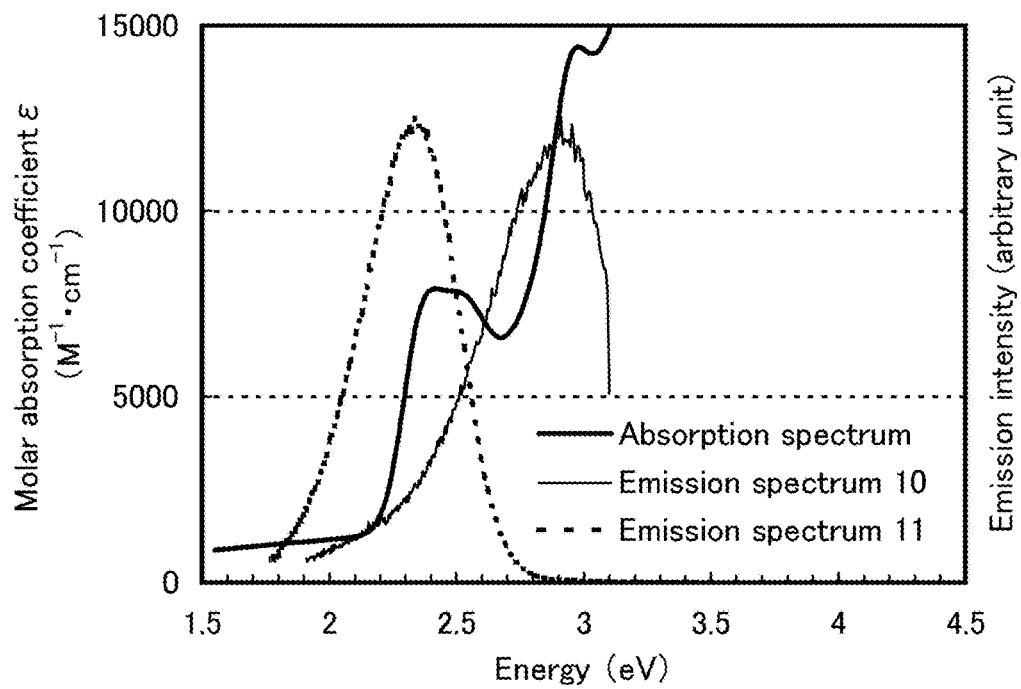

FIGS. 26A and 26B each show an ultraviolet-visible absorption spectrum (hereinafter, simply referred to as absorption spectrum) of [Ir(dppm)$_2$(acac)] that is the phosphorescent compound in a dichloromethane solution of [Ir(dppm)$_2$(acac)]. The absorption spectrum was measured with the use of an ultraviolet-visible light spectrophotometer (V-550, manufactured by JASCO Corporation) in the state where the dichloromethane solution (0.093 mmol/L) was put in a quartz cell at room temperature.

<Emission Spectrum>

FIGS. 26A and 26B each also show an emission spectrum of a thin film of 2mDBTPDBq-II that is the first organic compound (an emission spectrum 10) and an emission spectrum of a thin film of a mixed material of 2mDBTPDBq-II and NPB (an emission spectrum 11). In FIG. 26A, the horizontal axis represents wavelength (nm), and the vertical axes represent molar absorption coefficient ε ($M^{-1} \cdot cm^{-1}$) and emission intensity (arbitrary unit). In FIG. 26B, the horizontal axis represents energy (eV), and the vertical axes represent molar absorption coefficient ε ($M^{-1} \cdot cm^{-1}$) and emission intensity (arbitrary unit).

As can be seen from the absorption spectrum in FIG. 26A, [Ir(dppm)$_2$(acac)] has a broad absorption band at around 520 nm. This absorption band is considered to greatly contribute to light emission.

The emission spectrum 11 peaks at a longer wavelength (lower energy) than the emission spectrum 10. In addition, the peak of the emission spectrum 11 is closer to the absorption band than the peak of the emission spectrum 10. It is known that the emission spectrum of NPB that is the second organic compound peaks at around 430 nm. This means that the emission spectrum 11 peaks at a longer wavelength (lower energy) than the emission spectrum of NPB. It also means that the peak of the emission spectrum 11 is closer to the absorption band than the peak of the emission spectrum of NPB. The above findings show that the emission spectrum 11 has the largest overlap with the absorption band in the absorption spectrum which greatly contributes to light emission. Specifically, the difference between the peak (515 nm) of the absorption band in the absorption spectrum and the peak of the emission spectrum 11 is 0.09 eV.

It is found that the emission spectrum of the mixed material of 2mDBTPDBq-II and NPB peaks at a longer wavelength (lower energy) than the emission spectrum of either organic compound alone. This indicates that an exciplex is formed by mixing 2mDBTPDBq-II with NPB.

It is found that the peak of the emission spectrum of the mixed material has a large overlap with the absorption band in the absorption spectrum of [Ir(dppm)$_2$(acac)] which is considered to greatly contribute to light emission. Thus, it is indicated that the light-emitting element including [Ir(dppm)$_2$(acac)] and the mixed material of 2mDBTPDBq-II and NPB has high energy transfer efficiency because it transfers energy by utilizing the overlap between the emission spectrum of the mixed material and the absorption spectrum of the phosphorescent compound. Accordingly, it is indicated that a light-emitting element having high external quantum efficiency can be obtained.

EXAMPLE 8

In this example, a light-emitting element of one embodiment of the present invention will be described with reference to FIG. 15. A chemical formula of a material used in this example is shown below. Note that structural formulae of the materials used in the above examples are omitted here.

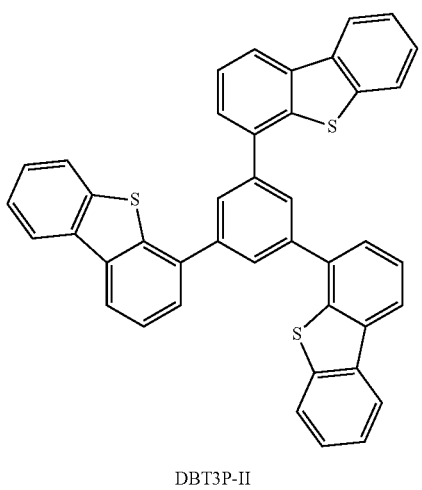 [SMILES: c1ccc2c(c1)sc1c(-c3cc(-c4cccc5c4sc4ccccc45)cc(-c4cccc5c4sc4ccccc45)c3)cccc12 ; "DBT3P-II"]

DBT3P-II

Methods for manufacturing a light-emitting element 5 of this example and a comparative light-emitting element 6 will be described below.

(Light-emitting Element 5)

First, a film of ITSO was formed over a glass substrate 1100 by a sputtering method, so that a first electrode 1101 functioning as an anode was formed. Note that the thickness was set to 110 nm and the electrode area was set to 2 mm×2 mm.

Next, as pretreatment for forming the light-emitting element over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, 4,4',4"-(1,3,5-benzenetriyl)tri(dibenzothiophene) (abbreviation: DBT3P-II) and molybdenum(VI) oxide were co-evaporated to form a hole-injection layer 1111 over the first electrode 1101. The thickness of the hole-injection layer 1111 was set to 40 nm, and the weight ratio of DBT3P-II to molybdenum oxide was adjusted to 4:2 (=DBT3P-II:molybdenum oxide).

Next, over the hole-injection layer 1111, a film of BPA-FLP was formed to a thickness of 20 nm to form a hole-transport layer 1112.

Furthermore, 2mDBTPDBq-II, NPB, and [Ir(dppm)$_2$(acac)] were co-evaporated to form a light-emitting layer 1113 over the hole-transport layer 1112. Here, the weight ratio of 2mDBTPDBq-II to NPB and [Ir(dppm)$_2$(acac)] was adjusted to 0.8:0.2:0.05 (=2mDBTPDBq-II:NPB:[Ir(dppm)$_2$(acac)]). The thickness of the light-emitting layer 1113 was set to 40 nm.

Further, over the light-emitting layer 1113, a film of 2mDBTPDBq-II was formed to a thickness of 10 nm to form a first electron-transport layer 1114a.

Next, over the first electron-transport layer 1114a, a film of BPhen was formed to a thickness of 20 nm to form a second electron-transport layer 1114b.

Further, over the second electron-transport layer 1114b, a film of LiF was formed by evaporation to a thickness of 1 nm to form an electron-injection layer 1115.

Lastly, an aluminum film was formed by evaporation to a thickness of 200 nm as a second electrode 1103 functioning as a cathode. Thus, the light-emitting element 5 of this example was fabricated.

(Comparative Light-emitting Element 6)

A light-emitting layer 1113 of the comparative light-emitting element 6 was formed by co-evaporating 2mDBTPDBq-II and [Ir(dppm)$_2$(acac)]. Here, the weight ratio of 2mDBTPDBq-II to [Ir(dppm)$_2$(acac)] was adjusted to 1:0.05 (=2mDBTPDBq-II:[Ir(dppm)$_2$(acac)]). The thickness of the light-emitting layer 1113 was set to 40 nm. Components other than the light-emitting layer 1113 were manufactured in a manner similar to that of the light-emitting element 5.

Note that, in all the above evaporation steps, evaporation was performed by a resistance-heating method.

Table 7 shows element structures of the light-emitting element 5 and the comparative light-emitting element 6 obtained as described above.

TABLE 7

| | first elecrtrode | hole-injection layer | hole-transport layer | light-emitting layer | first electron-transport layer | second electron-transport layer | electron-injection layer | second electrode |
|---|---|---|---|---|---|---|---|---|
| light-emitting element 5 | ITSO 110 nm | DBT3P-II:MoOx (=4:2) 40 nm | BPAFLP 20 nm | 2mDBTPDBq-II:NPB:[Ir(dppm)$_2$(acac)] (=0.8:0.2:0.05) 40 nm | 2mDBTPDBq-II 10 nm | BPhen 20 nm | LiF 1 nm | Al 200 nm |
| comparative light-emitting element 6 | ITSO 110 nm | DBT3P-II:MoOx (=4:2) 40 nm | BPAFLP 20 nm | 2mDBTPDBq-II:[Ir(dppm)$_2$(acac)] (=1:0.05) 40 nm | 2mDBTPDBq-II 10 nm | BPhen 20 nm | LiF 1 nm | Al 200 nm |

In a glove box containing a nitrogen atmosphere, these light-emitting elements were sealed so as not to be exposed to air. Then, operation characteristics of these light-emitting elements were measured. Note that the measurements were carried out at room temperature (in the atmosphere kept at 25° C.).

Figure 27:
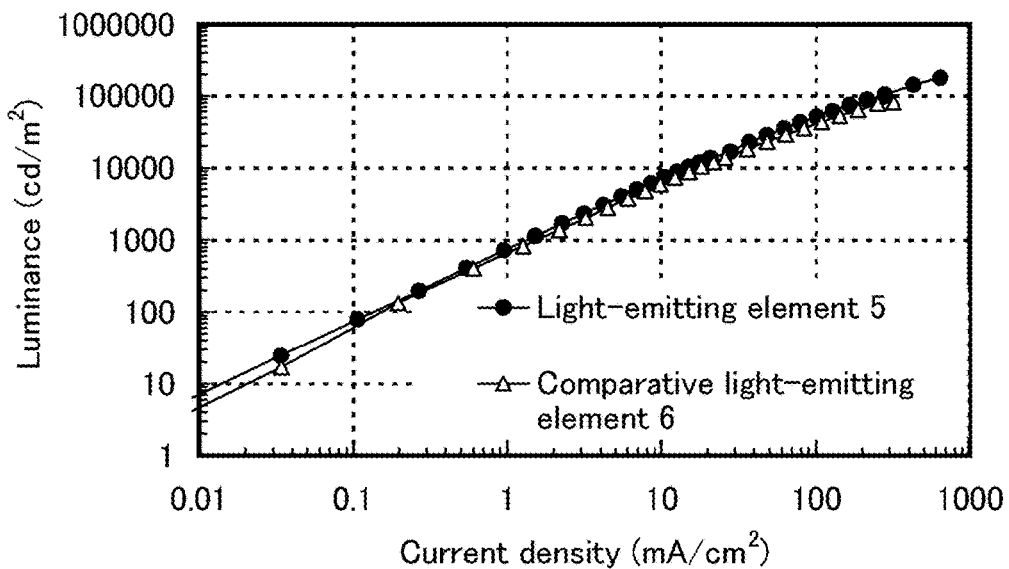
FIG. 27 shows current density-luminance characteristics of a light emitting element of Example 8.
Figure 28:
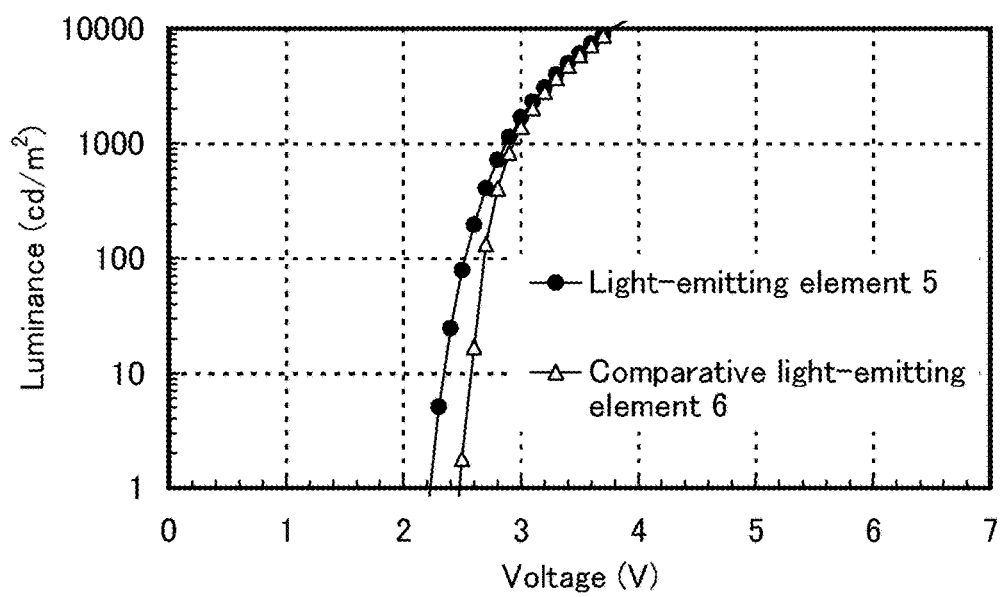
FIG. 28 shows voltage-luminance characteristics of the light-emitting element of Example 8.
Figure 29:
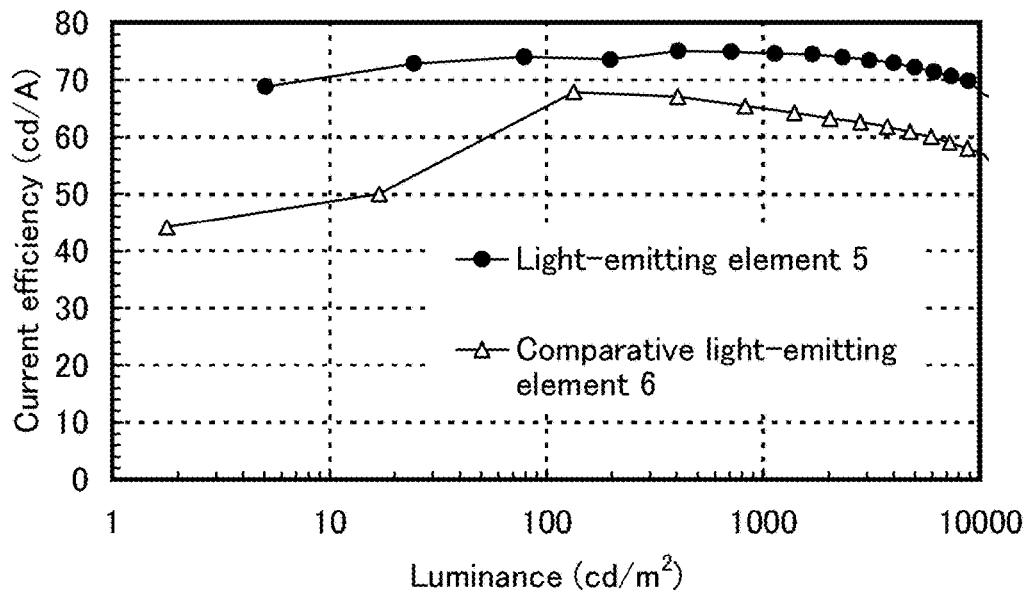
FIG. 29 shows luminance-current efficiency characteristics of the light-emitting element of Example 8.
Figure 30:
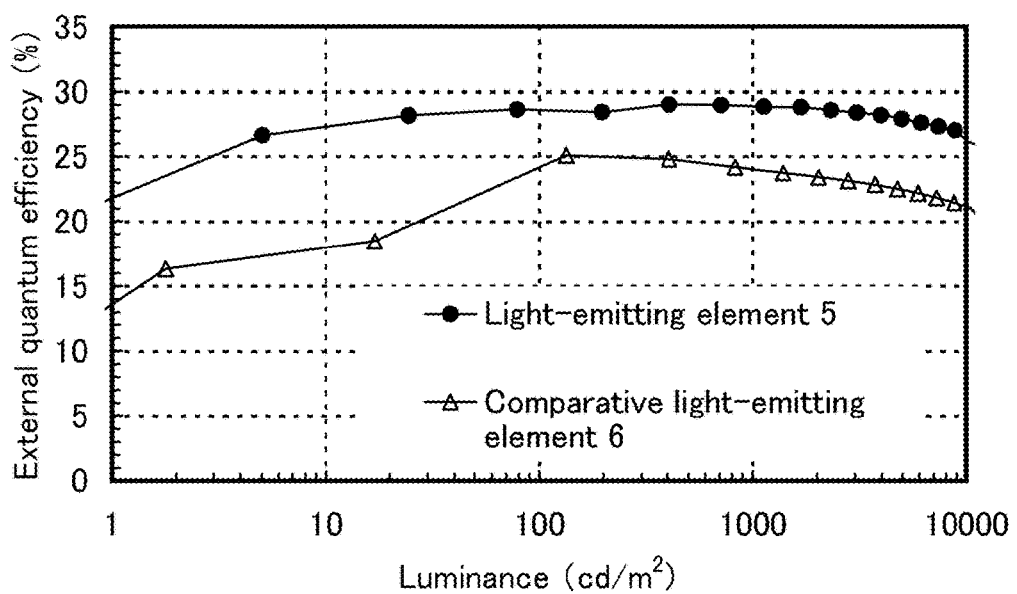
FIG. 30 shows luminance-external quantum efficiency characteristics of the light-emitting element of Example 8.

FIG. 27 shows current density-luminance characteristics of the light-emitting element 5 and the comparative light-emitting element 6. In FIG. 27, the horizontal axis represents current density (mA/cm$^2$), and the vertical axis represents luminance (cd/m$^2$). FIG. 28 shows voltage-luminance characteristics thereof. In FIG. 28, the horizontal axis represents voltage (V), and the vertical axis represents luminance (cd/m$^2$). FIG. 29 shows luminance-current efficiency characteristics thereof. In FIG. 29, the horizontal axis represents luminance (cd/m$^2$), and the vertical axis represents current efficiency (cd/A). FIG. 30 shows luminance-external quantum efficiency characteristics thereof. In FIG. 30, the horizontal axis represents luminance (cd/m$^2$), and the vertical axis represents external quantum efficiency (%).

Further, Table 8 shows the voltage (V), current density (mA/cm$^2$), CIE chromaticity coordinates (x, y), current efficiency (cd/A), power efficiency (lm/W), and external quantum efficiency (%) of each of the light-emitting element 5 and the comparative light-emitting element 6 at a luminance of around 1000 cd/m$^2$.

TABLE 8

| | voltage (V) | current density (mA/cm$^2$) | chromaticity coordinates (x, y) | luminance (cd/m$^2$) | current efficiency (cd/A) | power efficiency (lm/W) | external quantum efficiency (%) |
|---|---|---|---|---|---|---|---|
| light-emitting element 5 | 2.9 | 1.5 | (0.57, 0.43) | 1100 | 75 | 81 | 29 |
| comparative light-emitting element 6 | 2.9 | 1.3 | (0.56, 0.44) | 830 | 65 | 71 | 24 |

Figure 31:
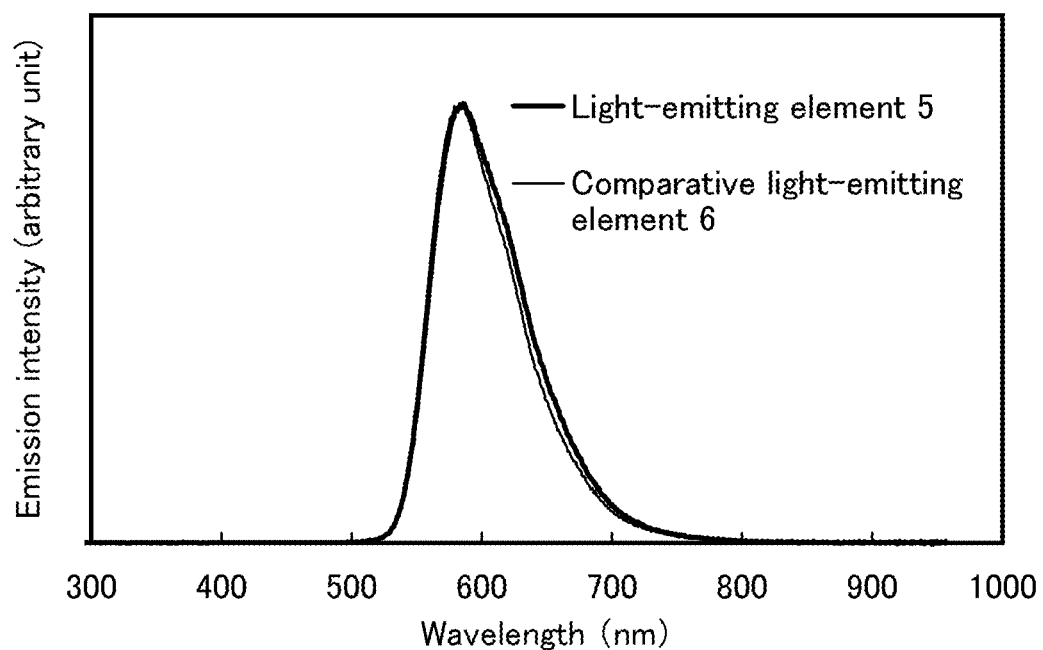
FIG. 31 shows an emission spectrum of the light-emitting element of Example 8.

FIG. 31 shows emission spectra of the light-emitting element 5 and the comparative light-emitting element 6 which were obtained by applying a current of 0.1 mA. In FIG. 31, the horizontal axis represents wavelength (nm), and the vertical axis represents emission intensity (arbitrary unit). As shown in Table 8, the CIE chromaticity coordinates of the light-emitting element 5 at a luminance of 1100 cd/m$^2$ were (x, y)=(0.57, 0.43), and the CIE chromaticity coordinates of the comparative light-emitting element 6 at a luminance of 830 cd/m$^2$ were (x, y)=(0.56, 0.44). These results show that orange light emission originating from [Ir(dppm)$_2$(acac)] was obtained from the light-emitting element 5 and the comparative light-emitting element 6.

As can be seen from Table 8 and FIGS. 27 to 30, the light-emitting element 5 has higher current efficiency, higher power efficiency, and higher external quantum efficiency than the comparative light-emitting element 6.

In the light-emitting element 5, 2mDBTPDBq-II, NPB, and [Ir(dppm)$_2$(acac)] described in Example 7 are used for the light-emitting layer. As described in Example 7, the emission spectrum of the mixed material of 2mDBTPDBq-II and NPB (the emission spectrum of an exciplex) has a larger overlap with the absorption band in the absorption spectrum of [Ir(dppm)$_2$(acac)] which is considered to greatly contribute to light emission, as compared with the emission spectrum of 2mDBTPDBq-II alone. The light-emitting element 5 is considered to have high energy transfer efficiency because it transfers energy by utilizing the overlap, and therefore have higher external quantum efficiency than the comparative light-emitting element 6.

The results of Example 7 show that a peak of the absorption band on the longest wavelength side in the absorption spectrum of the phosphorescent compound used in the light-emitting element 5 is close to a peak of the emission spectrum, and that the molar absorption coefficient at the peak is high (>5000 M$^{-1}$·cm$^{-1}$). From these results, the light-emitting element 5 is considered to have particularly high energy transfer efficiency and therefore have unprecedentedly high external quantum efficiency.

The above results show that an element having high external quantum efficiency can be obtained by application of one embodiment of the present invention.

EXAMPLE 9

In this example, an example of a combination of a first organic compound, a second organic compound, and a phosphorescent compound which can be used for a light-emitting element of one embodiment of the present invention will be described with reference to FIGS. 32A and 32B.

The phosphorescent compound used in this example is bis(2,3,5-triphenylpyrazinato)(dipivaloylmethanato)iridium (III) (abbreviation: [Ir(tppr)$_2$(dpm)]). The first organic compound used in this example is 2mDBTPDBq-II. The second organic compound used in this example is NPB. A chemical formula of the material used in this example is shown below. Note that the chemical formulae of the materials used in the above examples are omitted here.

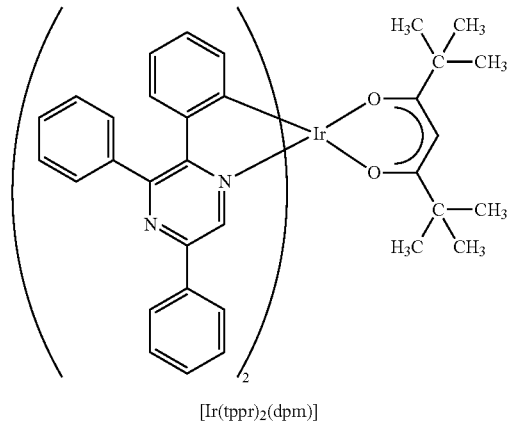

[Ir(tppr)$_2$(dpm)]

<Absorption Spectrum>

Figure 32A:
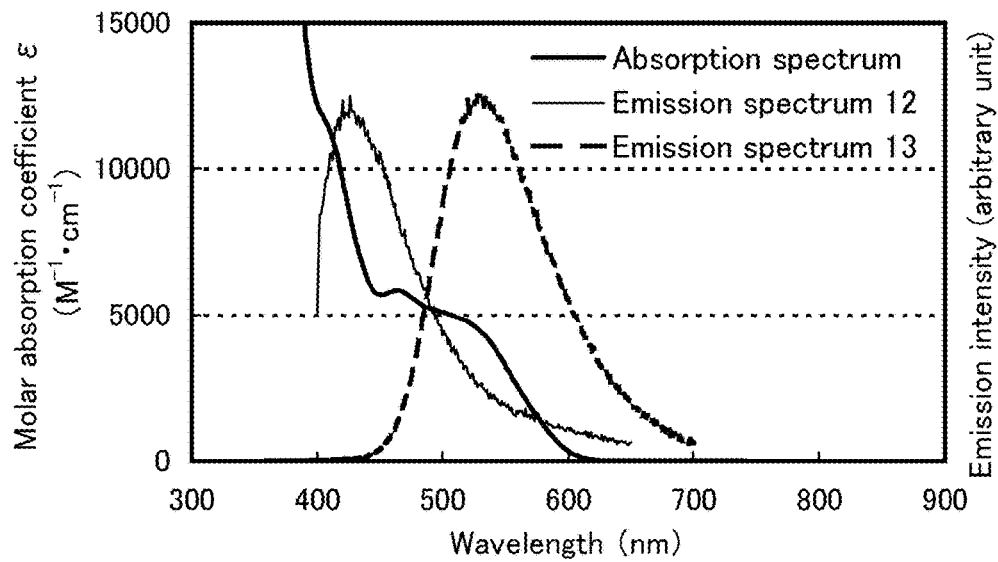
FIGS. 32A and 32B each show an absorption spectrum and emission spectra according to Example 9.
Figure 32B:
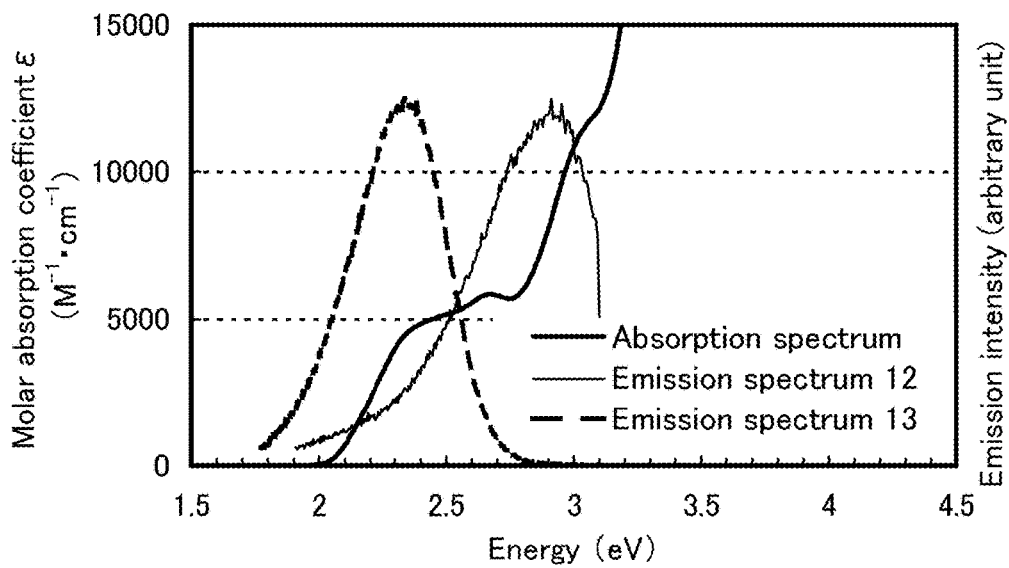

FIGS. 32A and 32B each show an ultraviolet-visible absorption spectrum (hereinafter, simply referred to as absorption spectrum) of [Ir(tppr)$_2$(dpm)] that is the phosphorescent compound in a dichloromethane solution of [Ir(tppr)$_2$(dpm)]. The absorption spectrum was measured with the use of an ultraviolet-visible light spectrophotometer (V-550, manufactured by JASCO Corporation) in the state where the dichloromethane solution (0.094 mmol/L) was put in a quartz cell at room temperature.

<Emission Spectrum>

FIGS. 32A and 32B each also show an emission spectrum of a thin film of 2mDBTPDBq-II that is the first organic compound (an emission spectrum 12) and an emission spectrum of a thin film of a mixed material of 2mDBTPDBq-II and NPB (an emission spectrum 13). In FIG. 32A, the horizontal axis represents wavelength (nm), and the vertical axes represent molar absorption coefficient ε (M$^{-1}$·cm$^{-1}$) and emission intensity (arbitrary unit). In FIG. 32B, the horizontal axis represents energy (eV), and the vertical axes represent molar absorption coefficient ε ($M^{-1} \cdot cm^{-1}$) and emission intensity (arbitrary unit).

As can be seen from the absorption spectrum in FIG. 32A, [Ir(tppr)$_2$(dpm)] has a broad absorption band at around 530 nm. This absorption band is considered to greatly contribute to light emission.

The emission spectrum 13 peaks at a longer wavelength (lower energy) than the emission spectrum 12. In addition, the peak of the emission spectrum 13 is closer to the absorption band than the peak of the emission spectrum 12. It is known that the emission spectrum of NPB that is the second organic compound peaks at around 430 nm. This means that the emission spectrum 13 peaks at a longer wavelength (lower energy) than the emission spectrum of NPB. It also means that the peak of the emission spectrum 13 is closer to the absorption band than the peak of the emission spectrum of NPB. The above findings show that the emission spectrum 13 has the largest overlap with the absorption band in the absorption spectrum which greatly contributes to light emission. Specifically, the difference between the peak of the absorption band in the absorption spectrum (a shoulder peak at around 530 nm) and the peak of the emission spectrum 13 is 0.01 eV.

Methods for manufacturing a light-emitting element 7 of this example and a comparative light-emitting element 8 will be described below.

(Light-emitting Element 7)

A light-emitting layer 1113 of the light-emitting element 7 was formed by co-evaporating 2mDBTPDBq-II, NPB, and [Ir(tppr)$_2$(dpm)]. Here, the weight ratio of 2mDBTPDBq-II to NPB and [Ir(tppr)$_2$(dpm)] was adjusted to 0.8:0.2:0.05 (=2mDBTPDBq-II:NPB:[Ir(tppr)$_2$(dpm)]). The thickness of the light-emitting layer 1113 was set to 40 nm. Components other than the light-emitting layer 1113 were manufactured in a manner similar to that of the light-emitting element 5 described in Example 8.

(Comparative Light-emitting Element 8)

A light-emitting layer 1113 of the comparative light-emitting element 8 was formed by co-evaporating 2mDBT-PDBq-II and [Ir(tppr)$_2$(dpm)]. Here, the weight ratio of 2mDBTPDBq-II to [Ir(tppr)$_2$(dpm)] was adjusted to 1:0.05 (=2mDBTPDBq-II: [Ir(tppr)$_2$(dpm)]. The thickness of the light-emitting layer 1113 was set to 40 nm. Components other than the light-emitting layer 1113 were manufactured in a manner similar to that of the light-emitting element 5 described in Example 8.

Table 9 shows element structures of the light-emitting element 7 and the comparative light-emitting element 8 obtained as described above.

TABLE 9

| | first elecrtrode | hole-injection layer | hole-transport layer | light-emitting layer | first electron-transport layer | second electron-transport layer | electron-injection layer | second electrode |
|---|---|---|---|---|---|---|---|---|
| light-emitting element 7 | ITSO 110 nm | DBT3P-II:MoOx (=4:2) 40 nm | BPAFLP 20 nm | 2mDBTPDBq-II:NPB:[Ir(tppr)$_2$(dpm)] (=0.8:0.2:0.05) 40 nm | 2mDBTPDBq-II 10 nm | BPhen 20 nm | LiF 1 nm | Al 200 nm |
| comparative light-emitting element 8 | ITSO 110 nm | DBT3P-II:MoOx (=4:2) 40 nm | BPAFLP 20 nm | 2mDBTPDBq-II:[Ir(tppr)$_2$(dpm)] (=1:0.05) 40 nm | 2mDBTPDBq-II 10 nm | BPhen 20 nm | LiF 1 nm | Al 200 nm |

It is found that the emission spectrum of the mixed material of 2mDBTPDBq-II and NPB peaks at a longer wavelength (lower energy) than the emission spectrum of either organic compound alone. This indicates that an exciplex is formed by mixing 2mDBTPDBq-II with NPB.

It is found that the peak of the emission spectrum of the mixed material has a large overlap with the absorption band in the absorption spectrum of [Ir(tppr)$_2$(dpm)] which is considered to greatly contribute to light emission. Thus, it is indicated that the light-emitting element including [Ir(tppr)$_2$(dpm)] and the mixed material of 2mDBTPDBq-II and NPB has high energy transfer efficiency because it transfers energy by utilizing the overlap between the emission spectrum of the mixed material and the absorption spectrum of the phosphorescent compound. Accordingly, it is indicated that a light-emitting element having high external quantum efficiency can be obtained.

EXAMPLE 10

In this example, a light-emitting element of one embodiment of the present invention will be described with reference to FIG. 15. The materials used in this example are used in the above examples, and therefore the chemical formulae thereof are omitted here.

In a glove box containing a nitrogen atmosphere, these light-emitting elements were sealed so as not to be exposed to air. Then, operation characteristics of these light-emitting elements were measured. Note that the measurements were carried out at room temperature (in the atmosphere kept at 25° C.).

Figure 33:
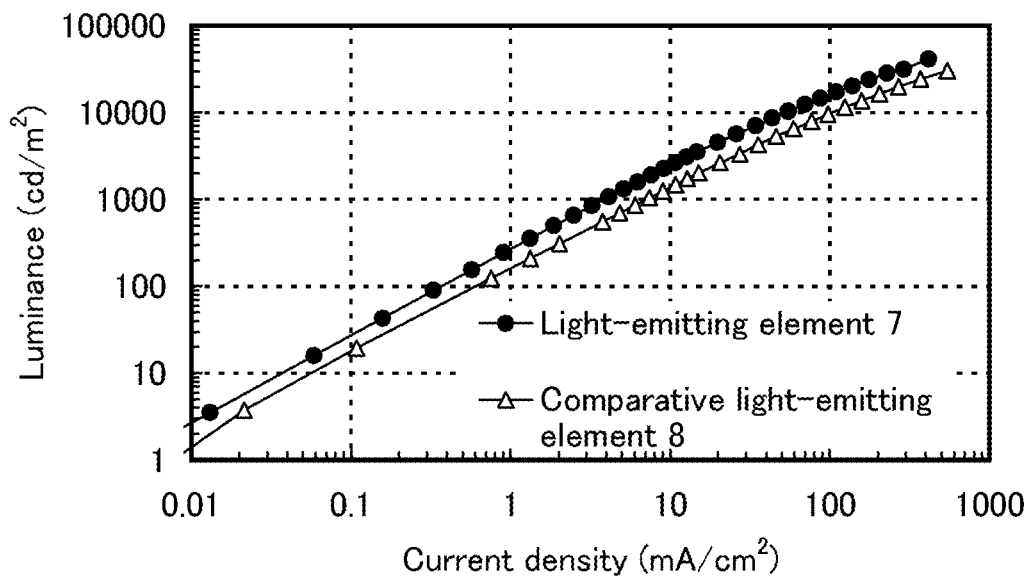
FIG. 33 shows current density-luminance characteristics of a light-emitting element of Example 10.
Figure 34:
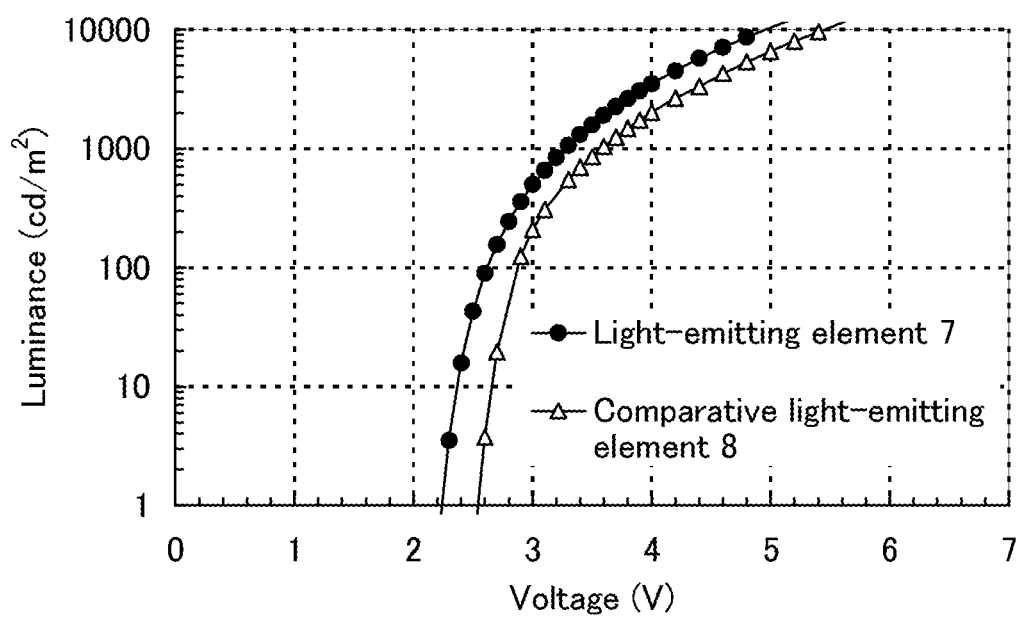
FIG. 34 shows voltage-luminance characteristics of the light-emitting element of Example 10.
Figure 35:
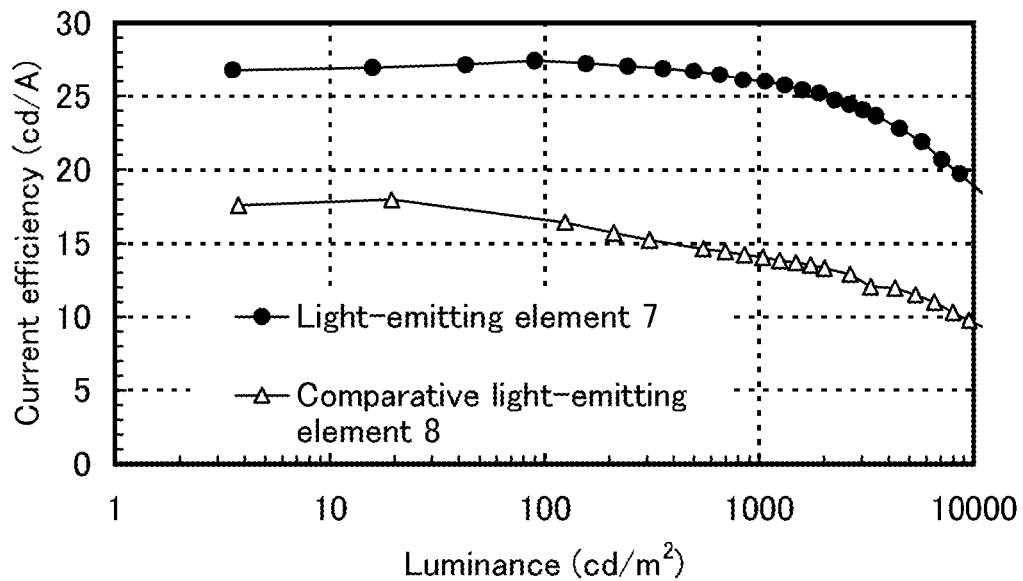
FIG. 35 shows luminance-current efficiency characteristics of the light-emitting element of Example 10.
Figure 36:
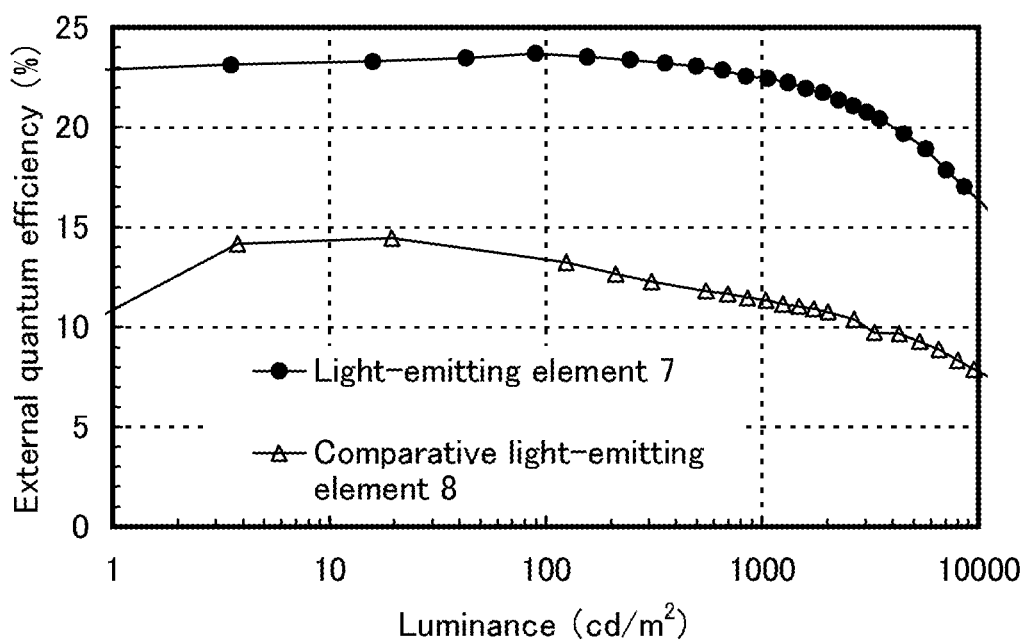
FIG. 36 shows luminance-external quantum efficiency characteristics of the light-emitting element of Example 10.

FIG. 33 shows current density-luminance characteristics of the light-emitting element 7 and the comparative light-emitting element 8. In FIG. 33, the horizontal axis represents current density (mA/cm$^2$), and the vertical axis represents luminance (cd/m$^2$). FIG. 34 shows voltage-luminance characteristics thereof. In FIG. 34, the horizontal axis represents voltage (V), and the vertical axis represents luminance (cd/m$^2$). FIG. 35 shows luminance-current efficiency characteristics thereof. In FIG. 35, the horizontal axis represents luminance (cd/m$^2$), and the vertical axis represents current efficiency (cd/A). FIG. 36 shows luminance-external quantum efficiency characteristics thereof. In FIG. 36, the horizontal axis represents luminance (cd/m$^2$), and the vertical axis represents external quantum efficiency (%).

Further, Table 10 shows the voltage (V), current density (mA/cm$^2$), CIE chromaticity coordinates (x, y), current efficiency (cd/A), power efficiency (lm/W), and external quantum efficiency (%) of each of the light-emitting element 7 and the comparative light-emitting element 8 at a luminance of around 1000 cd/m$^2$.

TABLE 10

|  | voltage (V) | current density (mA/cm$^2$) | chromaticity coordinates (x, y) | luminance (cd/m$^2$) | current efficiency (cd/A) | power efficiency (lm/W) | external quantum efficiency (%) |
|---|---|---|---|---|---|---|---|
| light-emitting element 7 | 3.3 | 4.1 | (0.66, 0.34) | 1100 | 26 | 25 | 22 |
| comparative light-emitting element 8 | 3.6 | 7.4 | (0.66, 0.34) | 1000 | 14 | 12 | 11 |

Figure 37:
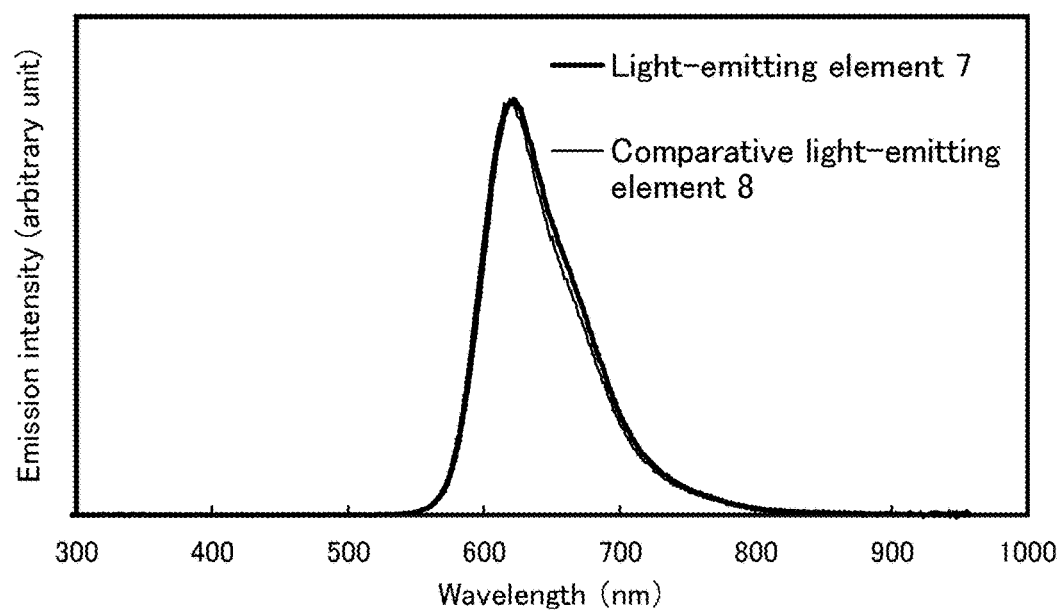
FIG. 37 shows an emission spectrum of the light-emitting element of Example 10.

FIG. 37 shows emission spectra of the light-emitting element 7 and the comparative light-emitting element 8 which were obtained by applying a current of 0.1 mA. In FIG. 37, the horizontal axis represents wavelength (nm), and the vertical axis represents emission intensity (arbitrary unit). As shown in Table 10, the CIE chromaticity coordinates of the light-emitting element 7 at a luminance of 1100 cd/m$^2$ were (x, y)=(0.66, 0.34), and the CIE chromaticity coordinates of the comparative light-emitting element 8 at a luminance of 1000 cd/m$^2$ were (x, y)=(0.66, 0.34). These results show that red light emission originating from [Ir(tppr)$_2$(dpm)] was obtained from the light-emitting element 7 and the comparative light-emitting element 8.

As can be seen from Table 10 and FIGS. 33 to 36, the light-emitting element 7 has higher current efficiency, higher power efficiency, and higher external quantum efficiency than the comparative light-emitting element 8.

In the light-emitting element 7, 2mDBTPDBq-II, NPB, and [Ir(tppr)$_2$(dpm)] described in Example 9 are used for the light-emitting layer. As described in Example 9, the emission spectrum of the mixed material of 2mDBTPDBq-II and NPB (the emission spectrum of an exciplex) has a larger overlap with the absorption band in the absorption spectrum of [Ir(tppr)$_2$(dpm)] which is considered to greatly contribute to light emission, as compared with the emission spectrum of 2mDBTPDBq-II alone. The light-emitting element 7 is considered to have high energy transfer efficiency because it transfers energy by utilizing the overlap, and therefore have higher external quantum efficiency than the comparative light-emitting element 8.

The above results show that an element having high external quantum efficiency can be obtained by application of one embodiment of the present invention.

Figure 38:
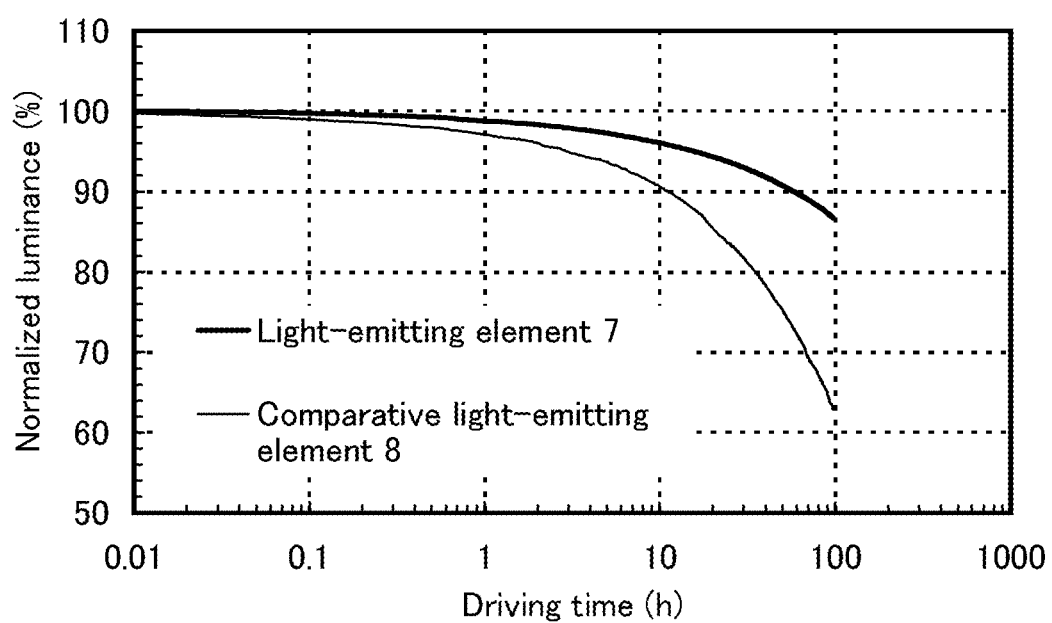
FIG. 38 shows results of reliability tests of the light-emitting element of Example 10.

Next, the light-emitting element 7 and the comparative light-emitting element 8 were subjected to reliability tests. Results of the reliability tests are shown in FIG. 38. In FIG. 38, the vertical axis represents normalized luminance (%) with an initial luminance of 100%, and the horizontal axis represents driving time (h) of the elements.

In the reliability tests, the light-emitting element 7 and the comparative light-emitting element 8 were driven under the conditions where the initial luminance was set to 5000 cd/m$^2$ and the current density was constant.

The luminance of the comparative light-emitting element 8 after 97 hours was 63% of the initial luminance. The luminance of the light-emitting element 7 after 98 hours was 87% of the initial luminance. From the results, the light-emitting element 7 is found to have a longer lifetime than the comparative light-emitting element 8.

The above results show that an element having high reliability can be obtained by application of one embodiment of the present invention.

EXAMPLE 11

In this example, examples of combinations of a first organic compound, a second organic compound, and a phosphorescent compound which can be used for a light-emitting element of one embodiment of the present invention will be described with reference to FIGS. 39A and 39B.

The phosphorescent compound used in this example is (acetylacetonato)bis(6-methyl-4-phenylpyrimidinato)iridium(III) (abbreviation: [Ir(mppm)$_2$(acac)]). The first organic compound used in this example is 2mDBTPDBq-II. Two kinds of second organic compounds, PCBA1BP and 4-(1-naphthyl)-4'-phenyltriphenylamine (abbreviation: αNBA1BP), are used in this example. Chemical formulae of the materials used in this example are shown below. Note that the chemical formulae of the materials used in the above examples are omitted here.

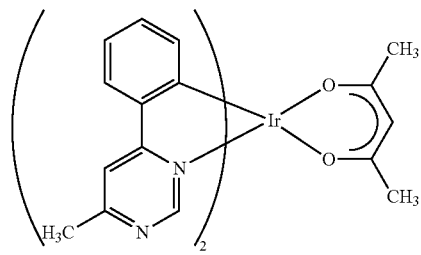

[Ir(mppm)$_2$(acac)]

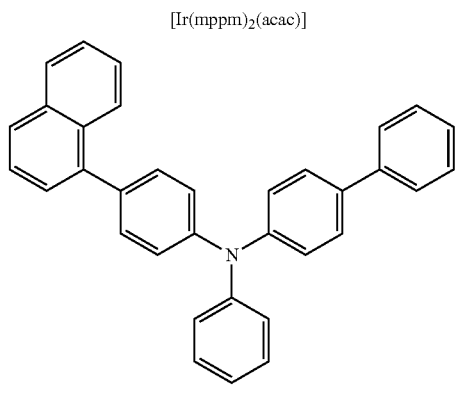

α NBA1BP

<Absorption Spectrum>

Figure 39A:
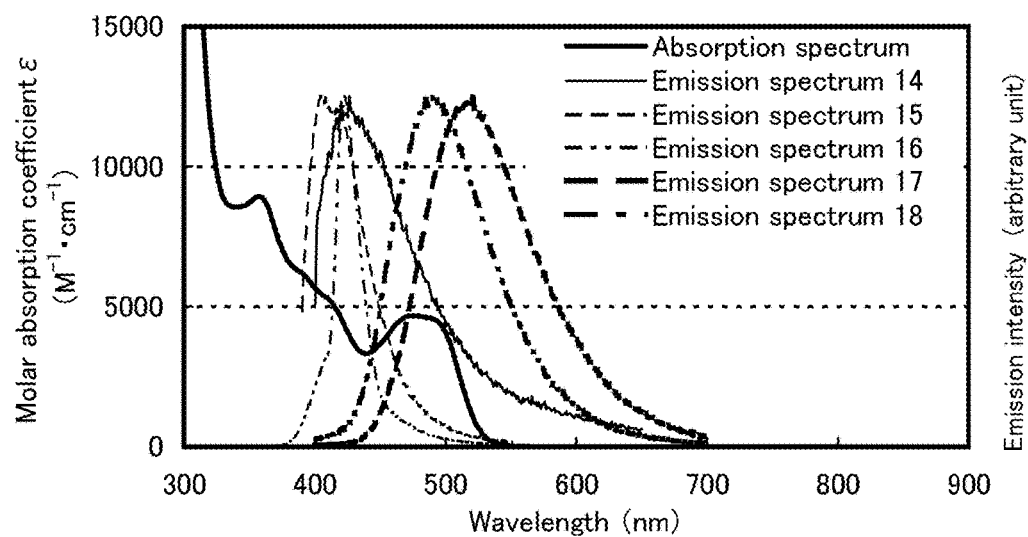
FIGS. 39A and 39B each show an absorption and emission spectra according to Example 11.
Figure 39B:
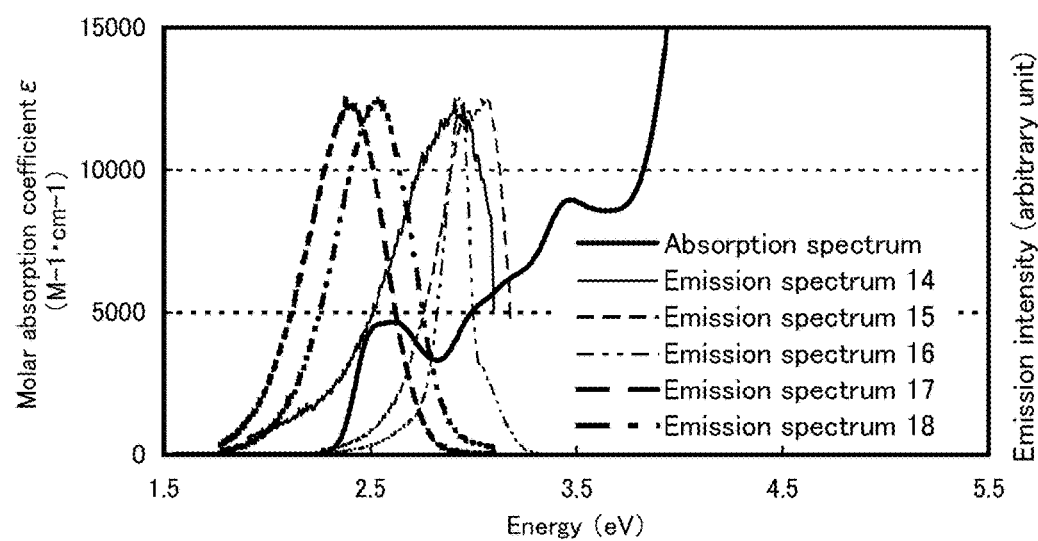

FIGS. 39A and 39B each show an ultraviolet-visible absorption spectrum (hereinafter, simply referred to as absorption spectrum) of [Ir(mppm)$_2$(acac)] that is the phosphorescent compound in a dichloromethane solution of [Ir(mppm)$_2$(acac)]. The absorption spectrum was measured with the use of an ultraviolet-visible light spectrophotometer (V-550, manufactured by JASCO Corporation) in the state where the dichloromethane solution (0.10 mmol/L) was put in a quartz cell at room temperature.

<Emission Spectrum>

FIGS. 39A and 39B each also show an emission spectrum of a thin film of 2mDBTPDBq-II that is the first organic compound (an emission spectrum 14), an emission spectrum of a thin film of PCBA1BP that is the second organic compound (an emission spectrum 15), an emission spectrum of a thin film of αNBA1BP that is the second organic compound (an emission spectrum 16), an emission spectrum of a thin film of a mixed material of 2mDBTPDBq-II and PCBA1BP (an emission spectrum 17), and an emission spectrum of a thin film of a mixed material of 2mDBTPDBq-II and αNBA1BP (an emission spectrum 18). In FIG. 39A, the horizontal axis represents wavelength (nm), and the vertical axes represent molar absorption coefficient ε ($M^{-1} \cdot cm^{-1}$) and emission intensity (arbitrary unit). In FIG. 39B, the horizontal axis represents energy (eV), and the vertical axes represent molar absorption coefficient ε ($M^{-1} \cdot cm^{-1}$) and emission intensity (arbitrary unit).

As can be seen from the absorption spectrum in FIG. 39A, [Ir(mppm)$_2$(acac)] has a broad absorption band at around 490 nm. This absorption band is considered to greatly contribute to light emission.

It is found that the emission spectrum of the mixed material of 2mDBTPDBq-II and PCBA1BP (the emission spectrum 17) and the emission spectrum of the mixed material of 2mDBTPDBq-II and αNBA1BP (the emission spectrum 18) each peak at a longer wavelength (lower energy) than the emission spectrum of either organic compound alone. This indicates that an exciplex is formed by mixing 2mDBTPDBq-II with PCBA1BP. It also indicates that an exciplex is formed by mixing 2mDBTPDBq-II with αNBA1BP.

It is found that the peak of the emission spectrum of each mixed material has a large overlap with the absorption band in the absorption spectrum of [Ir(mppm)$_2$(acac)] which is considered to greatly contribute to light emission. Thus, it is indicated that the light-emitting element including [Ir(mppm)$_2$(acac)] and the mixed material of 2mDBTPDBq-II and PCBA1BP and the light-emitting element including [Ir(mppm)$_2$(acac)] and the mixed material of 2mDBTPDBq-II and αNBA1BP have high energy transfer efficiency because they each transfer energy by utilizing the overlap between the emission spectrum of the mixed material and the absorption spectrum of the phosphorescent compound. Accordingly, it is indicated that a light-emitting element having high external quantum efficiency can be obtained.

The emission spectrum 18 peaks at a shorter wavelength (higher energy) than the emission spectrum 17. In addition, the peak of the emission spectrum 18 is closer to the absorption band than the peak of the emission spectrum 17. Specifically, the difference between the peak of the absorption band in the absorption spectrum (a shoulder peak at around 490 nm) and the peak of the emission spectrum 17 is 0.15 eV, and the difference between the peak of the absorption band in the absorption spectrum (a shoulder peak at around 490 nm) and the peak of the emission spectrum 18 is 0.01 eV.

The difference between the peaks of the emission spectrum 17 and the emission spectrum 18 is considered to be due to the difference between the HOMO levels of PCBA1BP and cNBA1BP. Specifically, the HOMO level of PCBA1BP is −5.43 eV, whereas the HOMO level of αNBA1BP is −5.52 eV (each calculated by cyclic voltammetry (CV) measurement). Because αNBA1BP has a lower (deeper) HOMO level than PCBA1BP, the emission spectrum 18 is considered to peak at a shorter wavelength (higher energy) than the emission spectrum 17.

EXAMPLE 12

In this example, light-emitting elements of one embodiment of the present invention will be described with reference to FIG. 15. The materials used in this example are used in the above examples, and therefore the chemical formulae thereof are omitted here.

Methods for manufacturing a light-emitting element 9 and a light-emitting element 10 of this example will be described below.

(Light-emitting Element 9)

First, a film of ITSO was formed over a glass substrate 1100 by a sputtering method, so that a first electrode 1101 functioning as an anode was formed. Note that the thickness was set to 110 nm and the electrode area was set to 2 mm×2 mm.

Next, as pretreatment for forming the light-emitting element over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, BPAFLP and molybdenum(VI) oxide were co-evaporated to form a hole-injection layer 1111 over the first electrode 1101. The thickness of the hole-injection layer 1111 was set to 40 nm, and the weight ratio of BPAFLP to molybdenum oxide was adjusted to 4:2 (=BPAFLP:molybdenum oxide).

Next, over the hole-injection layer 1111, a film of BPAFLP was formed to a thickness of 20 nm to form a hole-transport layer 1112.

Furthermore, 2mDBTPDBq-II, PCBA1BP, and [Ir(mppm)$_2$(acac)] were co-evaporated to form a light-emitting layer 1113 over the hole-transport layer 1112. Here, the weight ratio of 2mDBTPDBq-II to PCBA1BP and [Ir(mppm)$_2$(acac)] was adjusted to 0.8:0.2:0.05 (=2mDBTPDBq-II:PCBA1BP:[Ir(mppm)$_2$(acac)]). The thickness of the light-emitting layer 1113 was set to 40 nm.

Further, over the light-emitting layer 1113, a film of 2mDBTPDBq-II was formed to a thickness of 10 nm to form a first electron-transport layer 1114a.

Next, over the first electron-transport layer 1114a, a film of BPhen was formed to a thickness of 20 nm to form a second electron-transport layer 1114b.

Further, over the second electron-transport layer 1114b, a film of LiF was formed by evaporation to a thickness of 1 nm to form an electron-injection layer 1115.

Lastly, an aluminum film was formed by evaporation to a thickness of 200 nm as a second electrode 1103 functioning as a cathode. Thus, the light-emitting element 9 of this example was fabricated.

(Light-emitting Element 10)

A light-emitting layer 1113 of the light-emitting element 10 was formed by co-evaporating 2mDBTPDBq-II, αNBA1BP, and [Ir(mppm)$_2$(acac)]. Here, the weight ratio of 2mDBTPDBq-II to αNBA1BP and [Ir(mppm)$_2$(acac)] was adjusted to 0.8:0.2:0.05 (=2mDBTPDBq-II:αNBA1BP:[Ir (mppm)$_2$(acac)]). The thickness of the light-emitting layer 1113 was set to 40 nm. Components other than the light-emitting layer 1113 were manufactured in a manner similar to that of the light-emitting element 9.

Note that, in all the above evaporation steps, evaporation was performed by a resistance-heating method.

Figure 44:
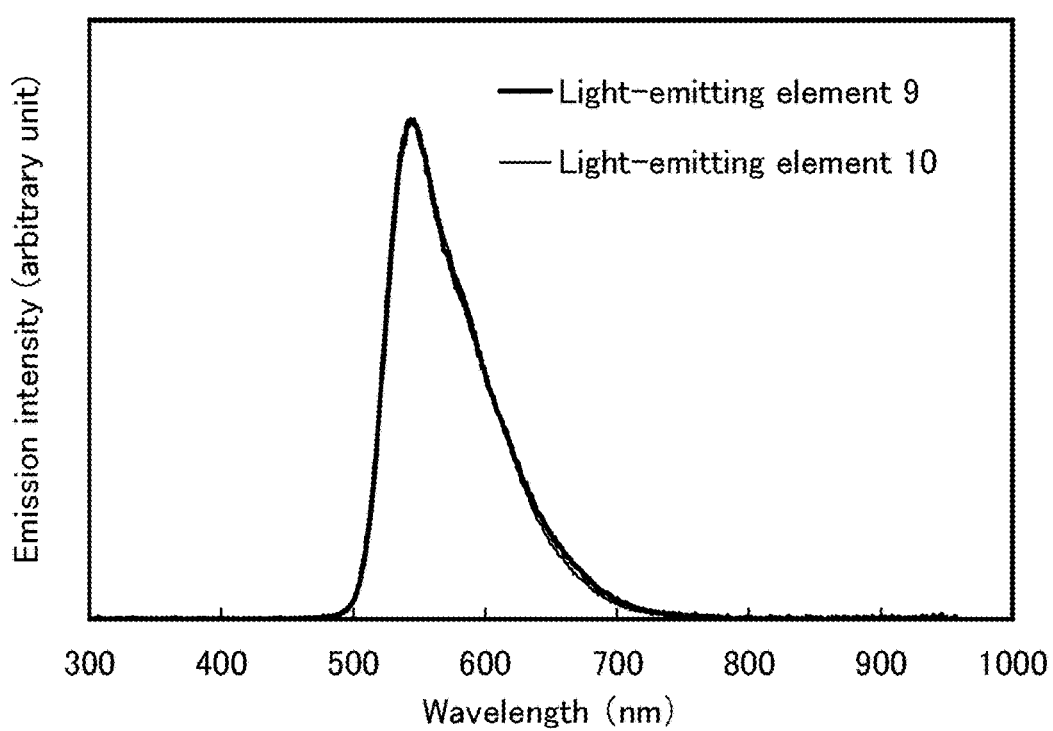
FIG. 44 shows emission spectra of the light-emitting elements of Example 12.

Table 11 shows element structures of the light-emitting element 9 and the light-emitting element 10 obtained as described above.

obtained by applying a current of 0.1 mA. In FIG. 44, the horizontal axis represents wavelength (nm), and the vertical axis represents emission intensity (arbitrary unit). As shown in Table 12, the CIE chromaticity coordinates of the light-emitting element 9 at a luminance of 1100 cd/m$^2$ were (x, y)=(0.43, 0.56), and the CIE chromaticity coordinates of the light-emitting element 10 at a luminance of 860 cd/m$^2$ were (x, y)=(0.43, 0.56). These results show that yellow-green light emission originating from [Ir(mppm)$_2$(acac)] was obtained from the light-emitting element 9 and the light-emitting element 10.

TABLE 11

| | first elecrtrode | hole-injection layer | hole-transport layer | light-emitting layer | first electron-transport layer | second electron-transport layer | electron-injection layer | second electrode |
|---|---|---|---|---|---|---|---|---|
| light-emitting element 9 | ITSO 110 nm | BPAFLP:MoOx (=4:2) 40 nm | BPAFLP 20 nm | 2mDBTPDBq-II:PCBA1BP:[Ir(mppm)$_2$(acac)] (=0.8:0.2:0.05) 40 nm | 2mDBTPDBq-II 10 nm | BPhen 20 nm | LiF 1 nm | Al 200 nm |
| light-emitting element 10 | ITSO 110 nm | BPAFLP:MoOx (=4:2) 40 nm | BPAFLP 20 nm | 2mDBTPDBq-II:αNBA1BP:[Ir(mppm)$_2$(acac)] (=0.8:0.2:0.05) 40 nm | 2mDBTPDBq-II 10 nm | BPhen 20 nm | LiF 1 nm | Al 200 nm |

In a glove box containing a nitrogen atmosphere, these light-emitting elements were sealed so as not to be exposed to air. Then, operation characteristics of these light-emitting elements were measured. Note that the measurements were carried out at room temperature (in the atmosphere kept at 25° C.).

Figure 40:
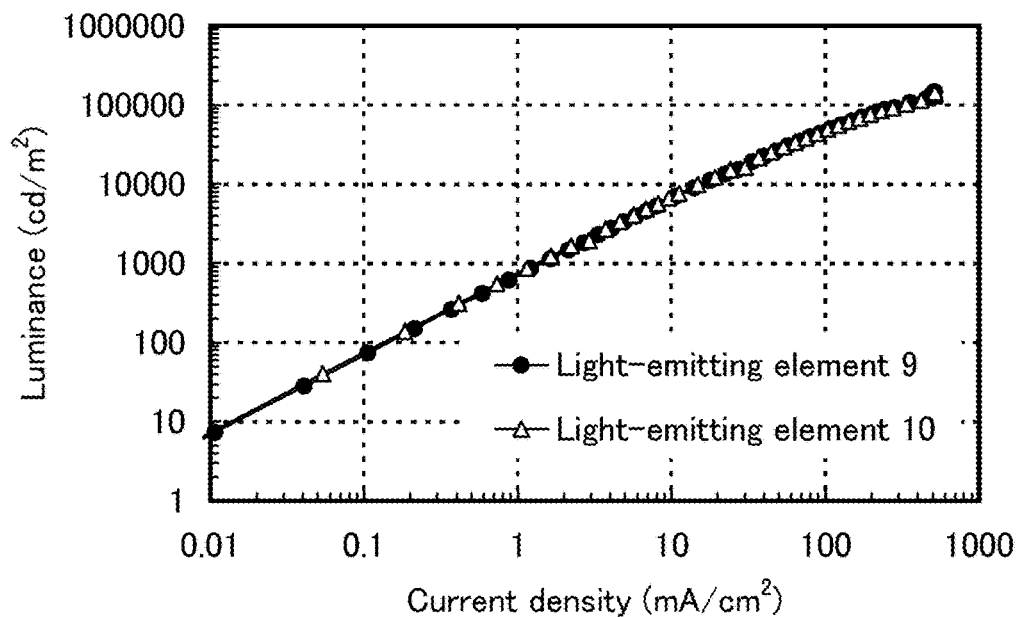
FIG. 40 shows current density-luminance characteristics of light-emitting elements of Example 12.
Figure 41:
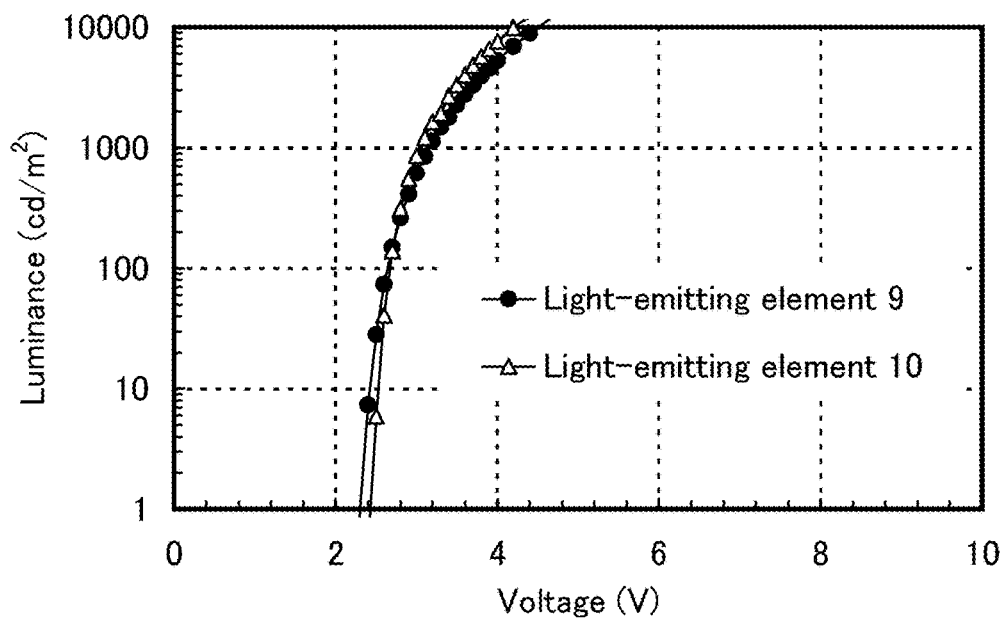
FIG. 41 shows voltage-luminance characteristics of the light-emitting elements of Example 12.
Figure 42:
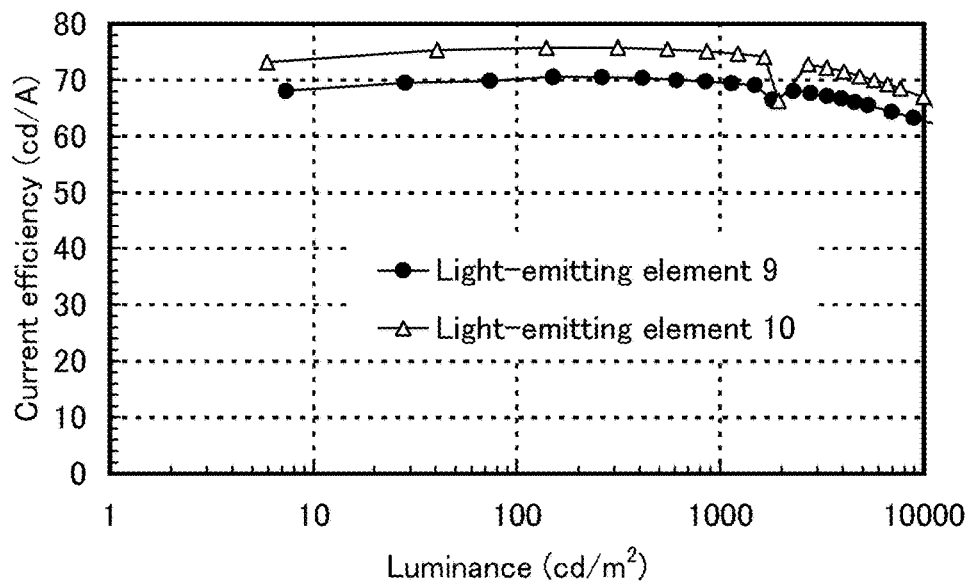
FIG. 42 shows luminance-current efficiency characteristics of the light-emitting elements of Example 12.
Figure 43:
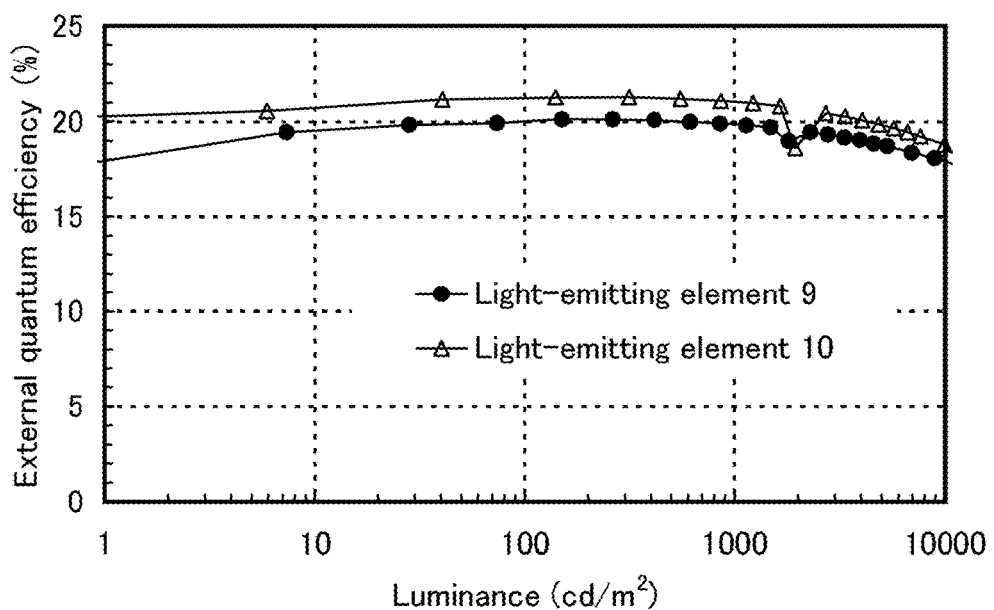
FIG. 43 shows luminance-external quantum efficiency characteristics of the light-emitting elements of Example 12.

FIG. 40 shows current density-luminance characteristics of the light-emitting element 9 and the light-emitting element 10. In FIG. 40, the horizontal axis represents current density (mA/cm$^2$), and the vertical axis represents luminance (cd/m$^2$). FIG. 41 shows voltage-luminance characteristics thereof. In FIG. 41, the horizontal axis represents voltage (V), and the vertical axis represents luminance (cd/m$^2$). FIG. 42 shows luminance-current efficiency characteristics thereof. In FIG. 42, the horizontal axis represents luminance (cd/m$^2$), and the vertical axis represents current efficiency (cd/A). FIG. 43 shows luminance-external quantum efficiency characteristics thereof. In FIG. 43, the horizontal axis represents luminance (cd/m$^2$), and the vertical axis represents external quantum efficiency (%).

Further, Table 12 shows the voltage (V), current density (mA/cm$^2$), CIE chromaticity coordinates (x, y), current efficiency (cd/A), power efficiency (lm/W), and external quantum efficiency (%) of each of the light-emitting element 9 and the light-emitting element 10 at a luminance of around 1000 cd/m$^2$.

As can be seen from Table 12 and FIGS. 40 to 43, the light-emitting element 9 and the light-emitting element 10 each have high current efficiency, high power efficiency, and high external quantum efficiency.

In each of the light-emitting element 9 and the light-emitting element 10, PCBA1BP or αNBA1BP, 2mDBTPDBq-II, and [Ir(mppm)$_2$(acac)] described in Example 11 are used for the light-emitting layer. As described in Example 11, the emission spectrum of the mixed material of 2mDBTPDBq-II and PCBA1BP or αNBA1BP (the emission spectrum of an exciplex) has a large overlap with the absorption band in the absorption spectrum of [Ir(mppm)$_2$(acac)] which is considered to greatly contribute to light emission. The light-emitting element 9 and the light-emitting element 10 are considered to have high energy transfer efficiency because they each transfer energy by utilizing the overlap, and therefore have high external quantum efficiency.

The above results show that an element having high external quantum efficiency can be obtained by application of one embodiment of the present invention.

Figure 45:
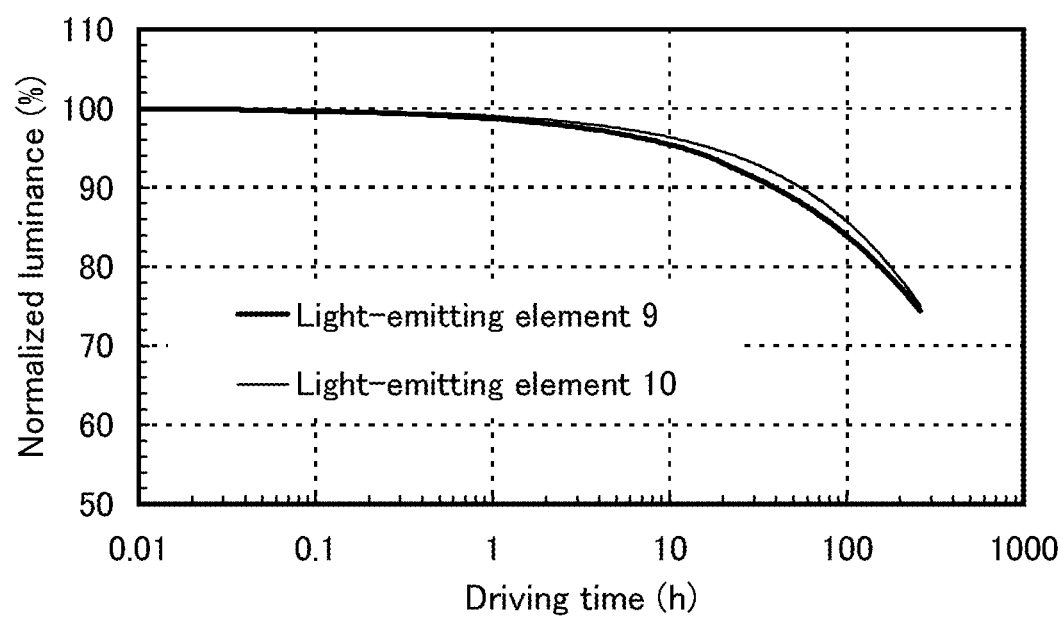
FIG. 45 shows results of reliability tests of the light-emitting elements of Example 12.

Next, the light-emitting element 9 and the light-emitting element 10 were subjected to reliability tests. Results of the reliability tests are shown in FIG. 45. In FIG. 45, the vertical axis represents normalized luminance (%) with an initial luminance of 100%, and the horizontal axis represents driving time (h) of the elements.

TABLE 12

| | voltage (V) | current density (mA/cm$^2$) | chromaticity coordinates (x, y) | luminance (cd/m$^2$) | current efficiency (cd/A) | power efficiency (lm/W) | external quantum efficiency (%) |
|---|---|---|---|---|---|---|---|
| light-emitting element 9 | 3.2 | 1.6 | (0.43, 0.56) | 1100 | 69 | 68 | 20 |
| light-emitting element 10 | 3.0 | 1.1 | (0.43, 0.56) | 860 | 75 | 79 | 21 |

FIG. 44 shows emission spectra of the light-emitting element 9 and the light-emitting element 10 which were In the reliability tests, the light-emitting element 9 and the light-emitting element 10 were driven under the conditions where the initial luminance was set to 5000 cd/m² and the current density was constant.

The luminance of the light-emitting element 9 after 260 hours was 74% of the initial luminance. The luminance of the light-emitting element 10 after 260 hours was 75% of the initial luminance. From the results, the light-emitting element 9 and the light-emitting element 10 are found to have a long lifetime.

The above results show that an element having high reliability can be obtained by application of one embodiment of the present invention.

EXAMPLE 13

In this example, examples of combinations of a first organic compound, a second organic compound, and a phosphorescent compound which can be used for a light-emitting element of one embodiment of the present invention will be described with reference to FIGS. 46A and 46B.

The phosphorescent compound used in this example is (acetylacetonato)bis(6-tert-butyl-4-phenylpyrimidinato) iridium(III) (abbreviation: [Ir(tBuppm)$_2$(acac)]). The first organic compound used in this example is 2mDBTPDBq-II. Two kinds of second organic compounds, NPB and 2,7-bis [N-(4-diphenylaminophenyl)-N-phenylamino]-spiro-9,9'-bifluorene (abbreviation: DPA2SF), are used in this example. Chemical formulae of the materials used in this example are shown below. Note that the chemical formulae of the materials used in the above examples are omitted here.

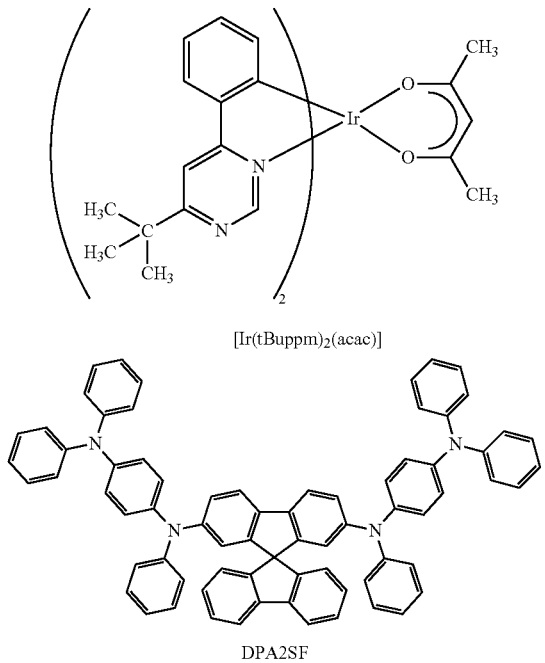

[Ir(tBuppm)$_2$(acac)]

DPA2SF

<Absorption Spectrum>

Figure 46A:
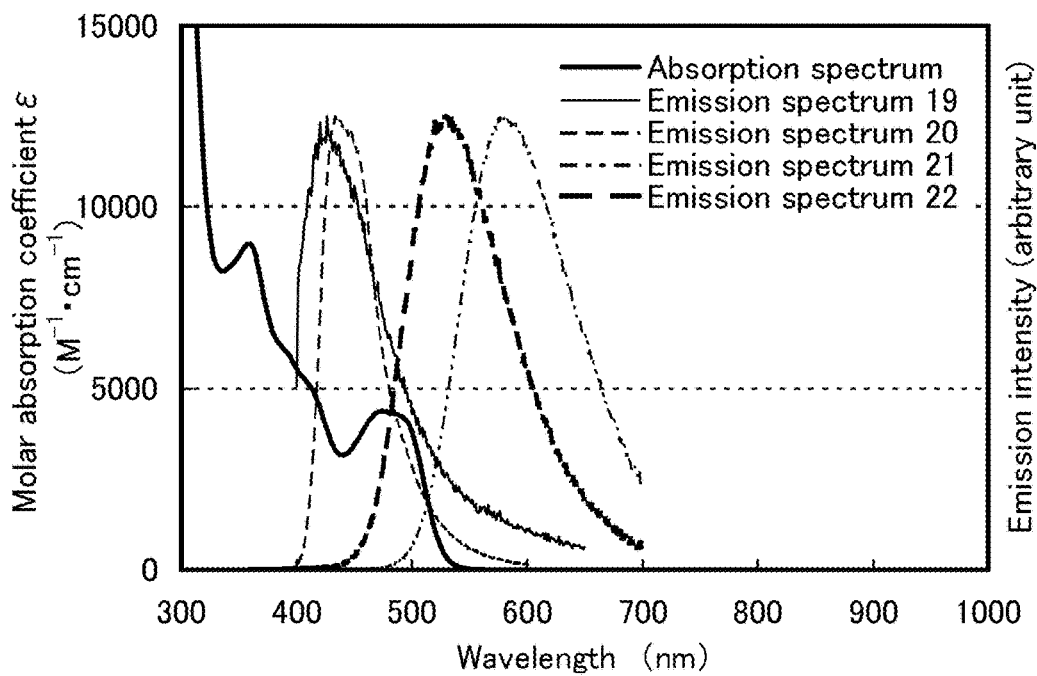
FIGS. 46A and 46B each show an absorption spectrum and emission spectra according to Example 13.
Figure 46B:
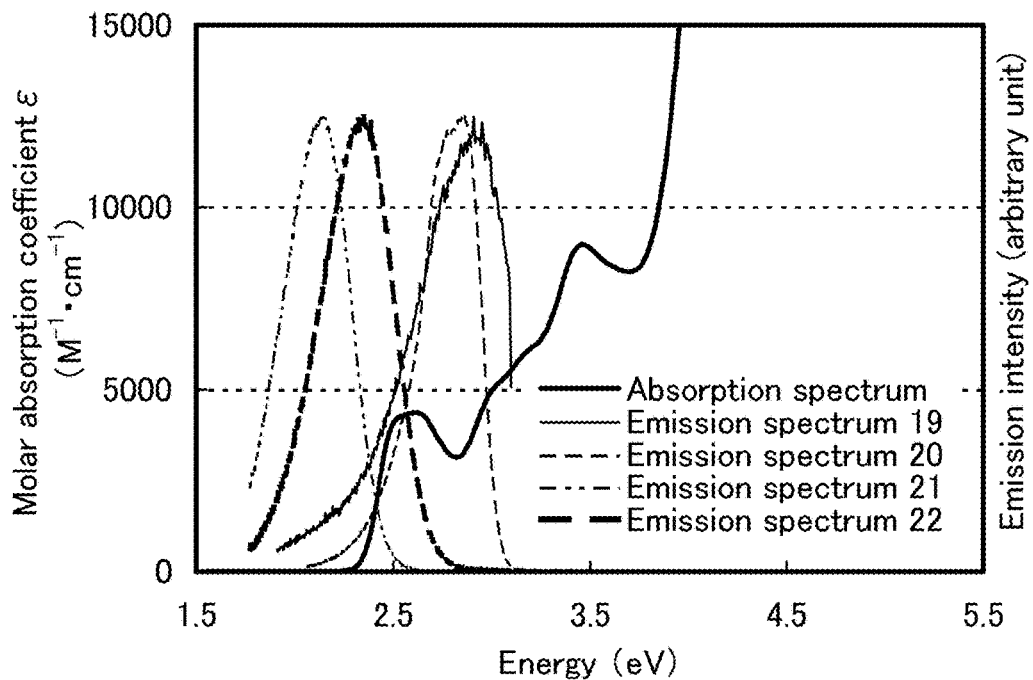

FIGS. 46A and 46B each show an ultraviolet-visible absorption spectrum (hereinafter, simply referred to as absorption spectrum) of [Ir(tBuppm)$_2$(acac)] that is the phosphorescent compound in a dichloromethane solution of [Ir(tBuppm)$_2$(acac)]. The absorption spectrum was measured with the use of an ultraviolet-visible light spectrophotometer (V-550, manufactured by JASCO Corporation) in the state where the dichloromethane solution (0.093 mmol/L) was put in a quartz cell at room temperature.

<Emission Spectrum>

FIGS. 46A and 46B each also show an emission spectrum of a thin film of 2mDBTPDBq-II that is the first organic compound (an emission spectrum 19), an emission spectrum of a thin film of DPA2SF that is the second organic compound (an emission spectrum 20), an emission spectrum of a thin film of a mixed material of 2mDBTPDBq-II and DPA2SF (an emission spectrum 21), and an emission spectrum of a thin film of a mixed material of 2mDBTPDBq-II and NPB (an emission spectrum 22). In FIG. 46A, the horizontal axis represents wavelength (nm), and the vertical axes represent molar absorption coefficient ε (M$^{-1}$·cm$^{-1}$) and emission intensity (arbitrary unit). In FIG. 46B, the horizontal axis represents energy (eV), and the vertical axes represent molar absorption coefficient ε (M$^{-1}$·cm$^{-1}$) and emission intensity (arbitrary unit).

As can be seen from the absorption spectrum in FIG. 46A, [Ir(tBuppm)$_2$(acac)] has a broad absorption band at around 490 nm. This absorption band is considered to greatly contribute to light emission.

It is found that the emission spectrum of the mixed material of 2mDBTPDBq-II and DPA2SF (the emission spectrum 21) peaks at a longer wavelength (lower energy) than the emission spectrum of either organic compound alone. This indicates that an exciplex is formed by mixing 2mDBTPDBq-II with DPA2SF.

It is known that the emission spectrum of NPB alone peaks at around 430 nm. FIG. 46A indicates that because the emission spectrum of the mixed material of 2mDBTPDBq-II and NPB (the emission spectrum 22) peaks at a wavelength longer than 430 nm, an exciplex is formed by mixing 2mDBTPDBq-II with NPB.

It is found that the peak of the emission spectrum of the mixed material has a large overlap with the absorption band in the absorption spectrum of [Ir(tBuppm)$_2$(acac)] which is considered to greatly contribute to light emission. Thus, it is indicated that the light-emitting element including [Ir (tBuppm)$_2$(acac)] and the mixed material of 2mDBTPDBq-II and DPA2SF and the light-emitting element including [Ir(tBuppm)$_2$(acac)] and the mixed material of 2mDBTP-DBq-II and NPB have high energy transfer efficiency because they each transfer energy by utilizing the overlap between the emission spectrum of the mixed material and the absorption spectrum of the phosphorescent compound. Accordingly, it is indicated that a light-emitting element having high external quantum efficiency can be obtained.

The emission spectrum 22 peaks at a shorter wavelength (higher energy) than the emission spectrum 21. In addition, the peak of the emission spectrum 22 is closer to the absorption band than the peak of the emission spectrum 21. The above findings show that in FIGS. 46A and 46B, the emission spectrum 22 has the largest overlap with the absorption band in the absorption spectrum which greatly contributes to light emission. Specifically, the difference between the peak of the absorption band in the absorption spectrum and the peak of the emission spectrum 21 is 0.39 eV, and the difference between the peak of the absorption band in the absorption spectrum and the peak of the emission spectrum 22 is 0.19 eV.

The difference between the peaks of the emission spectrum 21 and the emission spectrum 22 is considered to be due to the difference between the HOMO levels of DPA2SF and NPB used as the second organic compounds. Specifically, the HOMO level of DPA2SF is −5.09 eV, whereas the HOMO level of NPB is −5.38 eV (each calculated by cyclic voltammetry (CV) measurement). Because NPB has a lower (deeper) HOMO level than DPA2SF, the emission spectrum 22 is considered to peak at a shorter wavelength (higher energy) than the emission spectrum 21.

The above description indicates that the light-emitting element including [Ir(tBuppm)$_2$(acac)] and the mixed material of 2mDBTPDBq-II and NPB has higher energy transfer efficiency than the light-emitting element including [Ir(tBuppm)$_2$(acac)] and the mixed material of 2mDBTPDBq-II and DPA2SF because the former transfers energy by utilizing a larger overlap between the emission spectrum of the mixed material and the absorption spectrum of the phosphorescent compound. Accordingly, it is indicated that a light-emitting element having high external quantum efficiency can be obtained.

In addition, this example reveals that the overlap between the emission spectrum of the mixed material of the first organic compound and the second organic compound and the absorption spectrum of the phosphorescent compound can be increased simply by changing the second organic compound without changing the first organic compound. In other words, it is indicated that a combination capable of increasing the overlap can be obtained simply by changing the second organic compound even in the case of changing the emission color of the phosphorescent compound (the position of the absorption band in the absorption spectrum which greatly contributes to light emission), and that a light-emitting element having high external quantum efficiency and long lifetime can be obtained.

EXAMPLE 14

In this example, light-emitting elements of one embodiment of the present invention will be described with reference to FIG. 15. The materials used in this example are used in the above examples, and therefore the chemical formulae thereof are omitted here.

Methods for manufacturing a light-emitting element 11 and a light-emitting element 12 of this example will be described below.

(Light-emitting Element 11)

First, a film of ITSO was formed over a glass substrate 1100 by a sputtering method, so that a first electrode 1101 functioning as an anode was formed. Note that the thickness was set to 110 nm and the electrode area was set to 2 mm×2 mm.

Next, as pretreatment for forming the light-emitting element over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, DBT3P-II and molybdenum(VI) oxide were co-evaporated to form a hole-injection layer 1111 over the first electrode 1101. The thickness of the hole-injection layer 1111 was set to 40 nm, and the weight ratio of DBT3P-II to molybdenum oxide was adjusted to 4:2 (=DBT3P-II:molybdenum oxide).

Next, over the hole-injection layer 1111, a film of BPAFLP was formed to a thickness of 20 nm to form a hole-transport layer 1112.

Furthermore, 2mDBTPDBq-II, DPA2SF, and [Ir(tBuppm)$_2$(acac)] were co-evaporated to form a light-emitting layer 1113 over the hole-transport layer 1112. Here, the weight ratio of 2mDBTPDBq-II to DPA2SF and [Ir(tBuppm)$_2$(acac)] was adjusted to 0.8:0.2:0.05 (=2mDBTPDBq-II:DPA2SF:[Ir(tBuppm)$_2$(acac)]). The thickness of the light-emitting layer 1113 was set to 40 nm.

Further, over the light-emitting layer 1113, a film of 2mDBTPDBq-II was formed to a thickness of 10 nm to form a first electron-transport layer 1114a.

Next, over the first electron-transport layer 1114a, a film of BPhen was formed to a thickness of 20 nm to form a second electron-transport layer 1114b.

Further, over the second electron-transport layer 1114b, a film of LiF was formed by evaporation to a thickness of 1 nm to form an electron-injection layer 1115.

Lastly, an aluminum film was formed by evaporation to a thickness of 200 nm as a second electrode 1103 functioning as a cathode. Thus, the light-emitting element 11 of this example was fabricated.

(Light-emitting Element 12)

A light-emitting layer 1113 of the light-emitting element 12 was formed by co-evaporating 2mDBTPDBq-II, NPB, and [Ir(tBuppm)$_2$(acac)]. Here, the weight ratio of 2mDBTPDBq-II to NPB and [Ir(tBuppm)$_2$(acac)] was adjusted to 0.8:0.2:0.05 (=2mDBTPDBq-II:NPB:[Ir(tBuppm)$_2$(acac)]). The thickness of the light-emitting layer 1113 was set to 40 nm. Components other than the light-emitting layer 1113 were manufactured in a manner similar to that of the light-emitting element 11.

Note that, in all the above evaporation steps, evaporation was performed by a resistance-heating method.

Table 13 shows element structures of the light-emitting element 11 and the light-emitting element 12 obtained as described above.

TABLE 13

| | first elecrtrode | hole-injection layer | hole-transport layer | light-emitting layer | first electron-transport layer | second electron-transport layer | electron-injection layer | second electrode |
|---|---|---|---|---|---|---|---|---|
| light-emitting element 11 | ITSO 110 nm | DBT3P-II:MoOx (=4:2) 40 nm | BPAFLP 20 nm | 2mDBTPDBq-II:DPA2SF:[Ir(tBuppm)$_2$(acac)] (=0.8:0.2:0.05) 40 nm | 2mDBTPDBq-II 10 nm | BPhen 20 nm | LiF 1 nm | Al 200 nm |
| light-emitting | ITSO 110 nm | DBT3P-II:MoOx (=4:2) | BPAFLP 20 nm | 2mDBTPDBq-II:NPB:[Ir(tBuppm)$_2$(acac)] (=0.8:0.2:0.05) | 2mDBTPDBq-II | BPhen 20 nm | LiF 1 nm | Al 200 nm |

TABLE 13-continued

| | first elecrtrode | hole-injection layer | hole-transport layer | light-emitting layer | first electron-transport layer | second electron-transport layer | electron-injection layer | second electrode |
|---|---|---|---|---|---|---|---|---|
| element 12 | | 40 nm | | 40 nm | | 10 nm | | |

In a glove box containing a nitrogen atmosphere, these light-emitting elements were sealed so as not to be exposed to air. Then, operation characteristics of these light-emitting elements were measured. Note that the measurements were carried out at room temperature (in the atmosphere kept at 25° C.).

Figure 47:
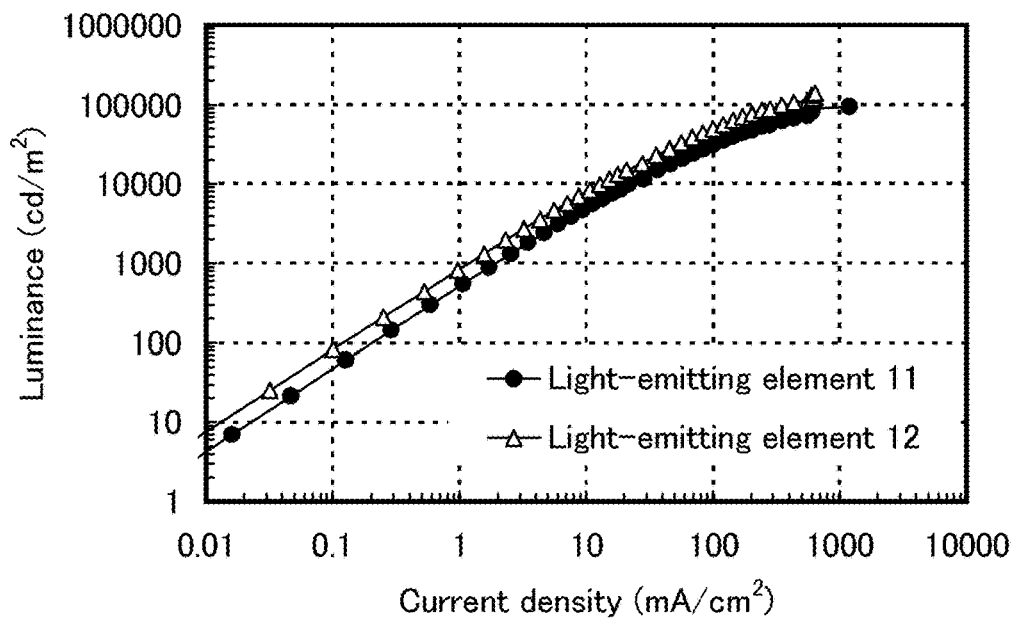
FIG. 47 shows current density-luminance characteristics of light-emitting elements of Example 14.
Figure 48:
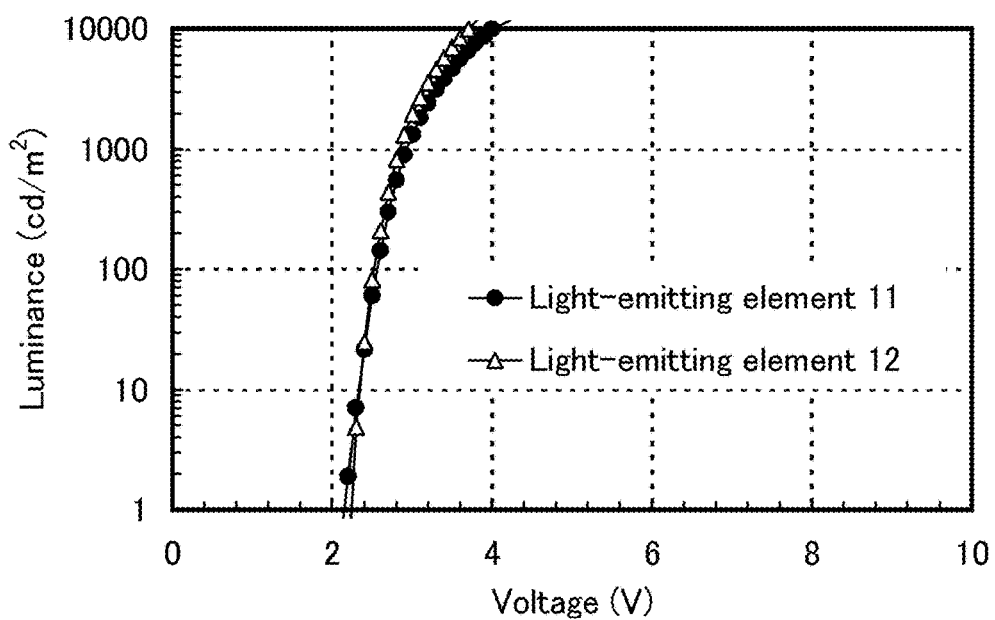
FIG. 48 shows voltage-luminance characteristics of the light-emitting elements of Example 14.
Figure 49:
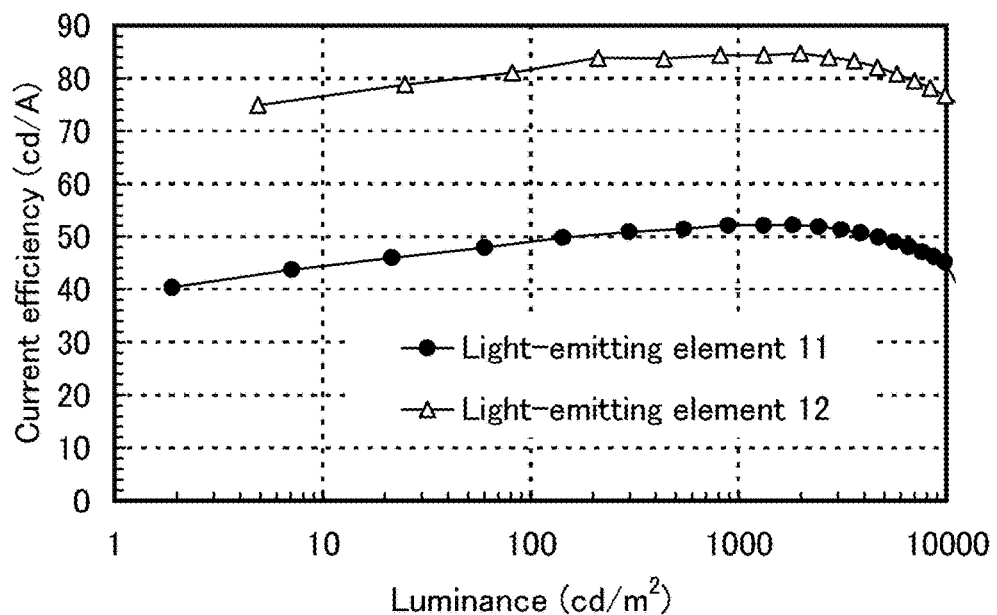
FIG. 49 illustrates luminance-current efficiency characteristics of the light-emitting elements of Example 14.
Figure 50:
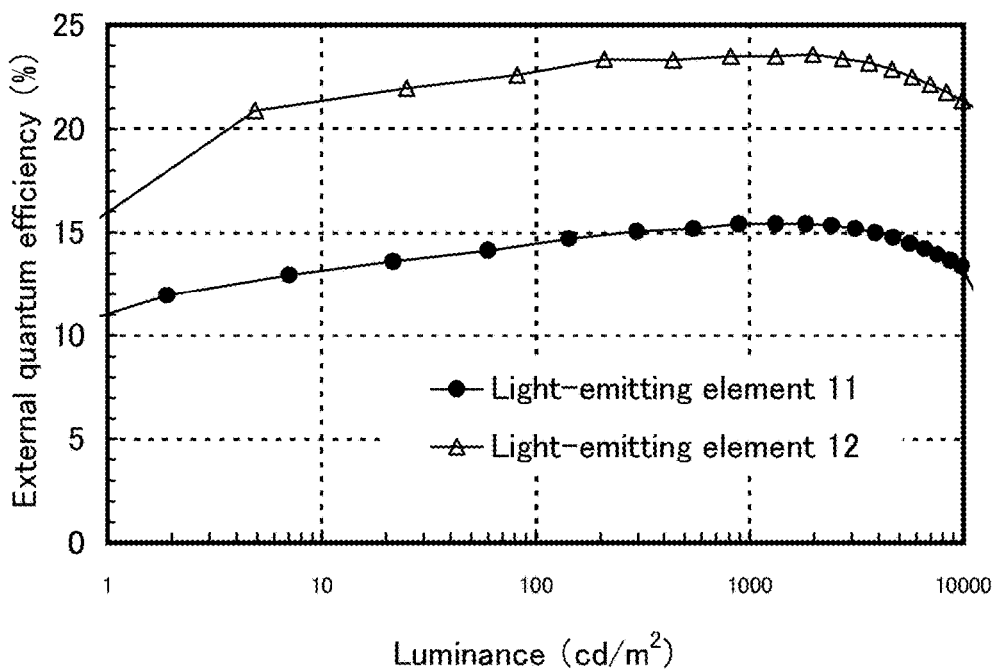
FIG. 50 shows luminance-external quantum efficiency characteristics of the light-emitting elements of Example 14.

FIG. 47 shows current density-luminance characteristics of the light-emitting element 11 and the light-emitting element 12. In FIG. 47, the horizontal axis represents current density (mA/cm$^2$), and the vertical axis represents luminance (cd/m$^2$). FIG. 48 shows voltage-luminance characteristics thereof. In FIG. 48, the horizontal axis represents voltage (V), and the vertical axis represents luminance (cd/m$^2$). FIG. 49 shows luminance-current efficiency characteristics thereof. In FIG. 49, the horizontal axis represents luminance (cd/m$^2$), and the vertical axis represents current efficiency (cd/A). FIG. 50 shows luminance-external quantum efficiency characteristics thereof. In FIG. 50, the horizontal axis represents luminance (cd/m$^2$), and the vertical axis represents external quantum efficiency (%).

Further, Table 14 shows the voltage (V), current density (mA/cm$^2$), CIE chromaticity coordinates (x, y), current efficiency (cd/A), power efficiency (lm/W), and external quantum efficiency (%) of each of the light-emitting element 11 and the light-emitting element 12 at a luminance of around 1000 cd/m$^2$.

TABLE 14

| | voltage (V) | current density (mA/cm$^2$) | chromaticity coordinates (x, y) | luminance (cd/m$^2$) | current efficiency (cd/A) | power efficiency (lm/W) | external quantum efficiency (%) |
|---|---|---|---|---|---|---|---|
| light-emitting element 11 | 2.9 | 1.7 | (0.43, 0.56) | 890 | 52 | 56 | 15 |
| light-emitting element 12 | 2.8 | 1.0 | (0.42, 0.57) | 820 | 84 | 95 | 23 |

Figure 51:
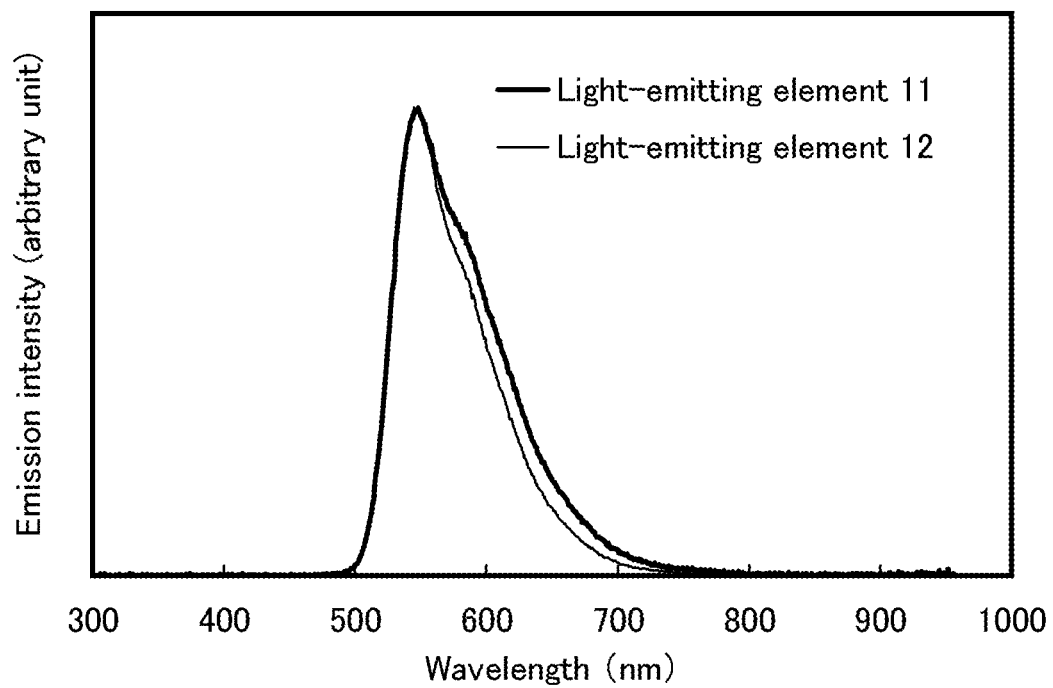
FIG. 51 shows emission spectra of the light-emitting elements of Example 14.

FIG. 51 shows emission spectra of the light-emitting element 11 and the light-emitting element 12 which were obtained by applying a current of 0.1 mA. In FIG. 51, the horizontal axis represents wavelength (nm), and the vertical axis represents emission intensity (arbitrary unit). As shown in Table 14, the CIE chromaticity coordinates of the light-emitting element 11 at a luminance of 890 cd/m$^2$ were (x, y)=(0.43, 0.56), and the CIE chromaticity coordinates of the light-emitting element 12 at a luminance of 820 cd/m$^2$ were (x, y)=(0.42, 0.57). These results show that yellow-green light emission originating from [Ir(tBuppm)$_2$(acac)] was obtained from the light-emitting element 11 and the light-emitting element 12.

As can be seen from Table 14 and FIGS. 47 to 50, the light-emitting element 11 and the light-emitting element 12 each have high current efficiency, high power efficiency, and high external quantum efficiency.

In each of the light-emitting element 11 and the light-emitting element 12, DPA2SF or NPB, 2mDBTPDBq-II, and [Ir(tBuppm)$_2$(acac)] described in Example 13 are used for the light-emitting layer. As described in Example 13, the emission spectrum of the mixed material of 2mDBTPDBq-II and DPA2SF or NPB (the emission spectrum of an exciplex) has a large overlap with the absorption band in the absorption spectrum of [Ir(tBuppm)$_2$(acac)] which is considered to greatly contribute to light emission. The light-emitting element 11 and the light-emitting element 12 are considered to have high energy transfer efficiency because they each transfer energy by utilizing the overlap, and therefore have high external quantum efficiency. In particular, the emission spectrum of the mixed material of 2mDBTPDBq-II and NPB has a larger overlap with the absorption band than the emission spectrum of the mixed material of 2mDBTPDBq-II and DPA2SF. Therefore, the light-emitting element 12 is considered to have higher energy transfer efficiency than the light-emitting element 11 because the former transfers energy by utilizing the larger overlap, and therefore have high quantum efficiency. With reference to the results in Example 13 as well, it is found that the difference between the energy of the peak of the emission spectrum of an exciplex and the energy of the peak of the absorption band on the lowest energy side in the absorption spectrum is preferably 0.3 eV or less.

In this example, a light-emitting element having further high external quantum efficiency is obtained simply by changing the second organic compound (using NPB instead of DPA2SF) without changing the first organic compound (corresponding to 2mDBTPDBq-II).

The above results show that an element having high external quantum efficiency can be obtained by application of one embodiment of the present invention.

EXAMPLE 15

In this example, examples of combinations of a first organic compound, a second organic compound, and a phosphorescent compound which can be used for a light-emitting element of one embodiment of the present invention will be described with reference to FIGS. 52A and 52B.

The phosphorescent compound used in this example is [Ir(mppr-Me)$_2$(dpm)]). Two kinds of first organic compounds, 2mDBTPDBq-II and 2-[4-(dibenzothiophen-4-yl)phenyl]-1-phenyl-1H-benzoimidazole (abbreviation: DBTBIm-II), are used in this example. The second organic compound used in this example is 4,4',4"-tris[N-(1-naphthyl)-N-phenylamino]triphenylamine (abbreviation: 1'-TNATA). Chemical formulae of the materials used in this example are shown below. Note that the chemical formulae of the materials used in the above example are omitted here.

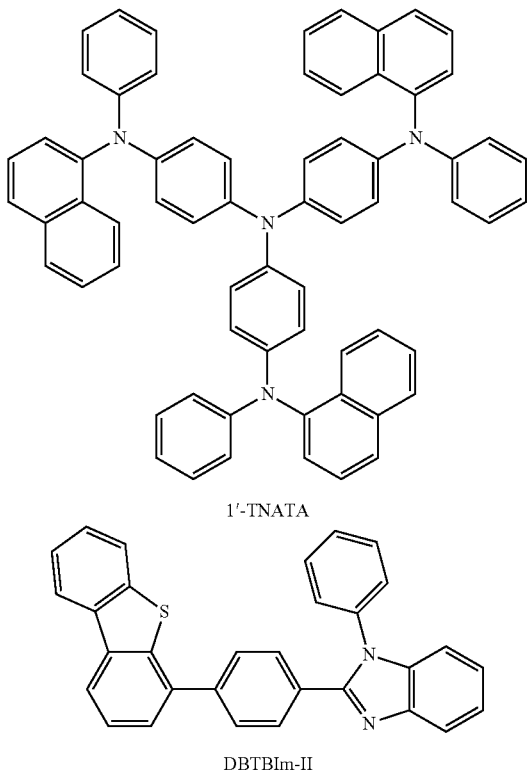

<Absorption Spectrum>

Figure 52A:
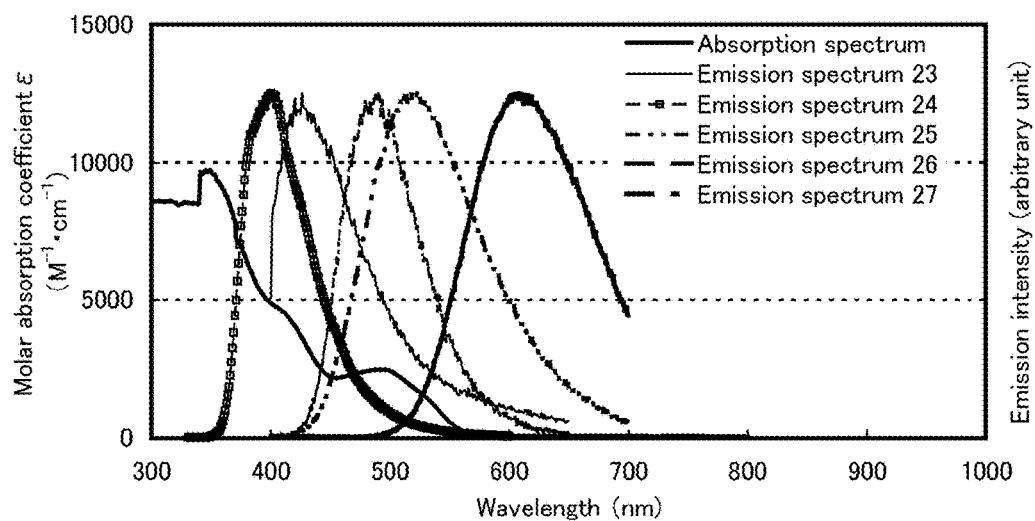
FIGS. 52A and 52B each show an absorption spectrum and emission spectra according to Example 15.
Figure 52B:
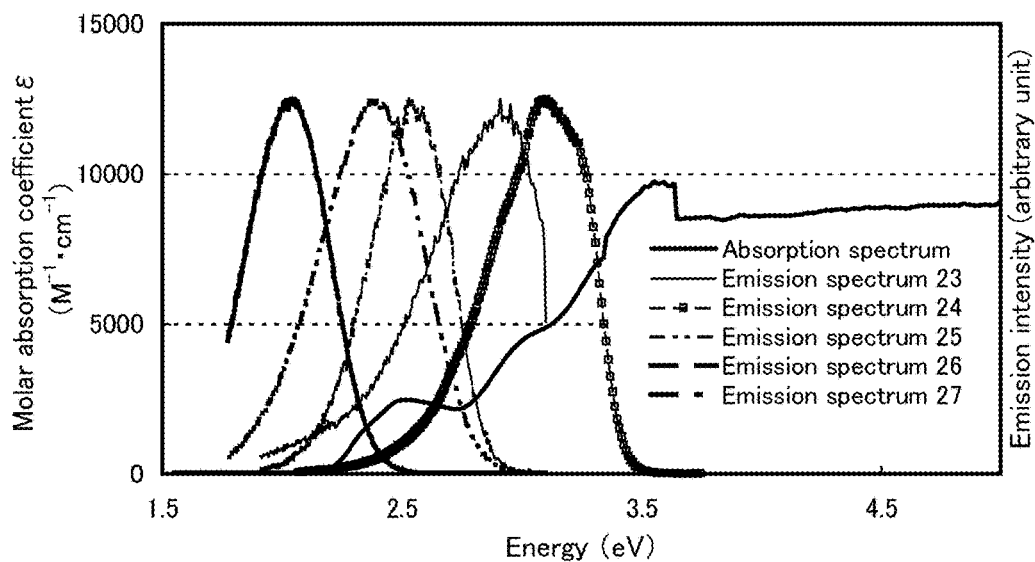

FIGS. 52A and 52B each show an ultraviolet-visible absorption spectrum (hereinafter, simply referred to as absorption spectrum) of [Ir(mppr-Me)$_2$(dpm)] that is the phosphorescent compound in a dichloromethane solution of [Ir(mppr-Me)$_2$(dpm)]. The absorption spectrum was measured with the use of an ultraviolet-visible light spectrophotometer (V-550, manufactured by JASCO Corporation) in the state where the dichloromethane solution (0.093 mmol/L) was put in a quartz cell at room temperature.

<Emission Spectrum>

FIGS. 52A and 52B each also show an emission spectrum of a thin film of 2mDBTPDBq-II that is the first organic compound (an emission spectrum 23), an emission spectrum of a thin film of DBTBIm-II that is the first organic compound (an emission spectrum 24), an emission spectrum of a thin film of 1'-TNATA that is the second organic compound (an emission spectrum 25), an emission spectrum of a thin film of a mixed material of 2mDBTPDBq-II and 1'-TNATA (an emission spectrum 26), and an emission spectrum of a thin film of a mixed material of DBTBIm-II and 1'-TNATA (an emission spectrum 27). In FIG. 52A, the horizontal axis represents wavelength (nm), and the vertical axes represent molar absorption coefficient ε (M$^{-1}$·cm$^{-1}$) and emission intensity (arbitrary unit). In FIG. 52B, the horizontal axis represents energy (eV), and the vertical axes represent molar absorption coefficient ε (M$^{-1}$·cm$^{-1}$) and emission intensity (arbitrary unit).

As can be seen from the absorption spectrum in FIG. 52A, [Ir(mppr-Me)$_2$(dpm)] has a broad absorption band at around 520 nm. This absorption band is considered to greatly contribute to light emission.

It is found that the emission spectrum of the mixed material of 2mDBTPDBq-II and 1'-TNATA (the emission spectrum 26) and the emission spectrum of the mixed material of DBTBIm-II and 1'-TNATA (the emission spectrum 27) each peak at a longer wavelength (lower energy) than the emission spectrum of either organic compound alone. This indicates that an exciplex is formed by mixing 2mDBTPDBq-II with 1'-TNATA. It also indicates that an exciplex is formed by mixing DBTBIm-II with 1'-TNATA.

It is found that the peak of the emission spectrum of each mixed material has a large overlap with the absorption band in the absorption spectrum of [Ir(mppr-Me)$_2$(dpm)] which is considered to greatly contribute to light emission. Thus, it is indicated that the light-emitting element including [Ir(mppr-Me)$_2$(dpm)] and the mixed material of 2mDBTPDBq-II and 1'-TNATA and the light-emitting element including [Ir(mppr-Me)$_2$(dpm)] and the mixed material of DBTBIm-II and 1'-TNATA have high energy transfer efficiency because they each transfer energy by utilizing the overlap between the emission spectrum of the mixed material and the absorption spectrum of the phosphorescent compound. Accordingly, it is indicated that a light-emitting element having high external quantum efficiency can be obtained.

The emission spectrum 27 peaks at a shorter wavelength (higher energy) than the emission spectrum 26. In addition, the peak of the emission spectrum 27 is closer to the absorption band than the peak of the emission spectrum 26. The above findings show that in FIGS. 52A and 52B, the emission spectrum 27 has the largest overlap with the absorption band in the absorption spectrum which greatly contributes to light emission. Specifically, the difference between the peak of the absorption band in the absorption spectrum (a shoulder peak at around 520 nm) and the peak of the emission spectrum 26 is 0.35 eV, and the difference between the peak of the absorption band in the absorption spectrum (a shoulder peak at around 520 nm) and the peak of the emission spectrum 27 is 0.01 eV.

The difference between the peaks of the emission spectrum 26 and the emission spectrum 27 is considered to be due to the difference between the LUMO levels of 2mDBTPDBq-II used as the first organic compound and DBTBIm-II. Specifically, the LUMO level of 2mDBTPDBq-II is −2.95 eV, whereas the LUMO level of DBTBIm-II is −2.52 eV (each calculated by cyclic voltammetry (CV) measurement). Because DBTBIm-II has a higher (shallower) LUMO level than 2mDBTPDBq-II, it is considered that the emission spectrum of the mixed material of DBTBIm-II with 1'-TNATA having a high HOMO level does not peak at too long a wavelength (i.e., the emission spectrum 27 peaks at a shorter wavelength than the emission spectrum 26.

The above description indicates that the light-emitting element including [Ir(mppr-Me)$_2$(dpm)] and the mixed material of DBTBIm-II and 1'-TNATA has higher energy transfer efficiency than the light-emitting element including [Ir(mppr-Me)$_2$(dpm)] and the mixed material of 2mDBTPDBq-II and 1'-TNATA because the former transfers energy by utilizing a larger overlap between the emission spectrum of the mixed material and the absorption spectrum of the phosphorescent compound. Accordingly, it is indicated that a light-emitting element having high external quantum efficiency can be obtained.

In addition, this example reveals that the overlap between the emission spectrum of the mixed material of the first organic compound and the second organic compound and the absorption spectrum of the phosphorescent compound can be increased simply by changing the first organic compound without changing the second organic compound. In other words, it is indicated that a combination capable of increasing the overlap can be obtained simply by changing the first organic compound even in the case of changing the emission color of the phosphorescent compound (the position of the absorption band in the absorption spectrum which greatly contributes to light emission), and that a light-emitting element having high external quantum efficiency and long lifetime can be obtained.

EXAMPLE 16

In this example, light-emitting elements of one embodiment of the present invention will be described with reference to FIG. 15. The materials used in this example are used in the above examples, and therefore the chemical formulae thereof are omitted here.

Methods for manufacturing a light-emitting element 13 and a light-emitting element 14 of this example will be described below.

(Light-emitting Element 13)

First, a film of ITSO was formed over a glass substrate 1100 by a sputtering method, so that a first electrode 1101 functioning as an anode was formed. Note that the thickness was set to 110 nm and the electrode area was set to 2 mm×2 mm.

Next, as pretreatment for forming the light-emitting element over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, BPAFLP and molybdenum(VI) oxide were co-evaporated to form a hole-injection layer 1111 over the first electrode 1101. The thickness of the hole-injection layer 1111 was set to 40 nm, and the weight ratio of BPAFLP to molybdenum oxide was adjusted to 4:2 (=BPAFLP:molybdenum oxide).

Next, over the hole-injection layer 1111, a film of BPA-FLP was formed to a thickness of 20 nm to form a hole-transport layer 1112.

Furthermore, 2mDBTPDBq-II, 1'-TNATA, and [Ir(mppr-Me)$_2$(dpm)] were co-evaporated to form a light-emitting layer 1113 over the hole-transport layer 1112. Here, the weight ratio of 2mDBTPDBq-II to 1'-TNATA and [Ir(mppr-Me)$_2$(dpm)] was adjusted to 0.8:0.2:0.05 (=2mDBTPDBq-II:1'-TNATA:[Ir(mppr-Me)$_2$(dpm)]). The thickness of the light-emitting layer 1113 was set to 20 nm.

Further, over the light-emitting layer 1113, a film of 2mDBTPDBq-II was formed to a thickness of 30 nm to form a first electron-transport layer 1114a.

Next, over the first electron-transport layer 1114a, a film of BPhen was formed to a thickness of 20 nm to form a second electron-transport layer 1114b.

Further, over the second electron-transport layer 1114b, a film of LiF was formed by evaporation to a thickness of 1 nm to form an electron-injection layer 1115.

Lastly, an aluminum film was formed by evaporation to a thickness of 200 nm as a second electrode 1103 functioning as a cathode. Thus, the light-emitting element 13 of this example was fabricated.

(Light-emitting Element 14)

A light-emitting layer 1113 of the light-emitting element 14 was formed by co-evaporating DBTBIm-II, 1'-TNATA, and [Ir(mppr-Me)$_2$(dpm)]. Here, the weight ratio of DBTBIm-II to 1'-TNATA and [Ir(mppr-Me)$_2$(dpm)] was adjusted to 0.8:0.2:0.05 (=DBTBIm-II:1'-TNATA:[Ir(mppr-Me)$_2$(dpm)]). The thickness of the light-emitting layer 1113 was set to 20 nm.

A first electron-transport layer 1114a of the light-emitting element 14 was formed by forming a film of DBTBIm-II to a thickness of 30 nm. Components other than the light-emitting layer 1113 and the first electron-transport layer 1114a were manufactured in a manner similar to that of the light-emitting element 13.

Note that, in all the above evaporation steps, evaporation was performed by a resistance-heating method.

Table 15 shows element structures of the light-emitting element 13 and the light-emitting element 14 obtained as described above.

TABLE 15

| | first elecrtrode | hole-injection layer | hole-transport layer | light-emitting layer | first electron-transport layer | second electron-transport layer | electron-injection layer | second electrode |
|---|---|---|---|---|---|---|---|---|
| light-emitting element 13 | ITSO 110 nm | BPAFLP:MoOx (=4:2) 40 nm | BPAFLP 20 nm | 2mDBTPDBq-II:1'-TNATA:[Ir(mppr-Me)$_2$(dpm)] (=0.8:0.2:0.05) 20 nm | 2mDBTPDBq-II 30 nm | BPhen 20 nm | LiF 1 nm | Al 200 nm |
| light-emitting element 14 | ITSO 110 nm | BPAFLP:MoOx (=4:2) 40 nm | BPAFLP 20 nm | DBTBIm-II:1'-TNATA:[Ir(mppr-Me)$_2$(dpm)] (=0.8:0.2:0.05) 20 nm | DBTBIm-II 30 nm | BPhen 20 nm | LiF 1 nm | Al 200 nm |

In a glove box containing a nitrogen atmosphere, these light-emitting elements were sealed so as not to be exposed to air. Then, operation characteristics of these light-emitting elements were measured. Note that the measurements were carried out at room temperature (in the atmosphere kept at 25° C.).

Figure 53:
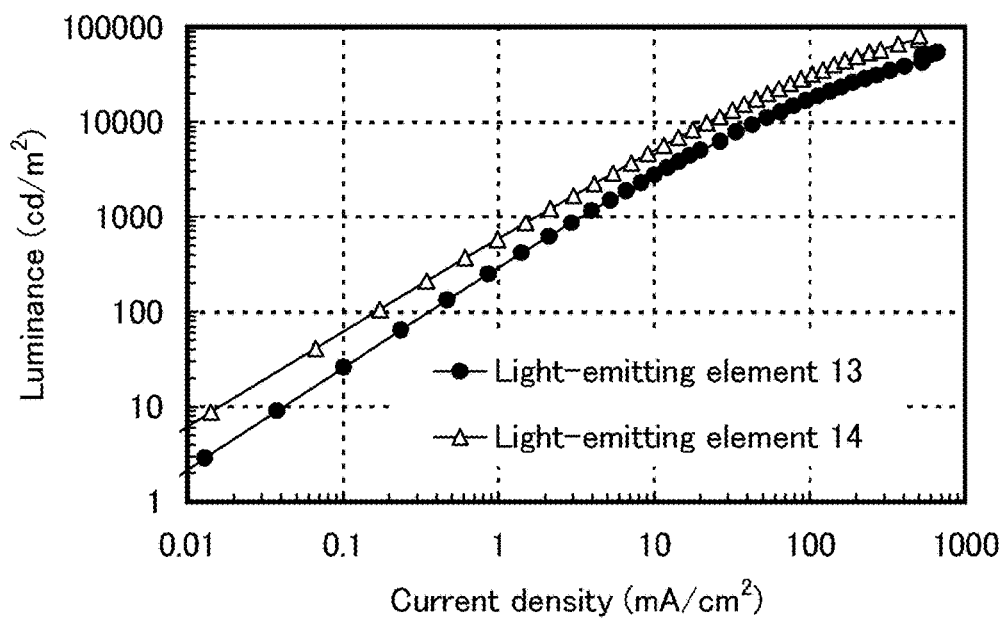
FIG. 53 shows current density-luminance characteristics of light-emitting elements of Example 16.
Figure 54:
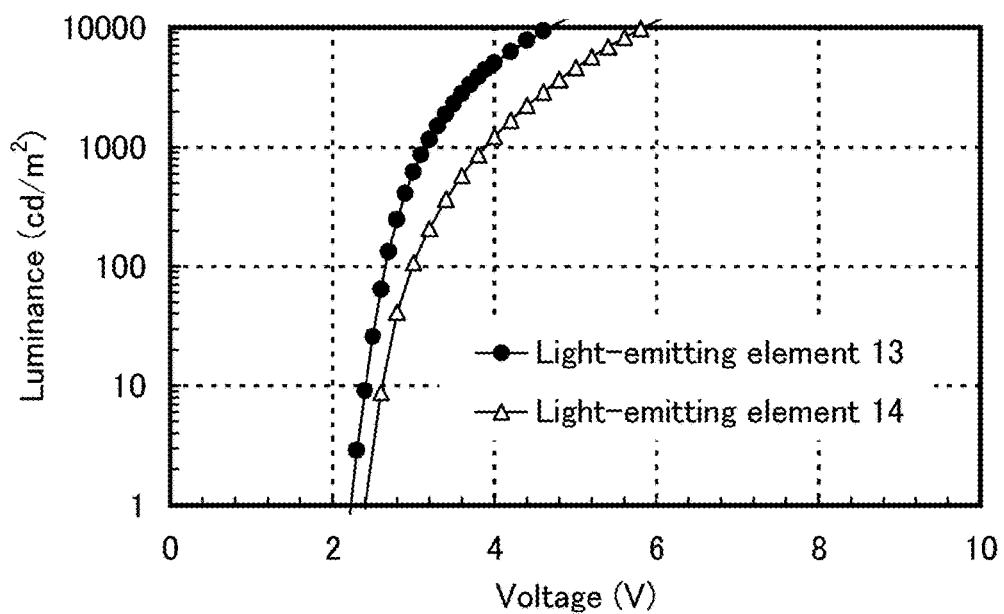
FIG. 54 shows voltage-luminance characteristics of the light-emitting elements of Example 16.
Figure 55:
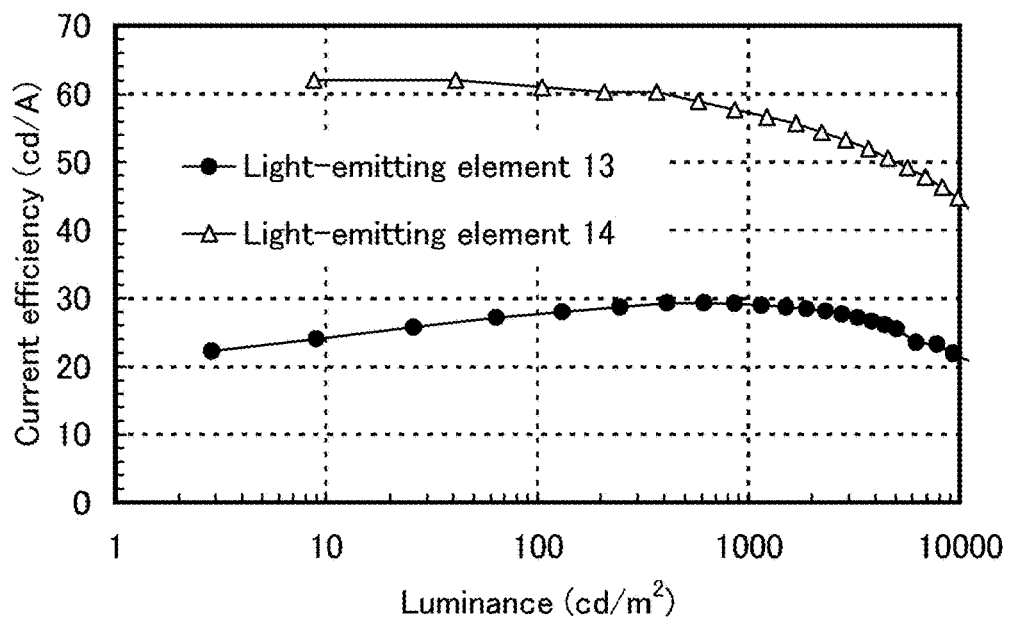
FIG. 55 shows luminance-current efficiency characteristics of the light-emitting elements of Example 16.
Figure 56:
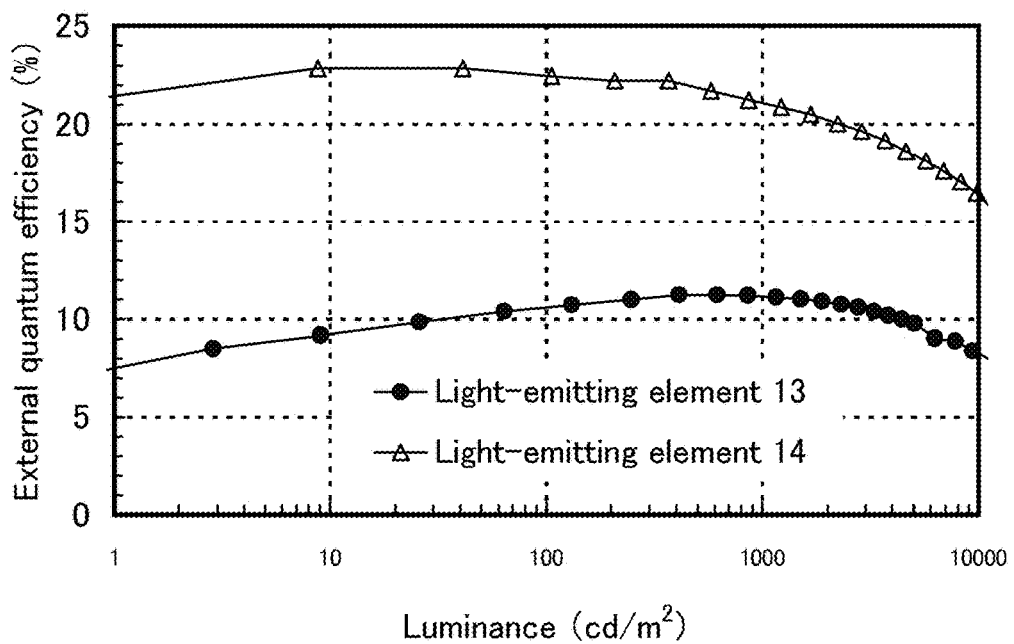
FIG. 56 shows luminance-external quantum efficiency characteristics of the light-emitting elements of Example 16.

FIG. 53 shows current density-luminance characteristics of the light-emitting element 13 and the light-emitting element 14. In FIG. 53, the horizontal axis represents current density (mA/cm$^2$), and the vertical axis represents luminance (cd/m$^2$). FIG. 54 shows voltage-luminance characteristics thereof. In FIG. 54, the horizontal axis represents voltage (V), and the vertical axis represents luminance (cd/m$^2$). FIG. 55 shows luminance-current efficiency characteristics thereof. In FIG. 55, the horizontal axis represents luminance (cd/m$^2$), and the vertical axis represents current efficiency (cd/A). FIG. 56 shows luminance-external quantum efficiency characteristics thereof. In FIG. 56, the horizontal axis represents luminance (cd/m$^2$), and the vertical axis represents external quantum efficiency (%).

Further, Table 16 shows the voltage (V), current density (mA/cm$^2$), CIE chromaticity coordinates (x, y), current efficiency (cd/A), power efficiency (lm/W), and external quantum efficiency (%) of each of the light-emitting element 13 and the light-emitting element 14 at a luminance of 860 cd/m$^2$.

TABLE 16

|  | voltage (V) | current density (mA/cm$^2$) | chromaticity coordinates (x, y) | luminance (cd/m$^2$) | current efficiency (cd/A) | power efficiency (lm/W) | external quantum efficiency (%) |
| --- | --- | --- | --- | --- | --- | --- | --- |
| light-emitting element 13 | 3.1 | 2.9 | (0.53, 0.46) | 860 | 29 | 30 | 11 |
| light-emitting element 14 | 3.8 | 1.5 | (0.53, 0.46) | 860 | 58 | 48 | 21 |

Figure 57:
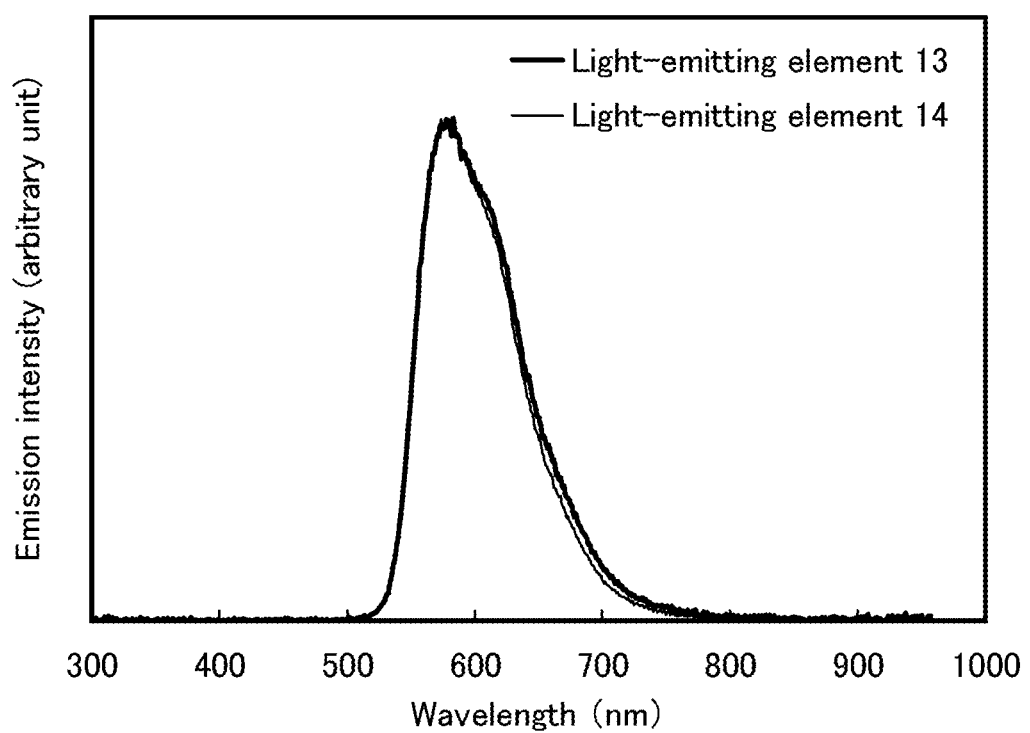
FIG. 57 shows emission spectra of the light-emitting elements of Example 16.

FIG. 57 shows emission spectra of the light-emitting element 13 and the light-emitting element 14 which were obtained by applying a current of 0.1 mA. In FIG. 57, the horizontal axis represents wavelength (nm), and the vertical axis represents emission intensity (arbitrary unit). As shown in Table 16, the CIE chromaticity coordinates of each of the light-emitting element 13 and the light-emitting element 14 at a luminance of 860 cd/m$^2$ were (x, y)=(0.53, 0.46). These results show that orange light emission originating from [Ir(mppr-Me)$_2$(dpm)] was obtained from the light-emitting element 13 and the light-emitting element 14.

As can be seen from Table 16 and FIGS. 53 to 56, the light-emitting element 13 and the light-emitting element 14 each have high current efficiency, high power efficiency, and high external quantum efficiency.

In each of the light-emitting element 13 and the light-emitting element 14, 2mDBTPDBq-II or DBTBIm-II, 1'-TNATA, and [Ir(mppr-Me)$_2$(dpm)] described in Example 15 are used for the light-emitting layer. As described in Example 15, the emission spectrum of the mixed material of 2mDBTPDBq-II or DBTBIm-II and 1'-TNATA (the emission spectrum of an exciplex) has a large overlap with the absorption band in the absorption spectrum of [Ir(mppr-Me)$_2$(dpm)] which is considered to greatly contribute to light emission. The light-emitting element 13 and the light-emitting element 14 are considered to have high energy transfer efficiency because they each transfer energy by utilizing the overlap, and therefore have high external quantum efficiency. In particular, the emission spectrum of the mixed material of DBTBIm-II and 1'-TNATA has a larger overlap with the absorption band than the emission spectrum of the mixed material of 2mDBTPDBq-II and 1'-TNATA. Therefore, the light-emitting element 14 is considered to have higher energy transfer efficiency than the light-emitting element 13 because the former transfers energy by utilizing the larger overlap, and therefore have high quantum efficiency. With reference to the results in Example 15 as well, it is found that the difference between the energy of the peak of the emission spectrum of an exciplex and the energy of the peak of the absorption band on the lowest energy side in the absorption spectrum is preferably 0.3 eV or less.

In this example, a light-emitting element having further high external quantum efficiency is obtained simply by changing the first organic compound (using DBTBIm-II instead of 2mDBTPDBq-II) without changing the second organic compound (corresponding to 1'-TNATA).

The above results show that an element having high external quantum efficiency can be obtained by application of one embodiment of the present invention.

EXAMPLE 17

In this example, examples of combinations of a first organic compound, a second organic compound, and a phosphorescent compound which can be used for a light-emitting element of one embodiment of the present invention will be described with reference to FIGS. 58A and 58B.

The phosphorescent compound used in this example is [Ir(mppr-Me)$_2$(dpm)]. The first organic compound used in this example is 2mDBTPDBq-II. Two kinds of second organic compounds, PCBNBB and 9-phenyl-9H-3-(9-phenyl-9H-carbazol-3-yl)carbazole (abbreviation: PCCP), are used in this example. A chemical formula of a material used in this example is shown below. Note that structural formulae of the materials used in the above examples are omitted here.

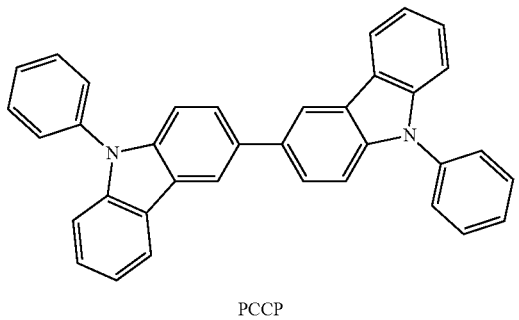

PCCP

<Absorption Spectrum>

Figure 58A:
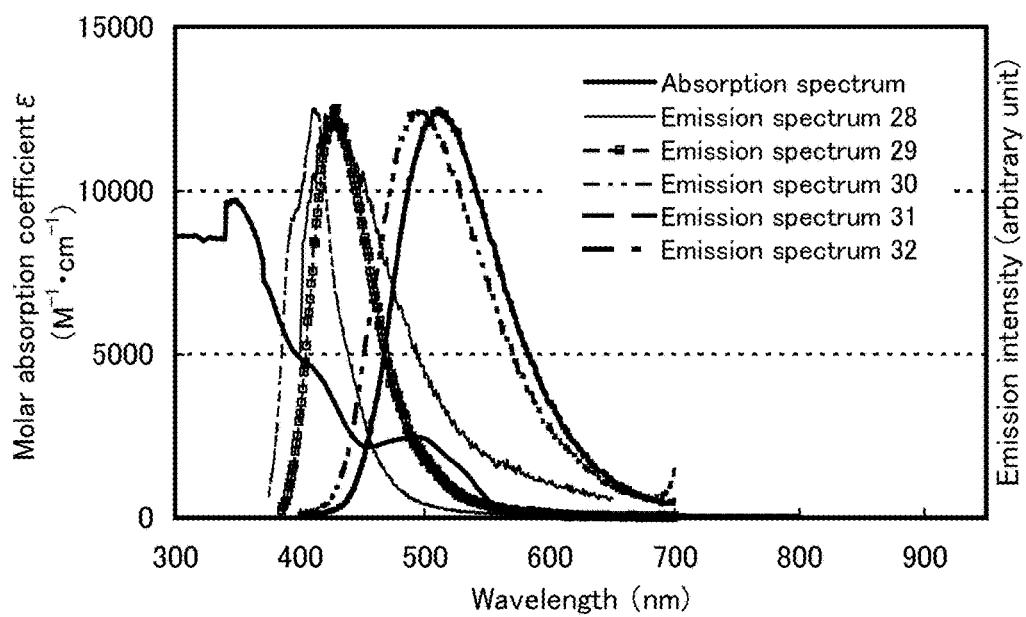
FIGS. 58A and 58B each show an absorption spectrum and emission spectrum according to Example 17.
Figure 58B:
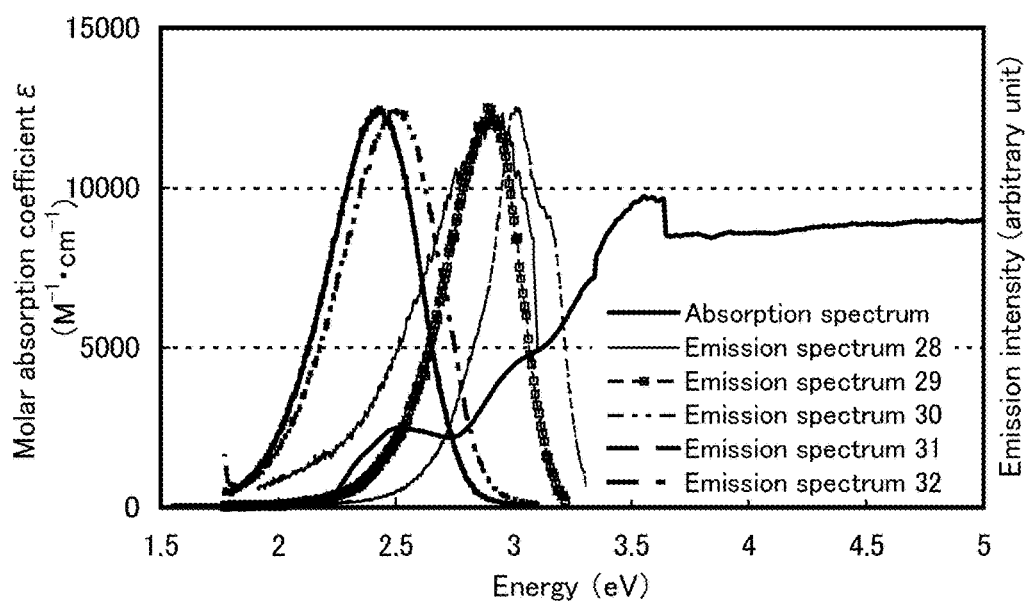

FIGS. 58A and 58B each show an ultraviolet-visible absorption spectrum (hereinafter, simply referred to as absorption spectrum) of [Ir(mppr-Me)$_2$(dpm)] that is the phosphorescent compound in a dichloromethane solution of [Ir(mppr-Me)$_2$(dpm)]. The absorption spectrum was measured with the use of an ultraviolet-visible light spectrophotometer (V-550, manufactured by JASCO Corporation) in the state where the dichloromethane solution (0.093 mmol/L) was put in a quartz cell at room temperature.

<Emission Spectrum>

FIGS. 58A and 58B each also show an emission spectrum of a thin film of 2mDBTPDBq-II that is the first organic compound (an emission spectrum 28), an emission spectrum of a thin film of PCBNBB that is the second organic compound (an emission spectrum 29), an emission spectrum of a thin film of PCCP that is the second organic compound (an emission spectrum 30), an emission spectrum of a thin film of a mixed material of 2mDBTPDBq-II and PCBNBB (an emission spectrum 31), and an emission spectrum of a thin film of a mixed material of 2mDBTPDBq-II and PCCP (an emission spectrum 32). In FIG. 58A, the horizontal axis represents wavelength (nm), and the vertical axes represent molar absorption coefficient ε ($M^{-1} \cdot cm^{-1}$) and emission intensity (arbitrary unit). In FIG. 58B, the horizontal axis represents energy (eV), and the vertical axes represent molar absorption coefficient ε ($M^{-1} \cdot cm^{-1}$) and emission intensity (arbitrary unit).

As can be seen from the absorption spectrum in FIG. 58A, [Ir(mppr-Me)$_2$(dpm)] has a broad absorption band at around 500 nm. This absorption band is considered to greatly contribute to light emission.

It is found that the emission spectrum of the mixed material of 2mDBTPDBq-II and PCBNBB (an emission spectrum 31) and the emission spectrum of the mixed material of 2mDBTPDBq-II and PCCP (an emission spectrum 32) each peak at a longer wavelength (lower energy) than the emission spectrum of either organic compound alone. This indicates that an exciplex is formed by mixing 2mDBTPDBq-II with PCBNBB. It also indicates that an exciplex is formed by mixing 2mDBTPDBq-II with PCCP.

It is found that the peak of the emission spectrum of each mixed material has a large overlap with the absorption band in the absorption spectrum of [Ir(mppr-Me)$_2$(dpm)] which is considered to greatly contribute to light emission. Thus, it is indicated that the light-emitting element including [Ir(mppr-Me)$_2$(dpm)] and the mixed material of 2mDBTPDBq-II and PCBNBB and the light-emitting element including [Ir(mppr-Me)$_2$(dpm)] and the mixed material of 2mDBTPDBq-II and PCCP have high energy transfer efficiency because they each transfer energy by utilizing the overlap between the emission spectrum of the mixed material and the absorption spectrum of the phosphorescent compound. Accordingly, it is indicated that a light-emitting element having high external quantum efficiency can be obtained.

In addition, this example indicates that either an aromatic amine based compound or a carbazole compound can be used as one of the first and second organic compounds which form an exciplex.

EXAMPLE 18

In this example, light-emitting elements of one embodiment of the present invention will be described with reference to FIG. 15. The materials used in this example are used in the above examples, and therefore the chemical formulae thereof are omitted here.

Methods for manufacturing a light-emitting element 15 and a light-emitting element 16 of this example will be described below.

(Light-emitting Element 15)

First, a film of ITSO was formed over a glass substrate 1100 by a sputtering method, so that a first electrode 1101 functioning as an anode was formed. Note that the thickness was set to 110 nm and the electrode area was set to 2 mm×2 mm.

Next, as pretreatment for forming the light-emitting element over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, BPAFLP and molybdenum(VI) oxide were co-evaporated to form a hole-injection layer 1111 over the first electrode 1101. The thickness of the hole-injection layer 1111 was set to 40 nm, and the weight ratio of BPAFLP to molybdenum oxide was adjusted to 4:2 (=BPAFLP:molybdenum oxide).

Next, over the hole-injection layer 1111, a film of BPAFLP was formed to a thickness of 20 nm to form a hole-transport layer 1112.

Furthermore, 2mDBTPDBq-II, PCBNBB, and [Ir(mppr-Me)$_2$(dpm)] were co-evaporated to form a light-emitting layer 1113 over the hole-transport layer 1112. Here, the weight ratio of 2mDBTPDBq-II to PCBNBB and [Ir(mppr-Me)$_2$(dpm)] was adjusted to 0.8:0.2:0.05 (=2mDBTPDBq-II:PCBNBB:[Ir(mppr-Me)$_2$(dpm)]). The thickness of the light-emitting layer 1113 was set to 20 nm.

Further, over the light-emitting layer 1113, 2mDBTPDBq-II, PCBNBB, and [Ir(mppr-Me)$_2$(dpm)] were co-evaporated to form a first electron-transport layer 1114a over the light-emitting layer 1113. Here, the weight ratio of 2mDBTPDBq-III to PCBNBB and [Ir(mppr-Me)$_2$(dpm)] was adjusted to 0.8:0.2:0.05 (=2mDBTPDBq-III:PCBNBB:[Ir(mppr-Me)$_2$(dpm)]). The thickness of the first electron-transport layer 1114a was set to 40 nm.

Next, over the first electron-transport layer 1114a, a film of BPhen was formed to a thickness of 10 nm to form a second electron-transport layer 1114b.

Further, over the second electron-transport layer 1114b, a film of LiF was formed by evaporation to a thickness of 1 nm to form an electron-injection layer 1115.

Lastly, an aluminum film was formed by evaporation to a thickness of 200 nm as a second electrode 1103 functioning as a cathode. Thus, the light-emitting element 15 of this example was fabricated.

(Light-emitting Element 16)

A light-emitting layer 1113 of the light-emitting element 16 was formed by co-evaporating 2mDBTPDBq-II, PCCP, and [Ir(mppr-Me)$_2$(dpm)]. Here, the weight ratio of 2mDBTPDBq-II to PCCP and [Ir(mppr-Me)$_2$(dpm)] was adjusted to 0.8:0.2:0.05 (=2mDBTPDBq-II:PCCP:[Ir(mppr-Me)$_2$(dpm)]). The thickness of the light-emitting layer 1113 was set to 20 nm. Components other than the light-emitting layer 1113 were manufactured in a manner similar to that of the light-emitting element 15.

Note that, in all the above evaporation steps, evaporation was performed by a resistance-heating method.

Table 17 shows element structures of the light-emitting element 15 and the light-emitting element 16 obtained as described above.

TABLE 17

|  | first electrode | hole-injection layer | hole-transport layer | light-emitting layer |
|---|---|---|---|---|
| light-emitting element 15 | ITSO 110 nm | BPAFLP:MoOx (=4:2) 40 nm | BPAFLP 20 nm | 2mDBTPDBq-II:PCBNBB:[Ir(mppr-Me)$_2$(dpm)] (=0.8:0.2:0.05) 20 nm |
| light-emitting element 16 | ITSO 110 nm | BPAFLP:MoOx (=4:2) 40 nm | BPAFLP 20 nm | 2mDBTPDBq-II:PCCP:[Ir(mppr-Me)$_2$(dpm)] (=0.8:0.2:0.05) 20 nm |

|  | first electron-transport layer | second electron-transport layer | electron-injection layer | second electrode |
|---|---|---|---|---|
| light-emitting element 15 | 2mDBTPDBq-II:PCBNBB:[Ir(mppr-Me)$_2$(dpm)] (=0.8:0.2:0.05) 40 nm | BPhen 10 nm | LiF 1 nm | Al 200 nm |
| light-emitting element 16 | 2mDBTPDBq-II:PCBNBB:[Ir(mppr-Me)$_2$(dpm)] (=0.8:0.2:0.05) 40 nm | BPhen 10 nm | LiF 1 nm | Al 200 nm |

In a glove box containing a nitrogen atmosphere, these light-emitting elements were sealed so as not to be exposed to air. Then, operation characteristics of these light-emitting elements were measured. Note that the measurements were carried out at room temperature (in the atmosphere kept at 25° C.).

Figure 59:
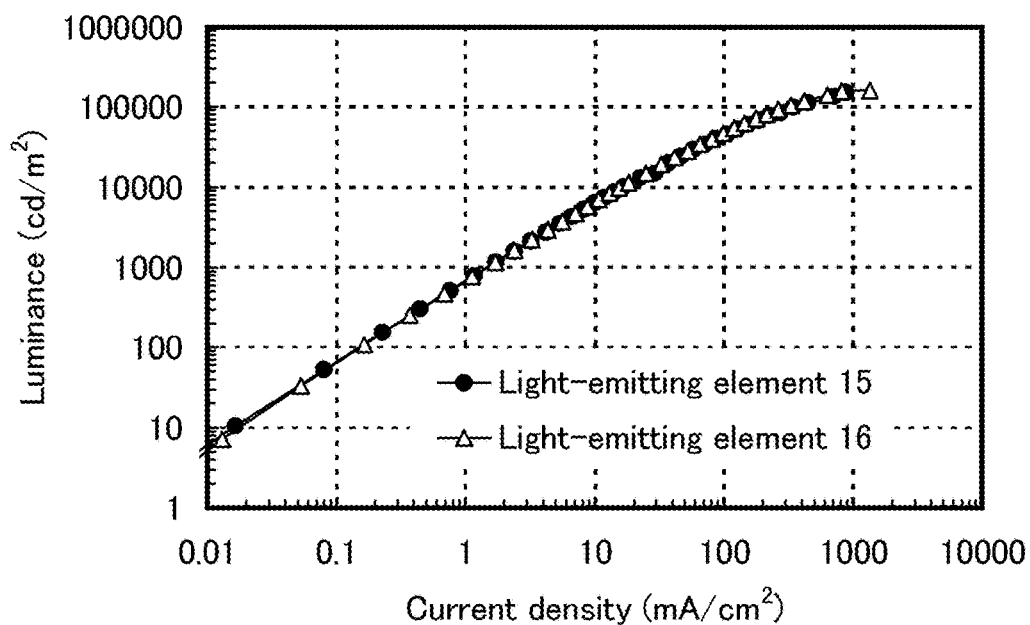
FIG. 59 shows current density-luminance characteristics of light-emitting elements of Example 18.
Figure 60:
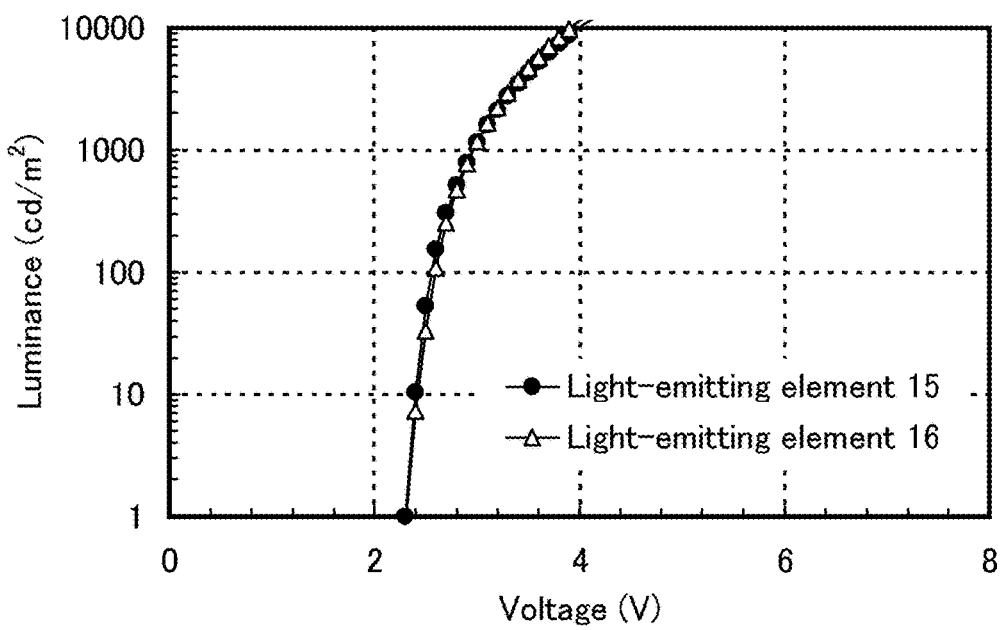
FIG. 60 shows voltage-luminance characteristics of the light-emitting elements of Example 18.
Figure 61:
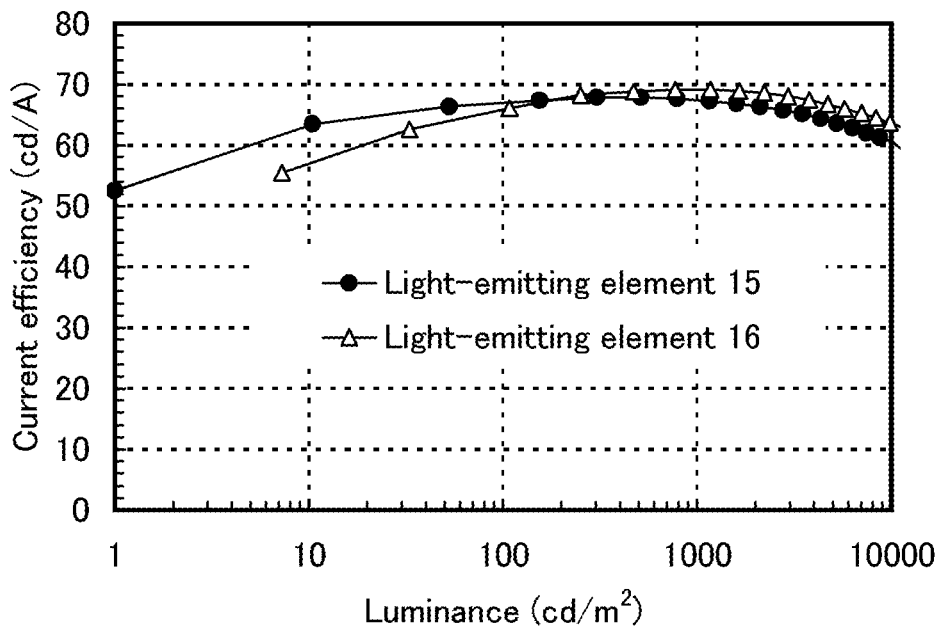
FIG. 61 shows luminance-current efficiency characteristics of the light-emitting elements of Example 18.
Figure 62:
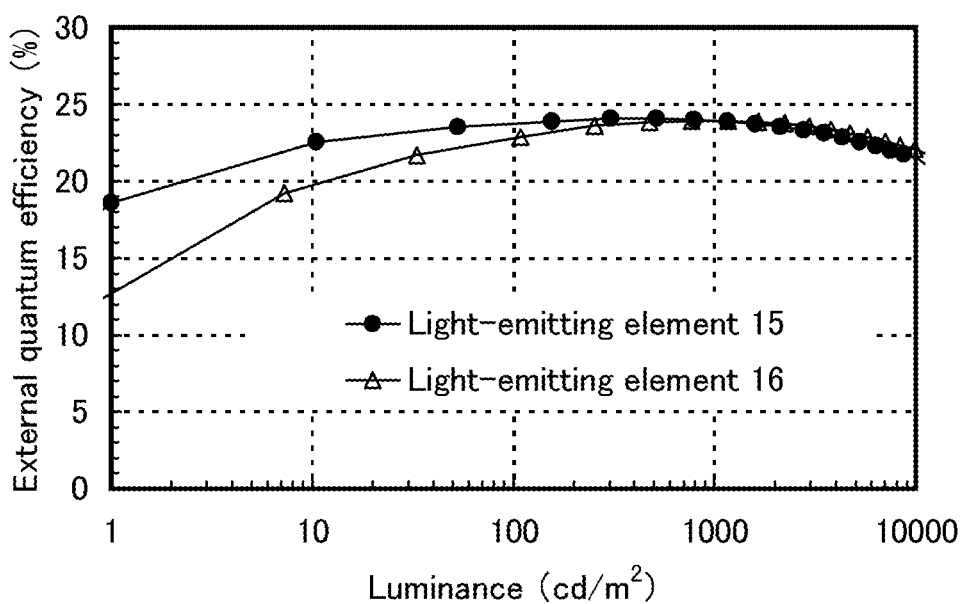
FIG. 62 shows luminance-external quantum efficiency characteristics of the light-emitting elements of Example 18.

FIG. 59 shows current density-luminance characteristics of the light-emitting element 15 and the light-emitting element 16. In FIG. 59, the horizontal axis represents current density (mA/cm$^2$), and the vertical axis represents luminance (cd/m$^2$). FIG. 60 shows voltage-luminance characteristics thereof. In FIG. 60, the horizontal axis represents voltage (V), and the vertical axis represents luminance (cd/m$^2$). FIG. 61 shows luminance-current efficiency characteristics thereof. In FIG. 61, the horizontal axis represents luminance (cd/m$^2$), and the vertical axis represents current efficiency (cd/A). FIG. 62 shows luminance-external quantum efficiency characteristics thereof. In FIG. 62, the horizontal axis represents luminance (cd/m$^2$), and the vertical axis represents external quantum efficiency (%).

Further, Table 18 shows the voltage (V), current density (mA/cm$^2$), CIE chromaticity coordinates (x, y), current efficiency (cd/A), power efficiency (lm/W), and external quantum efficiency (%) of each of the light-emitting element 15 and the light-emitting element 16 at a luminance of 1200 cd/m$^2$.

Figure 63:
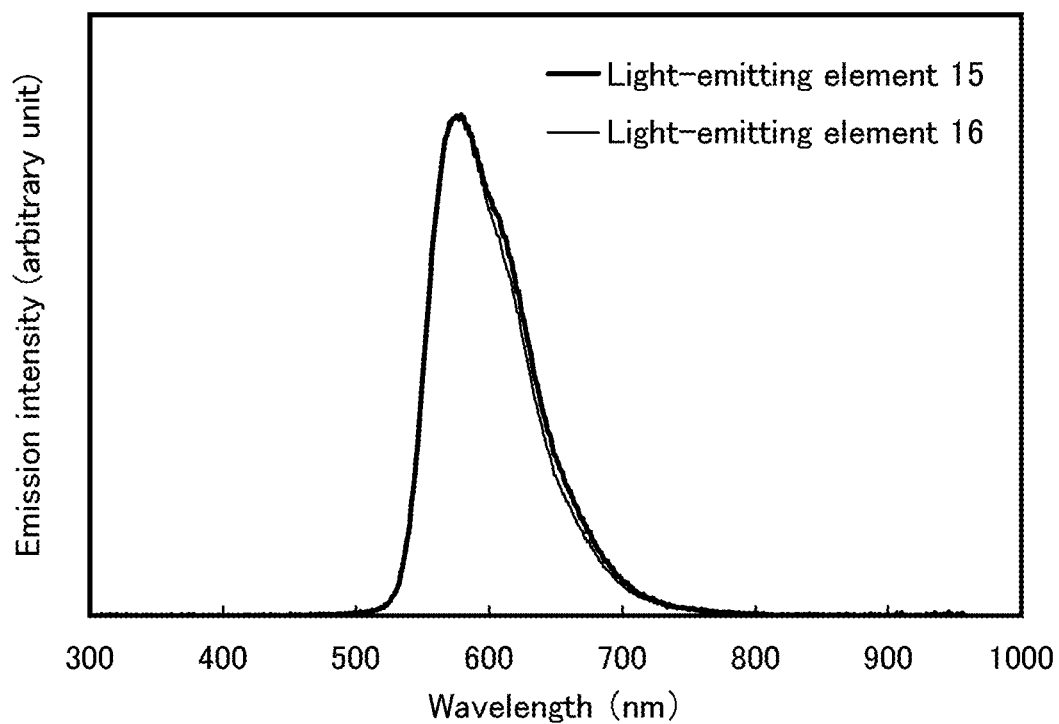
FIG. 63 shows emission spectra of the light-emitting elements of Example 18.

FIG. 63 shows emission spectra of the light-emitting element 15 and the light-emitting element 16 which were obtained by applying a current of 0.1 mA. In FIG. 63, the horizontal axis represents wavelength (nm), and the vertical axis represents emission intensity (arbitrary unit). As shown in Table 18, the CIE chromaticity coordinates of the light-emitting element 15 at a luminance of 1200 cd/m$^2$ were (x, y)=(0.54, 0.45), and the CIE chromaticity coordinates of the light-emitting element 16 at a luminance of 1200 cd/m$^2$ were (x, y)=(0.54, 0.46). These results show that orange light emission originating from [Ir(mppr-Me)$_2$(dpm)] was obtained from the light-emitting element 15 and the light-emitting element 16.

As can be seen from Table 18 and FIGS. 59 to 62, the light-emitting element 15 and the light-emitting element 16 each have high current efficiency, high power efficiency, and high external quantum efficiency.

In each of the light-emitting element 15 and the light-emitting element 16, 2mDBTPDBq-II, PCBNBB or PCCP, and [Ir(mppr-Me)$_2$(dpm)] described in Example 17 are used for the light-emitting layer. As described in Example 17, the emission spectrum of the mixed material of 2mDBTPDBq-II and PCBNBB or PCCP (the emission spectrum of an exciplex) has a large overlap with the absorption band in the absorption spectrum of [Ir(mppr-Me)$_2$(dpm)] which is considered to greatly contribute to light emission. The light-emitting element 15 and the light-emitting element 16 are considered to have high energy transfer efficiency because

TABLE 18

|  | voltage (V) | current density (mA/cm$^2$) | chromaticity coordinates (x, y) | luminance (cd/m$^2$) | current efficiency (cd/A) | power efficiency (lm/W) | external quantum efficiency (%) |
|---|---|---|---|---|---|---|---|
| light-emitting element 15 | 3.0 | 1.7 | (0.54, 0.45) | 1200 | 67 | 70 | 24 |
| light-emitting element 16 | 3.0 | 1.7 | (0.54, 0.46) | 1200 | 69 | 72 | 24 | they each transfer energy by utilizing the overlap, and therefore have high external quantum efficiency.

In addition, this example shows that an exciplex can be formed by using either an aromatic amine based compound (PCBNBB) or a carbazole compound (PCCP) and a light-emitting layer having high external quantum efficiency can be obtained.

The above results show that an element having high external quantum efficiency can be obtained by application of one embodiment of the present invention.

REFERENCE EXAMPLE 1

A synthetic example of an organometallic complex (acetylacetonato)bis(4,6-diphenylpyrimidinato)iridium(III) (another name: bis[2-(6-phenyl-4-pyrimidinyl-κC3)phenyl-κC] (2,4-pentanedionato-κ²O,O')iridium(III)) (abbreviation: [Ir(dppm)$_2$(acac)]), which is used in the above examples, is described. The structure of [Ir(dppm)$_2$(acac)] is shown below.

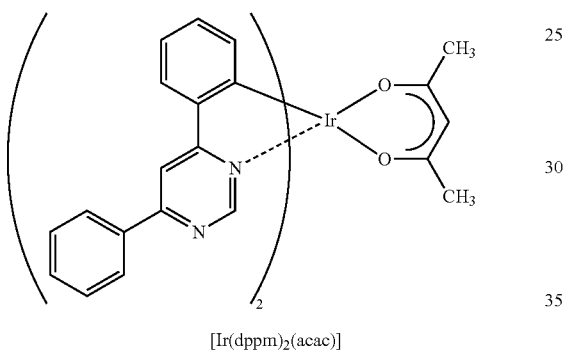

[Ir(dppm)$_2$(acac)]

Step 1: Synthesis of 4,6-Diphenylpyrimidine (Abbreviation: Hdppm)

First, 5.02 g of 4,6-dichloropyrimidine, 8.29 g of phenylboronic acid, 7.19 g of sodium carbonate, 0.29 g of bis(triphenylphosphine)palladium(II)dichloride (abbreviation: Pd(PPh$_3$)$_2$Cl$_2$), 20 mL of water, and 20 mL of acetonitrile were put into a recovery flask equipped with a reflux pipe, and the air in the flask was replaced with argon. This reaction container was heated by irradiation with microwaves (2.45 GHz, 100 W) for 60 minutes. Here, there were further put 2.08 g of phenylboronic acid, 1.79 g of sodium carbonate, 0.070 g of Pd(PPh$_3$)$_2$Cl$_2$, 5 mL of water, and 5 mL of acetonitrile into the flask, and the mixture was heated again by irradiation with microwaves (2.45 GHz, 100 W) for 60 minutes. After that, water was added to this solution and an organic layer was extracted with dichloromethane. The obtained solution of the extract was washed with water and dried with magnesium sulfate. The solution after drying was filtered. The solvent of this solution was distilled off, and then the obtained residue was purified by silica gel column chromatography using dichloromethane as a developing solvent, so that a pyrimidine derivative Hdppm (yellow white powder, yield of 38%) was obtained. Note that for the irradiation with microwaves, a microwave synthesis system (Discover, manufactured by CEM Corporation) was used. A synthesis scheme (a-1) of Step 1 is shown below.

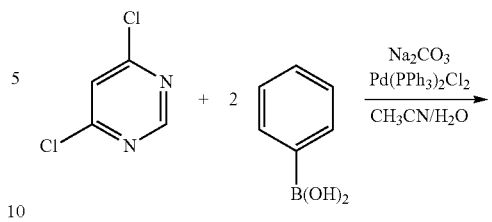

(a-1)

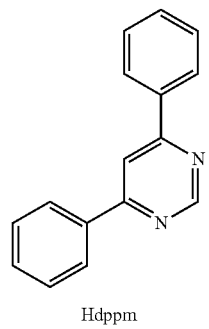

Hdppm

Step 2: Synthesis of Di-μ-chloro-bis[bis(4,6-diphenylpyrimidinato)iridium(III)](Abbreviation: [Ir(dppm)$_2$Cl]$_2$)

Next, 15 mL of 2-ethoxyethanol, 5 mL of water, 1.10 g of Hdppm obtained in Step 1, and 0.69 g of iridium chloride hydrate (IrCl$_3$.H$_2$O) were put into a recovery flask equipped with a reflux pipe, and the air in the recovery flask was replaced with argon. After that, irradiation with microwaves (2.45 GHz, 100 W) was performed for 1 hour to cause a reaction. The solvent was distilled off, and then the obtained residue was filtered and washed with ethanol to give a dinuclear complex [Ir(dppm)$_2$Cl]$_2$ (reddish brown powder, yield of 88%). A synthesis scheme (a-2) of Step 2 is shown below.

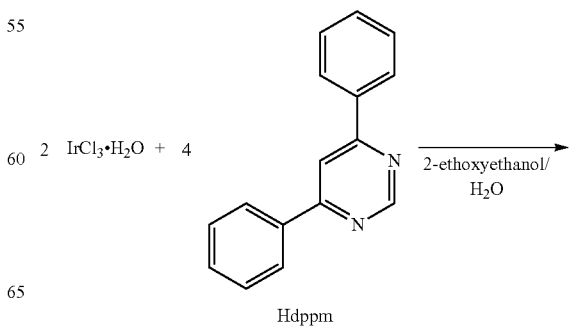

(a-2)

Hdppm

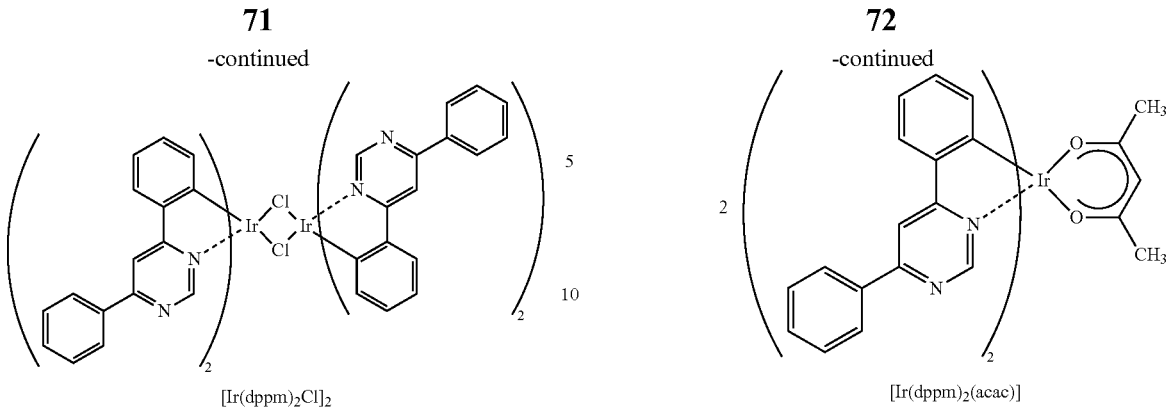

[Ir(dppm)₂Cl]₂

[Ir(dppm)₂(acac)]

Step 3: Synthesis of (Acetylacetonato)bis(4,6-diphenylpyrimidinato)iridium(III) (Abbreviation: [Ir(dppm)₂(acac)])

Furthermore, 40 mL of 2-ethoxyethanol, 1.44 g of [Ir(dppm)₂Cl]₂ obtained in Step 2, 0.30 g of acetylacetone, and 1.07 g of sodium carbonate were put into a recovery flask equipped with a reflux pipe, and the air in the recovery flask was replaced with argon. After that, irradiation with microwaves (2.45 GHz, 120 W) was performed for 60 minutes to cause a reaction. The solvent was distilled off, the obtained residue was dissolved in dichloromethane, and filtration was performed to remove insoluble matter. The obtained filtrate was washed with water and then with saturated saline, and was dried with magnesium sulfate. The solution after drying was filtered. The solvent of this solution was distilled off, and then the obtained residue was purified by silica gel column chromatography using dichloromethane and ethyl acetate as a developing solvent in a volume ratio of 50:1. After that, recrystallization was carried out with a mixed solvent of dichloromethane and hexane, so that the objective orange powder (yield of 32%) was obtained. A synthesis scheme (a-3) of Step 3 is shown below.

(a-3)

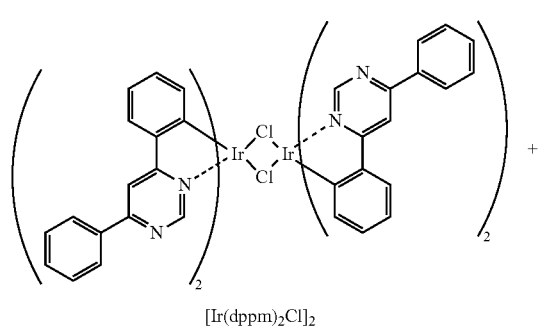

[Ir(dppm)₂Cl]₂

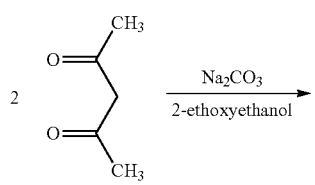

An analysis result by nuclear magnetic resonance spectrometry (¹H NMR) of the orange powder obtained in Step 3 is described below. These results revealed that the organometallic complex [Ir(dppm)₂(acac)] was obtained.

¹H NMR. δ (CDCl₃): 1.83 (s, 6H), 5.29 (s, 1H), 6.48 (d, 2H), 6.80 (t, 2H), 6.90 (t, 2H), 7.55-7.63 (m, 6H), 7.77 (d, 2H), 8.17 (s, 2H), 8.24 (d, 4H), 9.17 (s, 2H).

REFERENCE EXAMPLE 2

A synthetic example of an organometallic complex (acetylacetonato)bis(6-methyl-4-phenylpyrimidinato)iridium(III) (another name: bis[2-(6-methyl-4-pyrimidinyl-κC)phenyl-κC](2,4-pentanedionato-κ²O,O')iridium(III)) (abbreviation: [Ir(mppm)₂(acac)]), which is used in the above examples, is specifically described. The structure of [Ir(mppm)₂(acac)] is shown below.

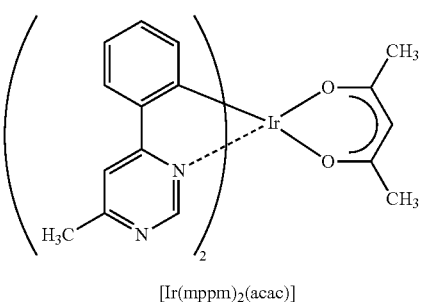

[Ir(mppm)₂(acac)]

Step 1: Synthesis of 4-Methyl-6-phenylpyrimidine (Abbreviation: Hmppm)

First, 4.90 g of 4-chloro-6-methylpyrimidine, 4.80 g of phenylboronic acid, 4.03 g of sodium carbonate, 0.16 g of bis(triphenylphosphine)palladium(II)dichloride (abbreviation: Pd(PPh₃)₂Cl₂), 20 mL of water, and 10 mL of acetonitrile were put into a recovery flask equipped with a reflux pipe, and the air in the flask was replaced with argon. This reaction container was heated by irradiation with microwaves (2.45 GHz, 100 W) for 60 minutes. Here, there were further put 2.28 g of phenylboronic acid, 2.02 g of sodium carbonate, 0.082 g of Pd(PPh₃)₂Cl₂, 5 mL of water, and 10 mL of acetonitrile in the flask, and the mixture was heated again by irradiation with microwaves (2.45 GHz, 100 W) for 60 minutes. After that, water was added to this solution and extraction with dichloromethane was carried out. The obtained solution of the extract was washed with a saturated aqueous solution of sodium carbonate, water, and then with saturated saline, and dried with magnesium sulfate. The solution after drying was filtered. The solvent of this solution was distilled off, and then the obtained residue was purified by silica gel column chromatography using dichloromethane and ethyl acetate as a developing solvent in a volume ratio of 9:1, so that the objective pyrimidine derivative Hmppm (orange oily substance, yield of 46%) was obtained. Note that the irradiation with microwaves was performed using a microwave synthesis system (Discover, manufactured by CEM Corporation). A synthesis scheme (b-1) of Step 1 is shown below.

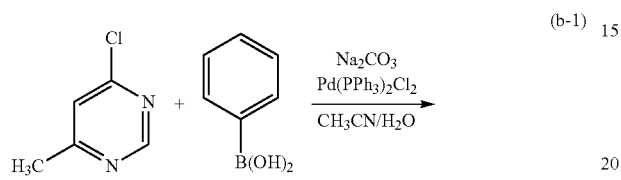

(b-1)

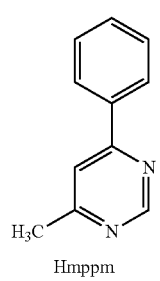

Hmppm

Step 2: Synthesis of Di-µ-chloro-bis[bis(6-methyl-4-phenylpyrimidinato)iridium(III)](Abbreviation: [Ir(mppm)$_2$Cl]$_2$)

Next, 15 mL of 2-ethoxyethanol, 5 mL of water, 1.51 g of Hmppm obtained in Step 1, and 1.26 g of iridium chloride hydrate (IrCl$_3$.H$_2$O) were put into a recovery flask equipped with a reflux pipe, and the air in the recovery flask was replaced with argon. After that, irradiation with microwaves (2.45 GHz, 100 W) was performed for 1 hour to cause a reaction. The solvent was distilled off, and then the obtained residue was washed with ethanol and filtered, so that a dinuclear complex [Ir(mppm)$_2$Cl]$_2$ (dark green powder, yield of 77%) was obtained. A synthesis scheme (b-2) of Step 2 is shown below.

(b-2)

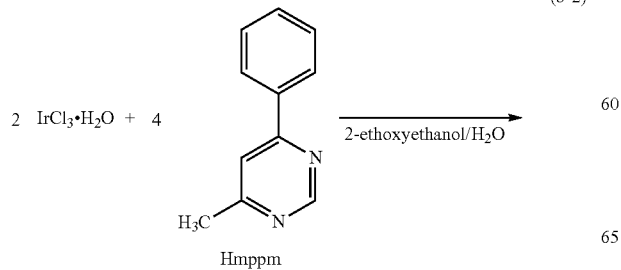

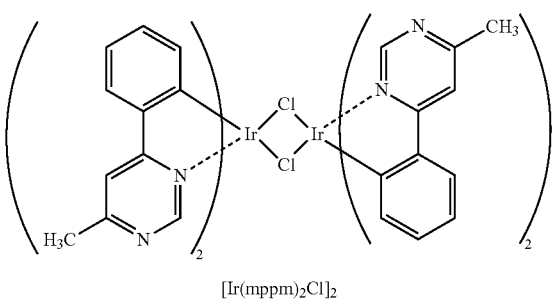

[Ir(mppm)$_2$Cl]$_2$

Step 3: Synthesis of (Acetylacetonato)bis(6-methyl-4-phenylpyrimidinato)iridium(III) (Abbreviation: [Ir(mppm)$_2$(acac)])

Furthermore, 40 mL of 2-ethoxyethanol, 1.84 g of the dinuclear complex [Ir(mppm)$_2$Cl]$_2$ obtained in Step 2, 0.48 g of acetylacetone, and 1.73 g of sodium carbonate were put into a recovery flask equipped with a reflux pipe, and the air in the recovery flask was replaced with argon. After that, irradiation with microwaves (2.45 GHz, 120 W) was performed for 60 minutes to cause a reaction. The solvent was distilled off, the obtained residue was dissolved in dichloromethane, and filtration was performed to remove insoluble matter. The obtained filtrate was washed with water and then with saturated saline, and was dried with magnesium sulfate. The solution after drying was filtered. The solvent of this solution was distilled off, and then the obtained residue was purified by silica gel column chromatography using dichloromethane and ethyl acetate as a developing solvent in a volume ratio of 4:1. After that, recrystallization was carried out with a mixed solvent of dichloromethane and hexane, so that the objective yellow powder (yield of 22%) was obtained. A synthesis scheme (b-3) of Step 3 is shown below.

(b-3)

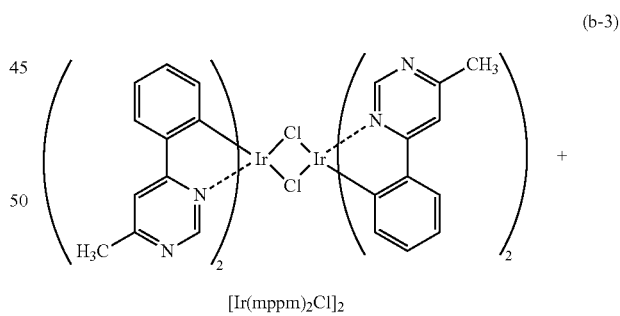

[Ir(mppm)$_2$Cl]$_2$

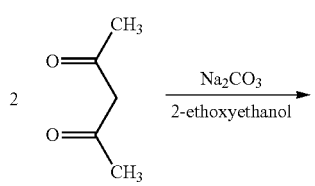

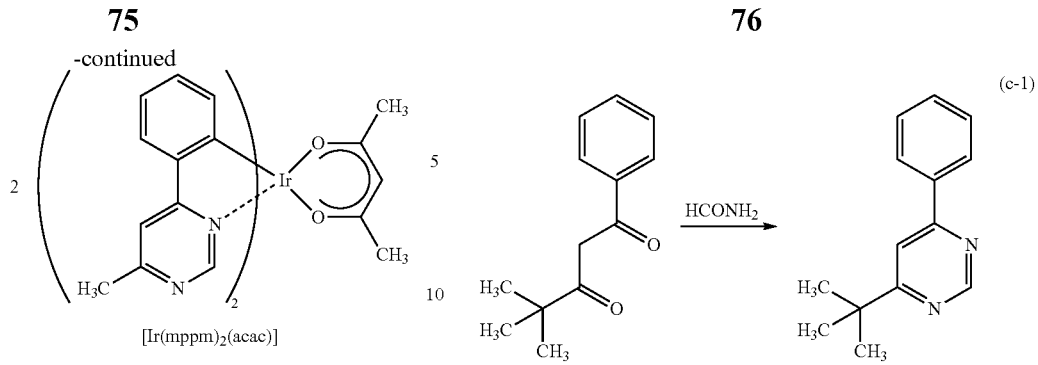

[Ir(mppm)₂(acac)]

An analysis result by nuclear magnetic resonance spectrometry (¹H NMR) of the yellow powder obtained in Step 3 is described below. These results revealed that the organometallic complex [Ir(mppm)₂(acac)] was obtained.

¹H NMR. δ (CDCl₃): 1.78 (s, 6H), 2.81 (s, 6H), 5.24 (s, 1H), 6.37 (d, 2H), 6.77 (t, 2H), 6.85 (t, 2H), 7.61-7.63 (m, 4H), 8.97 (s, 2H).

REFERENCE EXAMPLE 3

A synthetic example of an organometallic complex (acetylacetonato)bis(6-tert-butyl-4-phenylpyrimidinato)iridium(III) (another name: bis[2-(6-tert-butyl-4-pyrimidinyl-κN3)phenyl-κC](2,4-pentanedionato-κ²O,O')iridium(III)) (abbreviation: [Ir(tBuppm)₂(acac)]), which is used in the above examples, is described. The structure of [Ir(tBuppm)₂(acac)] is shown below.

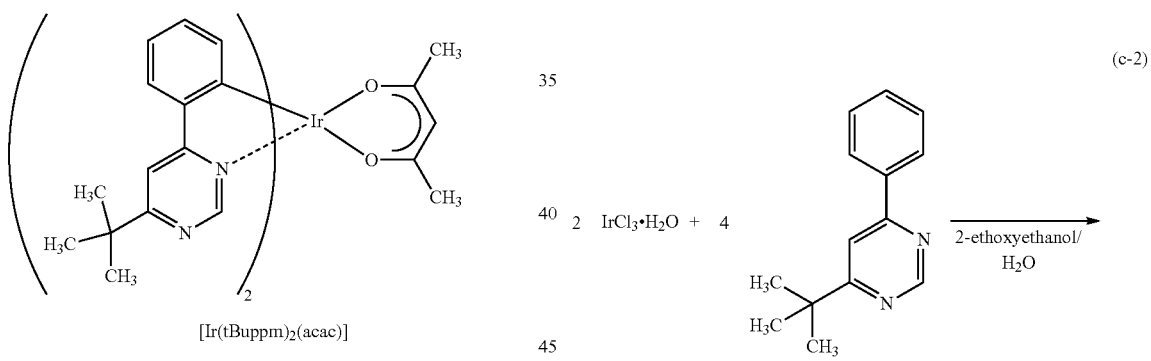

[Ir(tBuppm)₂(acac)]

Step 1: Synthesis of 4-tert-Butyl-6-phenylpyrimidine (abbreviation: HtBuppm)

First, 22.5 g of 4,4-dimethyl-1-phenylpentane-1,3-dione and 50 g of formamide were put into a recovery flask equipped with a reflux pipe, and the air in the flask was replaced with nitrogen. This reaction container was heated, so that the reacted solution was refluxed for 5 hours. After that, this solution was poured into an aqueous solution of sodium hydroxide, and an organic layer was extracted with dichloromethane. The obtained organic layer was washed with water and saturated saline, and dried with magnesium sulfate. The solution after drying was filtered. The solvent of this solution was distilled off, and then the obtained residue was purified by silica gel column chromatography using hexane and ethyl acetate as a developing solvent in a volume ratio of 10:1, so that a pyrimidine derivative HtBuppm (colorless oily substance, yield of 14%) was obtained. A synthetic scheme (c-1) of Step 1 is shown below.

(c-1)

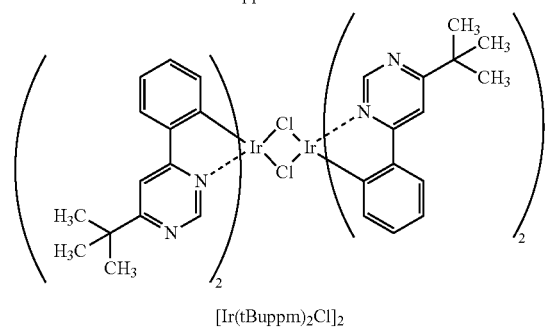

HtBuppm

Step 2: Synthesis of Di-μ-chloro-bis[bis(6-tert-butyl-4-phenylpyrimidinato)iridium(III)](Abbreviation: [Ir(tBuppm)₂Cl]₂)

Next, 15 mL of 2-ethoxyethanol, 5 mL of water, 1.49 g of HtBuppm obtained in Step 1, and 1.04 g of iridium chloride hydrate (IrCl₃·H₂O) were put into a recovery flask equipped with a reflux pipe, and the air in the flask was replaced with argon. After that, irradiation with microwaves (2.45 GHz, 100 W) was performed for 1 hour to cause a reaction. The solvent was distilled off, and then the obtained residue was suction-filtered and washed with ethanol, so that a dinuclear complex [Ir(tBuppm)₂Cl]₂ (yellow green powder, yield of 73%) was obtained. A synthesis scheme (c-2) of Step 2 is shown below.

(c-2)

Step 3: Synthesis of (Acetylacetonato)bis(6-tert-butyl-4-phenylpyrimidinato)iridium(III) (Abbreviation: [Ir(tBuppm)₂(acac)])

Further, 40 mL of 2-ethoxyethanol, 1.61 g of the dinuclear complex [Ir(tBuppm)₂Cl]₂ obtained in Step 2, 0.36 g of acetylacetone, and 1.27 g of sodium carbonate were put into a recovery flask equipped with a reflux pipe, and the air in the flask was replaced with argon. After that, irradiation with microwaves (2.45 GHz, 120 W) was performed for 60 minutes to cause a reaction. The solvent was distilled off, and the obtained residue was suction-filtered with ethanol and washed with water and ethanol. This solid was dissolved in dichloromethane, and the mixture was filtered through a filter aid in which Celite (produced by Wako Pure Chemical Industries, Ltd., Catalog No. 531-16855), alumina, and Celite were stacked in this order. The solvent was distilled off, and the obtained solid was recrystallized with a mixed solvent of dichloromethane and hexane, so that the objective substance was obtained as yellow powder (yield of 68%). A synthesis scheme (c-3) of Step 3 is shown below.

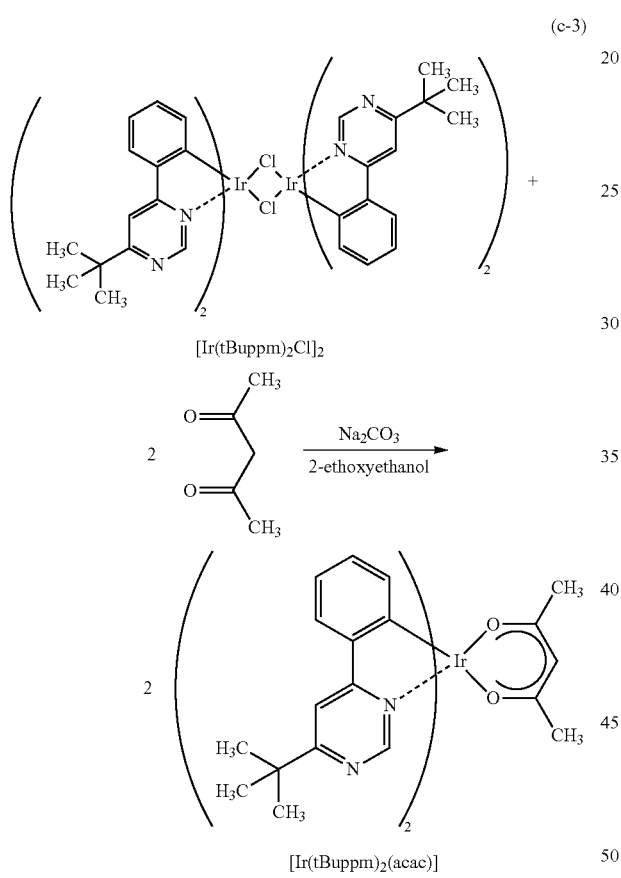

An analysis result by nuclear magnetic resonance spectrometry ($^1$H NMR) of the yellow powder obtained in Step 3 is described below. These results revealed that the organometallic complex [Ir(tBuppm)$_2$(acac)] was obtained.

$^1$H NMR. δ (CDCl$_3$): 1.50 (s, 18H), 1.79 (s, 6H), 5.26 (s, 1H), 6.33 (d, 2H), 6.77 (t, 2H), 6.85 (t, 2H), 7.70 (d, 2H), 7.76 (s, 2H), 9.02 (s, 2H).

REFERENCE EXAMPLE 4

A method of synthesizing 2-[3-(dibenzothiophen-4-yl)phenyl]dibenzo[f,h]quinoxaline (abbreviation: 2mDBTP-DBq-II), which is used in the above examples, is described.

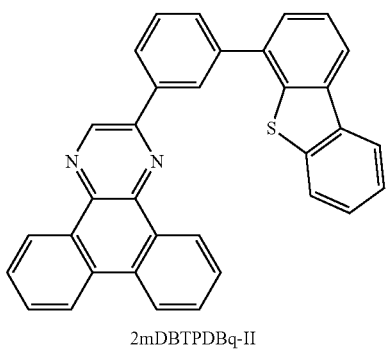 [SMILES: c1cc(-c2cnc3c4ccccc4c4ccccc4c3n2)cc(-c2cccc3c2sc2ccccc23)c1]

2mDBTPDBq-II

Synthesis of 2-[3-(Dibenzothiophen-4-yl)phenyl]dibenzo[f,h]quinoxaline (Abbreviation: 2mDBTP-DBq-II)

A synthesis scheme (d-1) of 2-[3-(dibenzothiophen-4-yl)phenyl]dibenzo[f,h]quinoxaline (abbreviation: 2mDBTP-DBq-II) is shown below.

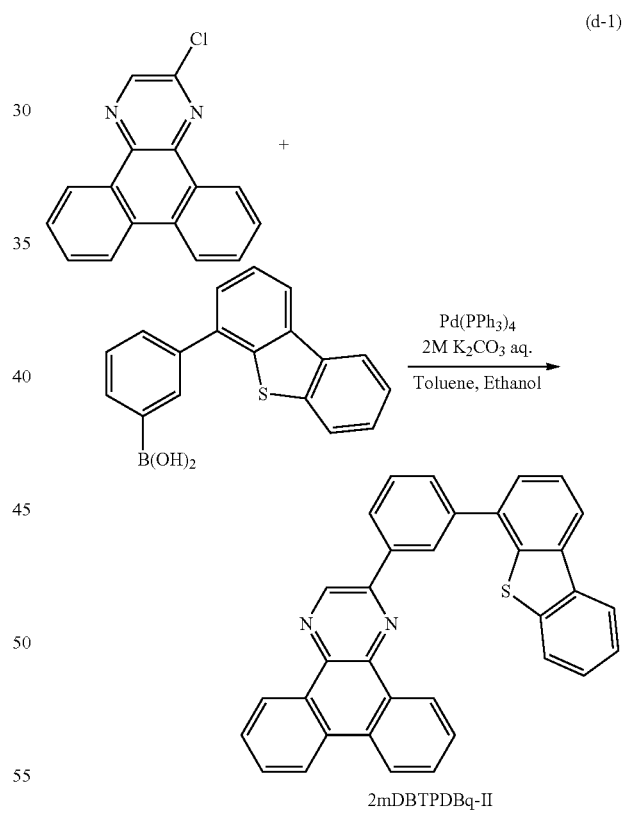

First, 5.3 g (20 mmol) of 2-chlorodibenzo[f,h]quinoxaline, 6.1 g (20 mmol) of 3-(dibenzothiophen-4-yl)phenylboronic acid, 460 mg (0.4 mmol) of tetrakis(triphenylphosphine)palladium(0), 300 mL of toluene, 20 mL of ethanol, and 20 mL of a 2M aqueous solution of potassium carbonate were put in a 2 L three-neck flask. The mixture was degassed by being stirred under reduced pressure, and the air in the three-neck flask was replaced with nitrogen. This mixture was stirred under a nitrogen stream at 100° C. for 7.5 hours.

After cooled to room temperature, the obtained mixture was filtered to give a white residue. The obtained residue was washed with water and ethanol in this order, and then dried. The obtained solid was dissolved in about 600 mL of hot toluene, followed by suction filtration through Celite and Florisil, whereby a clear colorless filtrate was obtained. The obtained filtrate was concentrated and purified by silica gel column chromatography using about 700 mL of silica gel. The chromatography was carried out using hot toluene as a developing solvent. Acetone and ethanol were added to the solid obtained here, followed by irradiation with ultrasonic waves. Then, the generated suspended solid was collected by filtration and the obtained solid was dried, so that 7.85 g of white powder was obtained in 80% yield.

The above objective substance was relatively soluble in hot toluene, but was a material that was likely to be precipitated when cooled. Further, the substance was poorly soluble in other organic solvents such as acetone and ethanol. Hence, the utilization of these different degrees of solubility resulted in a high-yield synthesis by a simple method as above. Specifically, after the reaction finished, the mixture was returned to room temperature and the precipitated solid was collected by filtration, whereby most impurities were able to be easily removed. Further, by the column chromatography with hot toluene as a developing solvent, the objective substance, which is likely to be precipitated, was able to be readily purified.

By a train sublimation method, 4.0 g of the obtained white powder was purified. In the purification, the white powder was heated at 300° C. under a pressure of 5.0 Pa with a flow rate of argon gas of 5 mL/min. After the purification, the objective substance was obtained in a yield of 88% as 3.5 g of white powder.

A nuclear magnetic resonance spectrometry ($^1$H NMR) identified this compound as the objective 2-[3-(dibenzothiophen-4-yl)phenyl]dibenzo[f,h]quinoxaline (abbreviation: 2mDBTPDBq-II).

$^1$H NMR data of the obtained substance are shown below.

$^1$H NMR (CDCl$_3$, 300 MHz): δ (ppm)=7.45-7.52 (m, 2H), 7.59-7.65 (m, 2H), 7.71-7.91 (m, 7H), 8.20-8.25 (m, 2H), 8.41 (d, J=7.8 Hz, 1H), 8.65 (d, J=7.5 Hz, 2H), 8.77-8.78 (m, 1H), 9.23 (dd, J=7.2 Hz, 1.5 Hz, 1H), 9.42 (dd, J=7.8 Hz, 1.5 Hz, 1H), 9.48 (s, 1H).

EXPLANATION OF REFERENCE

102: EL layer, 103: first electrode, 108: second electrode, 701: hole-injection layer, 702: hole-transport layer, 703: light-emitting layer, 704: electron-transport layer, 705: electron-injection layer, 706: electron-injection buffer layer, 707: electron-relay layer, 708: composite material layer, 800: first EL layer, 801: second EL layer, 803: charge-generation layer, 1100: substrate, 1101: first electrode, 1103: second electrode, 1111: hole-injection layer, 1112: hole-transport layer, 1113: light-emitting layer, 1114a: first electron-transport layer, 1114b: second electron-transport layer, and 1115: electron-injection layer.

This application is based on Japanese Patent Application serial no. 2011-031462 filed with Japan Patent Office on Feb. 16, 2011, the entire contents of which are hereby incorporated by reference.

The invention claimed is:

1. A method of emitting light from a light-emitting element comprising a first compound, a second compound, and a phosphorescent compound between a pair of electrodes, the method comprising:

forming an exciplex between the first compound and the second compound; and transferring an excitation energy from the exciplex to the phosphorescent compound, wherein the phosphorescent compound has an absorption spectrum comprising absorption bands, an emission spectrum of the exciplex overlaps with the absorption band having the longest wavelength, and a difference between an energy value of a peak of the emission spectrum and an energy value of a peak of the absorption band having the longest wavelength is 0.2 eV or less, and wherein each of a level of a triplet excitation energy of the first compound and a level of a triplet excitation energy of the second compound is higher than a level of a triplet excitation energy of the phosphorescent compound.

2. The method according to claim 1, wherein the difference between the energy value of the peak of the emission spectrum and the energy value of the peak of the absorption band having the longest wavelength is 0.1 eV or less.

3. The method according to claim 1, wherein the emission spectrum is a fluorescence spectrum.

4. The method according to claim 1, wherein the phosphorescent compound is an organometallic complex.

5. The method according to claim 1, wherein the phosphorescent compound is an iridium complex.

6. The method according to claim 1, wherein a molar absorption coefficient of the absorption band having the longest wavelength is 2000 $M^{-1} \cdot cm^{-1}$ or higher.

7. The method according to claim 1, wherein the first compound comprises a heterocyclic compound, and wherein the second compound comprises a carbazole compound.

8. The method according to claim 1, wherein the light-emitting element comprises a light-emitting layer and a hole-injection layer between the pair of electrodes, and wherein the light-emitting layer comprises the first compound, the second compound, and the phosphorescent compound.

9. The method according to claim 1, wherein the light-emitting element comprises a light-emitting layer and a hole-injection layer between the pair of electrodes, wherein the light-emitting layer comprises the first compound, the second compound, and the phosphorescent compound, and wherein the hole-injection layer comprises an organic compound and an electron acceptor.

10. A method of emitting light from a light-emitting element comprising a first compound, a second compound, and a phosphorescent compound between a pair of electrodes, the method comprising:

applying a voltage between the pair of electrodes to form an exciplex between the first compound and the second compound, wherein an excitation energy of the exciplex is transferred to the phosphorescent compound, wherein the phosphorescent compound has an absorption spectrum comprising absorption bands, an emission spectrum of the exciplex overlaps with the absorption band having the longest wavelength, and a difference between an energy value of a peak of the emission spectrum and an energy value of a peak of the absorption band having the longest wavelength is 0.2 eV or less, and wherein each of a level of a triplet excitation energy of the first compound and a level of a triplet excitation energy of the second compound is higher than a level of a triplet excitation energy of the phosphorescent compound.

11. The method according to claim 10, wherein the difference between the energy value of the peak of the emission spectrum and the energy value of the peak of the absorption band having the longest wavelength is 0.1 eV or less.

12. The method according to claim 10, wherein the emission spectrum is a fluorescence spectrum.

13. The method according to claim 10, wherein the phosphorescent compound is an organometallic complex.

14. The method according to claim 10, wherein the phosphorescent compound is an iridium complex.

15. The method according to claim 10, wherein a molar absorption coefficient of the absorption band having the longest wavelength is 2000 $M^{-1} \cdot cm^{-1}$ or higher.

16. The method according to claim 10,
wherein the first compound comprises a heterocyclic compound, and
wherein the second compound comprises a carbazole compound.

17. The method according to claim 10,
wherein the light-emitting element comprises a light-emitting layer and a hole-injection layer between the pair of electrodes, and
wherein the light-emitting layer comprises the first compound, the second compound, and the phosphorescent compound.

18. The method according to claim 10,
wherein the light-emitting element comprises a light-emitting layer and a hole-injection layer between the pair of electrodes,
wherein the light-emitting layer comprises the first compound, the second compound, and the phosphorescent compound, and
wherein the hole-injection layer comprises an organic compound and an electron acceptor.

19. A method of using a light-emitting element comprising a first compound, a second compound, and a phosphorescent compound between a pair of electrodes, the method comprising:
forming an exciplex between the first compound and the second compound; and
transferring an excitation energy from the exciplex to the phosphorescent compound,
wherein the phosphorescent compound has an absorption spectrum comprising absorption bands, an emission spectrum of the exciplex overlaps with the absorption band having the longest wavelength, and a difference between an energy value of a peak of the emission spectrum and an energy value of a peak of the absorption band having the longest wavelength is 0.2 eV or less, and
wherein each of a level of a triplet excitation energy of the first compound and a level of a triplet excitation energy of the second compound is higher than a level of a triplet excitation energy of the phosphorescent compound.

20. The method according to claim 19, wherein the difference between the energy value of the peak of the emission spectrum and the energy value of the peak of the absorption band having the longest wavelength is 0.1 eV or less.

21. The method according to claim 19, wherein the emission spectrum is a fluorescence spectrum.

22. The method according to claim 19, wherein the phosphorescent compound is an organometallic complex.

23. The method according to claim 19, wherein the phosphorescent compound is an iridium complex.

24. The method according to claim 19, wherein a molar absorption coefficient of the absorption band having the longest wavelength is 2000 $M^{-1} \cdot cm^{-1}$ or higher.

25. The method according to claim 19,
wherein the first compound comprises a heterocyclic compound, and
wherein the second compound comprises a carbazole compound.

26. The method according to claim 19,
wherein the light-emitting element comprises a light-emitting layer and a hole-injection layer between the pair of electrodes, and
wherein the light-emitting layer comprises the first compound, the second compound, and the phosphorescent compound.

27. The method according to claim 19,
wherein the light-emitting element comprises a light-emitting layer and a hole-injection layer between the pair of electrodes,
wherein the light-emitting layer comprises the first compound, the second compound, and the phosphorescent compound, and
wherein the hole-injection layer comprises an organic compound and an electron acceptor.

28. The method according to claim 19, wherein the light-emitting element emits light.

29. A method of using a light-emitting element comprising a first compound, a second compound, and a phosphorescent compound between a pair of electrodes, the method comprising:
applying a voltage between the pair of electrodes to form an exciplex between the first compound and the second compound,
wherein an excitation energy of the exciplex is transferred to the phosphorescent compound,
wherein the phosphorescent compound has an absorption spectrum comprising absorption bands, an emission spectrum of the exciplex overlaps with the absorption band having the longest wavelength, and a difference between an energy value of a peak of the emission spectrum and an energy value of a peak of the absorption band having the longest wavelength is 0.2 eV or less, and
wherein each of a level of a triplet excitation energy of the first compound and a level of a triplet excitation energy of the second compound is higher than a level of a triplet excitation energy of the phosphorescent compound.

30. The method according to claim 29, wherein the difference between the energy value of the peak of the emission spectrum and the energy value of a peak of the absorption band having the longest wavelength is 0.1 eV or less.

31. The method according to claim 29, wherein the emission spectrum is a fluorescence spectrum.

32. The method according to claim 29, wherein the phosphorescent compound is an organometallic complex.

33. The method according to claim 29, wherein the phosphorescent compound is an iridium complex.

34. The method according to claim 29, wherein a molar absorption coefficient of the absorption band having the longest wavelength is 2000 $M^{-1} \cdot cm^{-1}$ or higher.

35. The method according to claim 29,
wherein the first compound comprises a heterocyclic compound, and
wherein the second compound comprises a carbazole compound.

36. The method according to claim 29,
wherein the light-emitting element comprises a light-emitting layer and a hole-injection layer between the pair of electrodes, and
wherein the light-emitting layer comprises the first compound, the second compound, and the phosphorescent compound.

37. The method according to claim 29,
wherein the light-emitting element comprises a light-emitting layer and a hole-injection layer between the pair of electrodes,
wherein the light-emitting layer comprises the first compound, the second compound, and the phosphorescent compound, and
wherein the hole-injection layer comprises an organic compound and an electron acceptor.

38. The method according to claim 29, wherein the light-emitting element emits light.

* * * * *